US011638740B2

(12) United States Patent
Rajasekhar et al.

(10) Patent No.: US 11,638,740 B2
(45) Date of Patent: *May 2, 2023

(54) METHODS OF TREATING FEMALE INFERTILITY

(71) Applicant: Myovant Sciences GmbH, Basel (CH)

(72) Inventors: Vijaykumar Reddy Rajasekhar, Apple Valley, CA (US); Brendan Mark Johnson, Chapel Hill, NC (US); Laura Ann Williams, Sudbury, MA (US)

(73) Assignee: Myovant Sciences GmbH, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/239,273

(22) Filed: Apr. 23, 2021

(65) Prior Publication Data

US 2022/0088114 A1 Mar. 24, 2022

Related U.S. Application Data

(63) Continuation of application No. 16/369,847, filed on Mar. 29, 2019, now Pat. No. 11,013,780, which is a continuation of application No. PCT/EP2017/074800, filed on Sep. 29, 2017.

(60) Provisional application No. 62/402,150, filed on Sep. 30, 2016, provisional application No. 62/402,018, filed on Sep. 30, 2016.

(51) Int. Cl.
*A61K 38/08* (2019.01)
*A61P 15/08* (2006.01)
*A61K 31/505* (2006.01)
*A61K 31/519* (2006.01)

(52) U.S. Cl.
CPC ............ *A61K 38/08* (2013.01); *A61K 31/505* (2013.01); *A61K 31/519* (2013.01); *A61P 15/08* (2018.01)

(58) Field of Classification Search
None
See application file for complete search history.

(56) References Cited

U.S. PATENT DOCUMENTS

| | | | |
|---|---|---|---|
| 7,056,927 B2 | 6/2006 | Guo et al. | |
| 7,176,211 B2 | 2/2007 | Guo et al. | |
| 7,419,983 B2 | 9/2008 | Guo et al. | |
| 7,960,348 B2 | 6/2011 | Asami et al. | |
| 8,404,643 B2 | 3/2013 | Asami et al. | |
| 8,765,948 B2 | 7/2014 | Gallagher et al. | |
| 9,382,214 B2 | 7/2016 | Gallagher et al. | |
| 9,422,310 B2 | 8/2016 | Beaton et al. | |
| 11,013,780 B2 | 5/2021 | Rajasekhar et al. | |
| 2009/0105152 A1 | 4/2009 | Asami et al. | |
| 2010/0331520 A1 | 12/2010 | Asami et al. | |
| 2011/0052563 A1 | 3/2011 | Ohtaki et al. | |
| 2011/0212890 A1 | 9/2011 | Asami | |
| 2011/0312898 A1 | 12/2011 | Matsui | |
| 2012/0302508 A1 | 11/2012 | Futo et al. | |
| 2013/0210742 A1 | 8/2013 | Futo et al. | |
| 2018/0228732 A1 | 8/2018 | Futo et al. | |
| 2018/0243422 A1 | 8/2018 | Futo et al. | |

FOREIGN PATENT DOCUMENTS

| | | | | |
|---|---|---|---|---|
| JP | 2002-541122 A | | 12/2002 | |
| JP | 2005-097237 A | | 4/2005 | |
| JP | 2007-533748 A | | 11/2007 | |
| JP | 2009-520682 A | | 5/2009 | |
| JP | WO 2011078394 | * | 6/2011 | ............... A61K 9/16 |
| JP | WO 2011162413 | * | 12/2011 | ............. A61K 38/08 |
| JP | 2014-522871 A | | 9/2014 | |
| WO | WO-2006/001499 A2 | | 1/2006 | |
| WO | WO-2006/001499 A3 | | 1/2006 | |
| WO | WO-2007/084211 A2 | | 7/2007 | |
| WO | WO-2007/084211 A3 | | 7/2007 | |
| WO | WO-2010/013762 A1 | | 2/2010 | |
| WO | WO-2010/076896 A1 | | 7/2010 | |

OTHER PUBLICATIONS

Michael Ludwig and Klaus Diedrich, Acta Obstet Gynecol Scand 2001; 80: 452-466 (Year: 2001).*
Kuang et al., Fertil Steril, 2015; 104:62-70 (Year: 2015).*
Moriya et al., Drug Metab Dispos 47:1004-1012 (Year: 2019).*
Abbara, A. et al. (2015). "Efficacy of kisspeptin-54 to trigger oocyte maturation in women at high risk of ovarian hyperstimulation syndrome (OHSS) during in vitro fertilization (IVF) therapy," J. Clin. Endocrinol. Metab. 100:3322-31.
Abbara, A. et al. (2015). Supplemental methods and information, 5 total pages.
Abbara, A. et al. (2020). "Kisspeptin receptor agonist has therapeutic potential for female reproductive disorders," J. Clin. Invest. (in press), with Figures 1-6 and Supplemental Figures, 52 total pages.
Aboulghar, M. (2003). "Prediction of ovarian hperstimulation syndrome (OHSS). Estradiol level has an important role in the prediction of OHSS," Hum. Reprod. 18:1140-41.
The American College of Obstetricians and Gynecologists (2016). "Primary ovarian insufficiency in adolescents and young women," No. 605, Located at https://www.acog.org/Clinical-Guidance-and-Publicatlons/Committee-Opinions/Committee-on-Adolescent-Health-Care/Primary-Ovarian-Insufficiency-in-Adolescents-and-Young-Women, 5 total pages.

(Continued)

*Primary Examiner* — Christina M Borgeest
(74) *Attorney, Agent, or Firm* — Cooley LLP

(57) ABSTRACT

Further according to the present disclosure, there are methods for promoting egg maturation in assisted reproductive technologies, such as in in vitro fertilization (IVF) or in an embryo transfer (ET) process. There are also methods for decreasing the rate of ovarian hyperstimulation syndrome (OHSS), providing comparable or improved pregnancy rates, decreasing the time to pregnancy, and inhibiting premature ovulation. The methods include the step of administering a therapeutically effective amount of an active pharmaceutical ingredient of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof.

20 Claims, 13 Drawing Sheets

Specification includes a Sequence Listing.

(56) References Cited

OTHER PUBLICATIONS

American Pregnancy Association (2017). "Embryo transfer," Located at http://americanpregnancy.org/infertility/embryo-transfer/, 5 total pages.
Busso, C.E. et al. (2010). "Prevention of OHSS: Current strategies and new insights," Middle East Fertility Society 15:223-30.
Cakmak, H. et al. (2012). "Metaphase II (MII) oocytes obtained at different time points in the same in vitro fertilization cycle," J. Assist Reprod. Genet. 29:1203-05.
Casper, R.F. (2015). "Basic understanding of gonadotropin-releasing hormone-agonist triggering," Fertil. Steril. 103:867-69.
Chappell, N. et al. (2017). "The use of gonadotropin-releasing hormone antagonist post-ovulation trigger in ovarian hyperstimulation syndrome," Clin. Exp. Reprod. Med. 44:57-62.
Decourt, C. et al. (2016). "A synthetic kisspeptin analog that triggers ovulation and advances puberty," Sci. Rep. 6:26908, 10 total pages.
Devroey, P. et al. (2011). "An OHSS-Free Clinic by segmentation of IVF treatment," Human Reproduction 26:2593-97.
Dhillo, W.S. et al. (2007). "Kisspeptin-54 stimulates gonadotropin release most potently during the preovulatory phase of the menstrual cycle in women," J. Clin. Endocrinol. Metab. 92:3958-66.
Direito, A. et al. (2013). "Relationships between the luteinizing hormone surge and other characteristics of the menstrual cycle in normally ovulating women," Fertil. Steril. 99:279-85.
Esteves, S.C. (2015). "Principles and practices of individualization in OI/IUI," Presentation Slides, 72 total pages.
Fatemi, H.M. et al. (2014). "Severe ovarian hyperstimulation syndrome after gonadotropin-releasing hormone (GnRH) agonist trigger and "freeze-all" approach in GnRH antagonist protocol," Fertil. Steril. 101:1008-11.
Fauser, B.C. et al. (2002). "Endocrine profiles after triggering of final oocyte maturation with GnRH agonist after cotreatment with the GnRH antagonist ganirelix during ovarian hyperstimulation for in vitro fertilization," J. Clin. Endocrinol. Metab. 87:709-15.
FDA Definitions (2018). Located at https://www.fda.gov/ohrms/dockets/ac/03/briefing/3985B1_03_Definitions.htm, 4 total pages.
Fiedler, K. et al. (2012). "Predicting and preventing ovarian hyperstimulation syndrome (OHSS): the need for individualized not standardized treatment," Reprod. Biol. Endocrinol. 10:32, 10 total pages.
Gallos, I.D. et al. (2017). "Controlled ovarian stimulation protocols for assisted reproduction: A network meta-analysis (Protocol)," Cochrane Database of Systematic Reviews, Issue 3, pp. 1-23, 25 total pages.
Ghumman, S. (2015). "Freeze all" protocol—Has the debate concluded? Fertility Science & Research 2:90-4.
Griesinger, G. (2013). "Highlights of the annual congress of the ESHRE," Gynakologische Endokrinologie Springer Berlin Heidelberg 11(4):314-18 (with English translation), 15 total pages.
Gurbuz, A.S. et al. (2014). "Gonadotrophin-releasing hormone agonist trigger and freeze-all strategy does not prevent severe ovarian hyperstimulation syndrome: a report of three cases," Reprod. Biomed. Online 29:541-44.
Hoff, J.D. (1983). Hormonal dynamics at midcycle: a revaluation. J Clin Endocrinol Metab 57, 792-96.
Hosseini, M.A. et al. (2012). "Treatment of ovarian hyperstimulation syndrome using gonadotropin releasing hormone antagonist: a pilot study," Gynecol. Endocrinol. 28:853-55.
Humaidan, P. et al. (2011). "GnRH agonist for triggering of final oocyte maturation: time fora change of practice?" Human Reproduction Update 17:510-24.
Humaidan, P. et al. (2015). "Luteal phase supplementation after gonadotropin-releasing hormone agonist trigger in fresh embryo transfer: the American versus European approaches," Fertil. Steril. 1103:879-85.
International Search Report dated Jan. 15, 2018, for PCT Application No. PCT/EP2017/074800, filed on Sep. 29, 2017, 5 pages.
Jakimiuk, A.J. et al. (2017). "High levels of soluble vascular endothelial growth factor receptor 1/sFlt1 and low levels of vascular endothelial growth factor in follicular fluid on the day of oocyte retrieval correlate with ovarian hyperstimulation syndrom regardless of the stimulation protocol," J. Physiol. Pharmacol. 68:477-84.
Jayasena, C.N, et al. (2011). "The effects of Kisspeptin-10 on reproductive hormone release show sexual dimorphism in humans," J. Clin. Endocrinol. Metab. 96:E1963-E1972.
Jayasena, C.N. et al. (2014). "Kisspeptin-54 triggers egg maturation in women undergoing in vitro fertilization," J. Clin. Invest. 124:3667-3677.
Kauffman, A.S. and Smith, J.T. et al., eds. (2013). Kisspeptin signaling in reproductive biology, Springer Science+Business Media, LLC, 514 pages.
Lainas, G.T. et al. (2014). "Serum vascular endothellal growth factor levels following luteal gonadotrophin-releasing hormone antagonist administration in women with severe early ovarian hyperstimulation syndrome," BJOG 121:848-55.
Lentz, G.M. et al. (2012). "Reproductive endocrinology: Neuroendocrinology, gonadotropins, sex steroids, prostaglandins, ovulation, menstruation, hormone assay," Comprehensive Gynecology, $6^{th}$ edition, Presentation Slides, 17 total pages.
Leth-Moller, K. et al. (2014). "The luteal phase after GnRHa trigger-understanding an enigma," Int. J. Fertil. Steril. 8:227-34.
Ling, L.P. et al. (2014). "GnRH agonist trigger and ovarian hyperstimulation syndrome: relook at 'freeze-all strategy,'" Reprod. Biomed. Online 29:392-94.
Matsui, H. et al. (2014). "Effects and therapeutic potentials of kisspeptin analogs: regulation of the hypothalamic-pituitary-gonadal axis," Neuroendocrinology 99:49-60.
Medicinenet.com (2018). "Premature ovarian failure POF center—Primary ovarian insufficiency (POF, premature ovarian failure, POI)," located at https://www.medicinenet.com/premature_ovarian_failure_pof/article.htm, 14 total pages.
Medscape.Org (2011). "Luteal phase progesterone support in ART/IVF," Luk, J. et al., located at http://www.medscape.org/viewarticle/753218, 5 total pages.
Morris, R.S. (2016). "Premature ovarian failure and infertility, IVF1," located at http://www.ivf1.com/ovarian-failure/, 4 total pages.
Non-Final Office Action dated Apr. 30, 2020, for U.S. Appl. No. 16/369,847, filed Mar. 29, 2019, 12 pages.
Notice of Allowance dated Jan. 25, 2021, for U.S. Appl. No. 16/369,847, filed Mar. 29, 2019, 10 pages.
Orvieto, R. (2015). "Triggering final follicular maturation—hCG, GnRH-agonist or both, when and to whom?" J. Ovarian Res. 8:60, 6 total pages.
Ovidrel® Label (2000). Located at https://www.accessdata.fda.gov/drugsatfda_docs/label/2000/21149lbl.pdf, 27 total pages.
Papanikolaou, E.G. et al. (2006). "Incidence and prediction of ovarian hyperstimulation syndrome in women undergoing gonadotropin-releasing hormone antagonist in vitro fertilization cycles," Fertil. Steril. 85:112-20.
Papanikolaou, E.G. et al. (2018). "A proof-of-concept clinical trial of a single luteal use of long-acting gonadotropin-releasing hormone antagonist degarelix in controlled ovarian stimulation for in vitro fertilization: Long antagonist protocol," Frontiers in Endocrinology 9:1-7.
Park, S.J. et al. (2007). "Characteristics of the urinary luteinizing hormone surge in young ovulatory women," Fertil. Steril. 88:684-90.
Pau, E. et al. (2006). "Plasma levels of soluble vascular endothelial growth factor receptor-1 may determine the onset of early and late ovarian hyperstimulation syndrome," Hum. Reprod. 21:1453-60.
Rahayu, L.P. et al. (2017). "Effect of investigational kisspeptin/metastin analog, TAK-683, on luteinizing hormone secretion at different stages of the luteal phase in goats," J. Reprod. and Development 63:221-26.
Riddle, D.L. et al. (1997). "C. elegans II,"$2^{nd}$ edition. Section IX: Oocyte development, maturation and ovulation, Cold Spring Harbor Laboratory Press, 3 total pages.
Shah, D. et al. (2013). "Luteal insufficiency in first trimester," Indian J. Endocrinol. Metab. 17:44-9.
Smith, V. et al. (2015). "Prevention of ovarian hyperstimulation syndrome: A review," Obstet. Gynecol. Int. 2015:514159, 10 total pages.

(56) References Cited

OTHER PUBLICATIONS

Takeda Press Release (2016). "Roivant sciences and Takeda launch Myovant Sciences to development innovative therapeutics for women's health and prostate cancer," located at https://www.takeda.com/newsroom/newsreleases/2016/roivant-sciences-and-takeda-launch-myovant-sciences-to-develop-innovative-therapeutics-for-womens-health-and-prostate-cancer/, 5 total pages.

Thomsen, L. et al. (2015). "Ovarian hyperstimulation syndrome in the 21st century: the role of gonadotropin-releasing hormone agonist trigger and kisspeptin," Curr. Opin. Obstet. Gynecol. 27:210-14.

Türkgeldi, E. et al. (2015). "Gonadotropin-releasing hormone agonist triggering of oocyte maturation in assisted reproductive technology cycles," Turk. J. Obstet. Gynecol. 12:96-101.

Vaisbuch, E. et al. (2014). "Luteal-phase support in assisted reproduction treatment: real-life practices reported worldwide by an updated website-based survey," Reprod. Biomed. Online 28:330-35.

Wang, W. et al. (2011). "The time interval between hCG priming and oocyte retrieval in ART program: a meta-anaiysis," J. Assist Reprod. Genet. 28:901-10.

Whitlock, B.K. et al. (2015). "Kisspeptin receptor agonist (FTM080) increased plasma concentrations of luteinizing hormone in anestrous ewes," PeerJ, pp. 1-12.

Written Opinion of the International Searching Authority dated Jan. 15, 2018, for PCT Application No. PCT/EP2017/074800, filed on Sep. 29, 2017, 10 pages.

Your IVF Journey (2016). "Implantation after IVF: 10 crucial tips," Located at http://www.yourivfjourney.com/implantation-after-ivf-10-crucial-tips/, 18 total pages.

Zhai, J. et al. (2017). "Kisspeptin-10 inhibits OHSS by suppressing VEGF section," Society for Reproduction and Fertility, pp. 1-27.

U.S. Appl. No. 17/937,110, filed Sep. 30, 2022, by Rajasekhar et al. (Copy not attached).

\* cited by examiner

Arrows indicates dose administered.
Plasma concentrations on Days 2, 4, 6, 8, 10, 12, and 14 are predose values.

Mean Plasma Concentration-Time Curves by Dose Group: Day 1 up to 12 Hours

Mean Plasma Concentration-Time Curves by Dose Group:
Month 1, Day 2 Through Month 3

Mean (SD) Serum LH Concentrations Following a Single SC Bolus of API-MA

Mean (SD) Serum FSH Concentrations Following a Single SC Bolus of API-MA

Mean Serum Concentration-Time Profiles of LH

Mean Serum Concentration-Time Profiles of FSH

Mean Serum Concentration of LH Following API-MA Administered by SC Bolus (Day 1) and Continuous SC INF (Days 2-14)

Note: LLOQ=0.1 mIU/mL.

Mean Serum Concentration of FSH Following API-MA Administered by SC Bolus (Day 1) and Continuous SC INF (Days 2-14)

Note: LLOQ=0.1 mIU/mL.

LH by Subject (N=3) in the API-MA 0.5 mg/day Group

FSH by Subject (N=3) in the API-MA 0.5 mg/day Group (Mean ±SD)

(Mean ±SD)

METHODS OF TREATING FEMALE INFERTILITY

CROSS-REFERENCE TO RELATED APPLICATIONS

This application is a continuation application of U.S. patent application Ser. No. 16/369,847, filed Mar. 29, 2019, now issued U.S. Pat. No. 11,013,780, which is a continuation application of International Application No. PCT/EP2017/074800, filed Sep. 29, 2017, which claims the benefit of U.S. Provisional Application No. 62/402,018, filed Sep. 30, 2016; and U.S. Provisional Application No. 62/402,150, filed Sep. 30, 2016, the entireties of which are incorporated herein by reference.

REFERENCE TO A SEQUENCE LISTING

The Sequence Listing associated with this application is provided in text format in lieu of a paper copy, and is hereby incorporated by reference into the specification. The name of the text file containing the Sequence Listing is MYOV_017_02US_SeqList_ST25.txt. The text file is about 1 kilobyte, was created on Apr. 20, 2021, and is being submitted electronically via EFS-Web.

FIELD

The present disclosure is in the field of assistive reproductive technology (ART), and more specifically to methods and uses for performing ART in women who are at risk for OHSS and to methods and uses for promoting egg maturation, luteal phase support, and inhibiting premature ovulation.

BACKGROUND

Approximately 1.5 million assisted reproduction cycles are performed each year worldwide. Further, approximately 25% of women suffering from infertility have problems achieving ovulation, including the inability to produce fully-matured eggs (also referred to as oocytes) or the failure to ovulate. Fertility specialists assist reproduction by using a group of medications to temporarily correct ovulatory problems and to increase a woman's chance for pregnancy. Many assisted reproduction cycles include one or more of the following steps as part of the ultimate goal of pregnancy: (1) maturation of the ovarian follicles, which control the release of eggs in the ovaries; (2) prevention of premature ovulation; (3) triggering egg maturation at the appropriate time; (4) egg retrieval and fertilization; and (5) transplantation of fertilized egg followed by biochemical tests for pregnancy. However, other important ART regimens include oocyte banking or donation; menstrual cycle regulation, in which ovulation is allowed to occur after triggering (3) and then is followed by intrauterine insemination (IUI) or intercourse at a specified time. Also, for women with primary ovarian failure (e.g., women who are unable to bring an oocyte to maturity or ovulate even with ART), or as part of a surrogate procedure, embryo transfer (ET) with luteal phase support may be utilized, where the luteal phase support agent may be administered before, at the same time as, or after ET, or administered at one or more of the foregoing times.

Traditionally, ART protocols have used agents like follicle stimulating hormone (FSH) and human menopausal gonadotropin (hMG) during the initial stimulation phase, either preceded by administration of a gonadotropin-releasing hormone (GnRH) agonist (GnRH receptor agonist) or by the addition of a GnRH antagonist (GnRH receptor antagonist) to prevent (suppress) ovulation and prevent the release of premature oocytes due to a luteinizing hormone (LH) surge. Ovulation is suppressed so that eggs may mature and later be retrieved directly from the ovaries (instead of the fallopian tubes) and also to prevent high-order multiple gestation that may result from exposure of eggs to sperm in the fallopian tube if intercourse has occurred. Together, this stimulation process with FSH and a GnRH antagonist or agonist is called controlled ovarian stimulation (COS). Once the follicles have progressed to a pre-defined state, in which a number of oocytes are ready for final maturation, an oocyte maturation agent, or a so-called "trigger" agent (e.g., human chorionic gonadotropin hormone (hCG or HCG), a GnRH agonist, or both), is used to (1) promote final maturation and release of eggs from the ovary in preparation for intercourse or IUI, or (2) for final maturation and oocyte retrieval followed by ET to the uterus, for ART regimens that include an implantation step (e.g., in vitro fertilization (IVF)). Induction of final maturation of oocytes is a procedure that is usually performed as part of COS to render the oocytes fully developed, thereby resulting in a good yield of oocytes for retrieval and to optimal pregnancy chances. Thus, the trigger is essentially a replacement for the LH surge whose effects include final maturation of oocytes prior to ovulation in natural menstrual cycles. In cycles of IVF, final oocyte maturation triggering with a GnRH agonist instead of hCG decreases the risk of ovarian hyperstimulation syndrome (OHSS), but also decreases live-birth rates. In ART cycles followed by oocyte donation, use of GnRH agonists instead of hCG decreases the risk of OHSS with no evidence of a difference in live-birth rate. GnRH agonist and hCG triggered cycles of IVF afford similar oocyte yields and embryo quality.

After the trigger agent is administered, other agents (e.g., hCG and estradiol and progestins) are used to support the uterus (endometrium), so-called luteal phase support, in preparation for implantation. Luteal phase support is needed because after COS with gonadotropins, there is a defect due to supraphysiological steroid hormone concentrations inhibiting LH secretion via negative feedback at the level of the hypothalamic-pituitary-gonadal-axis. Due to the low LH levels, without luteal phase support, progesterone levels will drop, leading to a lower chance of successful implantation and therefore pregnancy.

Human chorionic gonadotropin (hCG) is used as a trigger due to its structural similarity to LH and ability to activate LH receptors and act as a trigger agent that results in significant quantities of mature oocytes. Due to the long half-life of hCG (24-36 hours) and ability to activate the LH receptors for seven to ten days, and sometimes even up to 16 days, hCG also provides luteal phase support, by increasing progesterone. Thus, hCG can be used in either the trigger (oocyte maturation) setting and/or for luteal phase support. Further, hCG-containing therapies as trigger agents are known to result in the production of significant quantities of mature oocytes. However, use of hCG in either setting is associated with the highest risk of OHSS. This raises safety concerns for women at high-risk of OHSS and possibly leads to a greater need to use segmentation freeze protocols (i.e., the cryopreservation of embryos followed by a frozen-thawed embryo transfer in a subsequent menstrual cycle) that may mitigate OHSS, but will delay ET and time to pregnancy. As discussed in more detail below, in OHSS, the ovaries may become enlarged, fluid may accumulate in the peritoneal cavity (ascites) and the patient may experience abdominal distension and pain, nausea, and diarrhea. Severe forms of OHSS may cause hemoconcentration, thrombosis, elevated white blood count, oliguria, renal failure, pleural effusion, respiratory distress, including acute respiratory distress syndrome, and even death.

Ovarian hyperstimulation syndrome (OHSS) is a significant complication (side effect) of ART. Ovarian hyperstimulation syndrome (OHSS) is thought to occur as a result of the supraphysiologic agonism of the LH receptors in the ovary that occur as a result of egg maturation triggered with human chorionic gonadotropin (acting directly on the ovarian LH receptors) and to a lesser extent the GnRH receptor agonists (triggering an endogenous LH surge that is higher than that observed in a normal cycle) in ovaries with a large number of mature follicles. The central feature of clinically significant OHSS is the development of vascular hyperpermeability causing shifts of fluid. The use of hCG causes the ovary to undergo extensive luteinization, where large amounts of estrogens, progesterone, and local cytokines are released. Exogenous hCG may have prolonged effects in vivo, and these are likely due to extended over-activation of LH receptors. Vascular endothelial growth factor (VEGF) production from follicles under the effect of hCG may increase vascular hyperpermeability underlying OHSS. Severe OHSS has been reported to occur in up to 2% of the general assisted reproductive population, and in up to 20% of patients at high-risk for developing OHSS, such as patients with polyscystic ovarian syndrome (PCOS).

The use of a GnRH agonist as a trigger agent is associated with lower rates of OHSS, but also results in lower pregnancy rates, especially without exogenously administered luteal phase support. Protocols using GnRH agonist triggers require the administration of agents for luteal phase support because the LH surge with these triggers is sharp (e.g., a peak with sufficient amplitude to trigger final maturation, but with a short wavelength) and short in duration (<20 hours or sometimes 24-36 hours). Further, circulating levels of progesterone and estradiol after a GnRH agonist trigger are significantly lower throughout the luteal phase as compared to those obtained after hCG triggering due to the shorter half-life of LH (~60 minutes) compared to hCG. Without exogenously administered luteal phase support after a GnRH agonist trigger, premature luteolysis and implantation failure are possible. Further, the risk of OHSS is not completely eliminated by using a GnRH agonist as a trigger agent and frozen embryo transfer in a subsequent menstrual cycle is still deemed safer to reduce the risk of OHSS. Further there is a desire for women undergoing ART to reduce the time to pregnancy, without increasing the risk of OHSS. Currently, it is difficult to provide the option of a fresh transfer while reducing the risk of OHSS and achieving desirable luteal phase support, oocyte maturation yield, pregnancy rates, and live birth rates.

With the need to improve both safety and efficacy, it is desirable to have new trigger agents for ART, as well as additional agents that may be administered for luteal phase support.

SUMMARY

The present disclosure relates to methods, uses, and compositions for helping women with infertility problems. In other aspects, the present disclosure relates to elevating levels of endogenous LH in a woman in need of such elevation. In some aspects, the present disclosure relates to luteal phase support that provides improved safety and efficacy for the ART process by offering an alternative to the current methods for the luteal phase support. The woman may be undergoing ART or may not be. One potential advantage of these improved methods and uses is that, for women undergoing ART, they may significantly reduce the risk of OHSS.

One aspect of the disclosure relates to a method of elevating endogenous LH level in a woman in need thereof, the method comprising administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide (herein referred to as Compound 1), or a corresponding amount of a pharmaceutically acceptable salt thereof, wherein the woman is undergoing ART and is at risk for OHSS, and wherein after the initial dose is administered, the woman's endogenous LH level in blood is elevated compared to the woman's endogenous LH level in blood prior to administration of the initial dose.

Another aspect of the disclosure relates to a method of increasing endogenous LH level in a woman in need thereof undergoing ART, the method comprising administering to the woman an initial dose of about 0.00003 mg to about 0.030 mg of Compound 1, or a corresponding amount of a pharmaceutically acceptable salt thereof,
wherein the woman is undergoing ART, and wherein at least 36 hours after the initial dose is administered, the woman's endogenous LH level in blood is elevated compared to the woman's endogenous LH level in blood prior to administration of the initial dose.

One aspect of the disclosure relates to a method of increasing endogenous LH level in a woman in need thereof undergoing ART, the method comprising administering to the woman an initial dose of about 0.00003 mg to about 0.030 mg of Compound 1, or a corresponding amount of a pharmaceutically acceptable salt thereof,
wherein the woman is undergoing ART, and wherein the maximum endogenous LH level in blood occurs at least about 12 hours after administration of the initial dose.

Another aspect of the disclosure relates to 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for use in a method of elevating endogenous LH level in a woman who is undergoing ART and who is at risk for OHSS, the method comprising administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of the pharmaceutically acceptable salt thereof.

One aspect of the disclosure relates to 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for use in a method of increasing endogenous LH level in a woman undergoing ART, the method comprising administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of the pharmaceutically acceptable salt thereof.

In certain embodiments of any of the foregoing or following, the maximum endogenous LH level in blood occurs between about 12 hours and about 48 hours after administration of the initial dose.

Another aspect of the disclosure relates to a method of increasing endogenous LH level in a woman undergoing ART and in need of luteal phase support, the method comprising administering to the woman an initial dose of about 0.00003 mg to about 0.030 mg of Compound 1, or a corresponding amount of a pharmaceutically acceptable salt thereof, after said woman has received a trigger dose of an oocyte maturation agent as part of an ART regimen.

In certain embodiments of any of the foregoing or following, the woman's endogenous LH level in blood is elevated between about 12 hours to about 96 hours after administration of the initial dose compared to the woman's endogenous LH level in blood prior to administration of the initial dose.

In certain embodiments of any of the foregoing or following, the woman's endogenous LH level in blood is elevated for at least 36 hours after administration of the initial dose compared to the woman's endogenous LH level in blood prior to administration of the initial dose. In some embodiments, the endogenous LH level in blood is elevated for about 36 hours to about 16 days or for about 36 hours to about 12 days.

In certain embodiments of any of the foregoing or following, the administration of the initial dose promotes oocyte maturation. In some embodiments, oocyte maturation occurs without the administration of exogenous hCG or exogenous LH. In other embodiments, oocyte maturation occurs after administration of a GnRH agonist or exogenous hCG. In some embodiments, the yield of mature oocytes is at least 50%.

In certain embodiments of any of the foregoing or following, after administration of the initial dose, the woman does not experience one or more symptoms selected from the group consisting of ascites, pleural effusion and reduced renal perfusion. In some embodiments, after administration of the initial dose, ovary size may not increase to greater than 5 cm in diameter.

In certain embodiments of any of the foregoing or following, the woman does not experience one or more symptoms of OHSS after administration of the initial dose. In some embodiments, after administration of the initial dose, the woman does not experience a worsening of one or more symptoms of OHSS.

In certain embodiments of any of the foregoing or following, the initial dose is administered when at least three ovarian follicles of at least 14 mm are visible via ultrasound or when at least three ovarian follicles of at least 18 mm are visible via ultrasound.

In certain embodiments of any of the foregoing or following, the initial dose is administered when serum estradiol concentration is at least 0.49 nmol/L.

In certain embodiments of any of the foregoing or following, the method or use further comprises administration of FSH about 5 days to about 12 days prior to administration of the initial dose.

In certain embodiments of any of the foregoing or following, the method or use further comprises administration of a GnRH antagonist about 2 days to about 10 days prior to administration of the initial dose. In some embodiments, the GnRH antagonist is selected from the group consisting of relugolix, elagolix, cetrorelix, ganirelix, abarelix, nal-blu, antide, azaline B, degarelix, D63153 (ozarelix), OBE2109, and teverelix. In some embodiments, the method or use further comprises administration of a GnRH agonist from about 14 to about 28 days prior to administration of the initial dose. In certain embodiments of any of the foregoing or following, the GnRH agonist is selected from the group consisting of leuprorelin acetate, gonadorelin, buserelin, triptorelin, goserelin, nafarelin, histrelin, deslorelin, meterelin, and lecirelin.

In certain embodiments of any of the foregoing or following, the initial dose is administered prior to oocyte retrieval, after oocyte retrieval, prior to ovulation, or after ovulation. In some embodiments, the initial dose is administered after administration of a GnRH agonist as an oocyte maturation agent.

In certain embodiments of any of the foregoing or following, wherein the method or use further comprises administering a second dose of about 0.00003 mg to about 0.030 mg of Compound 1, or a corresponding amount of a pharmaceutically acceptable salt thereof. In some embodiments, the second dose is administered within about 8 to about 60 hours after administration of the initial dose.

In certain embodiments of any of the foregoing or following, the method or use further comprises administering a third dose of about 0.00003 mg to about 0.030 mg of Compound 1, or a corresponding amount of a pharmaceutically acceptable salt thereof. In some embodiments, the third dose is administered within about 8 to about 60 hours after administration of the second dose.

In certain embodiments of any of the foregoing or following, the methods and uses further comprise administration of one to five additional doses of about 0.00003 mg to about 0.030 mg of Compound 1, or a corresponding amount of a pharmaceutically acceptable salt thereof. In some embodiments, the administration of the one to five additional doses is within about 8 to about 60 hours after the prior additional dose is administered. In some embodiments, one or more of the initial dose, second dose, third dose, or one to five additional doses promotes luteal phase support. In some embodiments, one or more of the initial dose, second dose, third dose, or one to five additional doses are administered via injection. In certain such embodiments, the injection is an intramuscular or subcutaneous injection. In certain embodiments of any of the foregoing or following, any one or more of the initial dose, second dose, third dose, or one to five additional doses is from about 0.0003 mg to about 0.03 mg.

In certain embodiments of any of the foregoing or following, the method or use further comprises administering one or more doses of a progestogen. In certain embodiments of any of the foregoing or following, the method or use does not comprise administering one or more doses of a progestogen.

In certain embodiments of any of the foregoing or following, the method or use further comprises oocyte retrieval.

In certain embodiments of any of the foregoing or following, the woman's pituitary is desensitized to GnRH prior to administration of the initial dose.

In certain embodiments of any of the foregoing or following, the method or use further comprises implantation of an embryo. In some embodiments, the implantation occurs within about 2 to about 10 days after administration of the initial dose. In some embodiments, the implantation occurs within about 1 to about 7 days after oocyte retrieval. In some embodiments, the embryo has not been frozen. In some embodiments, the embryo is implanted within the same menstrual cycle as oocyte retrieval.

In certain embodiments of any of the foregoing or following, the method or use induces ovulation.

In certain embodiments of any of the foregoing or following, the woman conceives via intercourse or IUI after administration of at least the initial dose. In some embodiments, after administration of at least the initial dose, the woman conceives and/or gives birth.

In certain embodiments of any of the foregoing or following, the woman is undergoing COS. In some embodiments, the woman has one or more of PCOS, serum anti-Müllerian hormone (AMH) greater than 15 pmol/L, total antral follicle count (AFC) greater than 23 via ultrasound, serum estradiol E2 greater than 3000 pg/mL, or has experienced one or more previous episodes of OHSS. In some embodiments, the woman is any one or more of anovulatory, or of advanced maternal age, or is experiencing secondary ovarian failure, oligomenorrhea, amenorrhea, endometriosis, or PCOS.

In certain embodiments of any of the foregoing or following, the ART therapy is selected from the group consisting of oocyte donation, oocyte banking, intracytoplasmic sperm injection (ICSI), IVF, embryo transfer (ET) process, ovulation induction, and IUI.

One aspect of the disclosure relates to a method of inducing final follicular maturation and early luteinization in a woman in need thereof, wherein said woman is undergoing ART, has undergone pituitary desensitization and has been pretreated with follicle stimulating hormones as part of ART, said method comprising administering to the woman an initial dose of about 0.00003 mg to about 0.030 mg of Compound 1, or a corresponding amount of a pharmaceutically acceptable salt thereof, and wherein after the initial dose is administered, the woman's endogenous LH level in blood is elevated compared to the woman's endogenous LH level in blood prior to administration of the initial dose.

Another aspect of the disclosure relates to a method of inducing ovulation in a woman in need thereof, wherein said woman is anovulatory infertile and wherein said infertility is not due to primary ovarian failure, said method comprising administering to the woman an initial dose of about 0.00003 mg to about 0.030 mg of Compound 1, or a corresponding amount of a pharmaceutically acceptable salt thereof, and wherein after the initial dose is administered, the woman's endogenous LH level in blood is elevated compared to the woman's endogenous LH level in blood prior to administration of the initial dose.

Another aspect of the disclosure relates to 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use in a method of inducing final follicular maturation and early luteinization in a woman who is undergoing ART, has undergone pituitary desensitization and has been pretreated with follicle stimulating hormones as part of ART, said method comprising administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of the pharmaceutically acceptable salt thereof.

One aspect of the disclosure relates to 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use in a method of inducing ovulation in a woman who is anovulatory infertile, wherein said infertility is not due to primary ovarian failure, said method comprising administering to the woman an initial dose of 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of the pharmaceutically acceptable salt thereof.

In certain embodiments of any of the foregoing or following, the woman is at risk for OHSS.

In certain embodiments of any of the foregoing or following, the woman experiences anovulatory infertility not due to primary ovarian failure.

In certain embodiments of any of the foregoing or following, the methods and uses comprise administering to the woman an initial dose of about 0.001 mg to about 0.003 mg, about 0.001 mg to about 0.030 mg, or about 0.0003 mg to about 0.003 mg of Compound 1, or a corresponding amount of a pharmaceutically acceptable salt thereof.

One aspect of the disclosure relates to use of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for the manufacture of a medicament for elevating endogenous LH level in a woman who is undergoing ART and who is at risk for OHSS.

Another aspect of the disclosure relates to use of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for the manufacture of a medicament for increasing endogenous LH level in a woman undergoing ART.

One aspect of the disclosure relates to use of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for the manufacture of a medicament for inducing final follicular maturation and early luteinization in a woman who is undergoing ART, has undergone pituitary desensitization and has been pretreated with follicle stimulating hormones as part of ART.

Another aspect of the disclosure relates to use of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for the manufacture of a medicament for inducing ovulation in a woman who is anovulatory infertile, wherein said infertility is not due to primary ovarian failure.

Further embodiments of the present disclosure are described hereinafter, in which some, but not all, embodiments of the disclosure are illustrated.

Each embodiment disclosed herein may be used individually or in combination with any other embodiment disclosed herein.

Publications, patents, and published patent applications referred to in this application are specifically incorporated by reference herein.

DETAILED DESCRIPTION

Assisted reproductive technology (ART) is complex, with each assisted reproduction cycle consisting of several, carefully orchestrated steps. If any of these steps are improperly performed, conception or pregnancy may fail. Additionally, the success of ART protocols varies greatly from woman to woman, adding to the complexity. The typical phases of ART include an initial COS phase to promote and stimulate the controlled growth and development of ovarian follicles, followed by the use of a so-called "trigger" agent to promote/induce the final maturation of oocytes. In some ART regimens, the mature oocytes may then be retrieved from the ovarian follicles, fertilized in vitro or by ICSI, and the embryo(s) transferred to the uterus or, instead of retrieving the eggs from the ovarian follicles, ovulation occurs and the mature oocytes may be fertilized via intercourse or IUI. A schematic of a representative ART regimen is provided in FIG. 1. As ART procedures are invasive, expensive, and may have negative side effects, preventing or reducing the possibility of conception failure or pregnancy failure is important.

Figure 1:
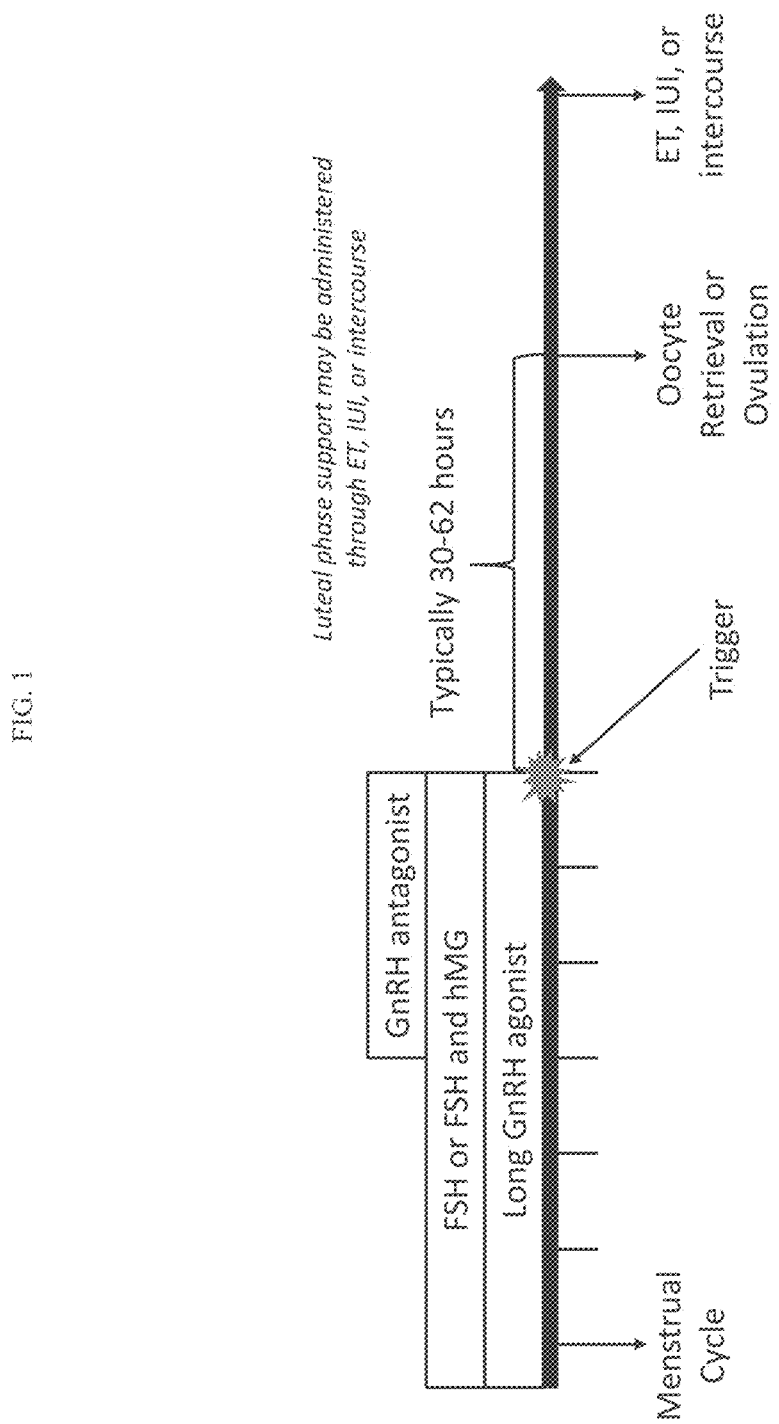
FIG. 1 shows an illustrative schematic of an ART protocol. This schematic is not meant to be limiting.

For example, as schematically depicted in FIG. 1, administration of long GnRH agonist treatment, to suppress the LH surge, begins in the menstrual cycle prior to the menstrual cycle in which the trigger agent will be administered. Administration of the GnRH agonist may be in combination with FSH or FSH/hMG treatment, to stimulate the follicles, or FSH or FSH/hMG treatment in the absence of long GnRH agonist treatment may begin the ART treatment protocol. Alternatively, a GnRH antagonist may be used instead of a GnRH agonist to suppress the LH surge and is used in combination with FSH or FSH/hMG treatment. In this case, the GnRH antagonist is administered within the same menstrual cycle and after FSH or combination FSH/hMG treatment has commenced. Treatment may then be followed by administration of a trigger, typically a GnRH agonist, hCG, or, as detailed in this disclosure, Compound 1, a metabolite thereof, or a pharmaceutically acceptable salt of any of the foregoing. Human chorionic gonadotropin (hCG) has LH-like activity which acts on LH receptors and causes ovulation. Typically 30 to 62 hours after administration of the trigger, oocyte retrieval or ovulation occurs. The human female subject undergoing ART may then be treated with IUI or have intercourse to become pregnant. After the trigger and through ET, IUI, or intercourse, the human female subject may or may not receive luteal phase support, including, but not limited to, administration of low dose hCG, a progestogen, estradiol, or Compound 1, a metabolite thereof, or a pharmaceutically acceptable salt of any of the foregoing.

Disclosed herein are ART methods and uses comprising administration of Compound 1, a metabolite thereof, or a pharmaceutically acceptable salt of any of the foregoing. As used herein, Compound 1 is 2-(N-Acetyl-D-tyrosyl-trans-4-hydroxy-L-prolyl-Lasparaginyl-L-threonyl-L-phenylalanyl)-hydrazinocarbonyl-L-leucyl-Nω-methyl-L-arginyl-L-tryptophanamide. Compound 2 is a metabolite of Compound 1. Compound 1, a metabolite thereof, or a pharmaceutically acceptable salt of any of the foregoing may mimic natural physiology by inducing the release of endogenous LH during assisted reproduction, thereby possibly enhancing the likelihood of successful egg (oocyte) maturation and, in some cases, ovulation at the right time during the cycle without the potential for serious side effects associated with current hormone-stimulation treatment options, such as hCG. Previous studies with Compound 1 were conducted in men or animals, such as rats, dogs, and monkeys, to assess Compound 1's pharmacokinetic properties or efficacy in the treatment of prostate cancer. The bioavailability of Compound 1 was quite different in rats (66.3%) versus dogs (92.4%). The enhancement of subcutaneous first-pass metabolism caused non-linear pharmacokinetics of Compound 1 after a single subcutaneous (SC) administration to rats. Compound 1 showed less than dose-proportional non-linear pharmacokinetics with a reduction of the AUC after SC administration in a dose range of 1 mg/kg and 10 mg/kg to rats. Less than dose-proportional non-linear pharmacokinetics were observed after SC administration with limited absorption of Compound 1 at the highest dose level contrary to the linear pharmacokinetics following IV dosing, indicating an enhancement of SC metabolism with dose escalation. The systemic absorption of Compound 1 recovered when protease inhibitors were subcutaneously co-administered, suggesting the involvement of SC proteases in the first-pass metabolism. The top human dose given to men via SC bolus was only approximately 0.008 mg/kg and exposure was dose proportional up to this dose. SC infusions were also proportional up to approximately 0.1 mg/kg. A depot formulation resulted in less than proportional exposure over approximately 0.1 mg/kg to 0.4 mg/kg. The present disclosure describes the use of Compound 1, a metabolite thereof, or a pharmaceutically acceptable salt of any of the foregoing, in women to assist with ART. The doses of Compound 1 used herein are much lower than those tested in rats and in men, with a maximum dose of 30 or 0.25 µg/kg compared to 1 mg/kg and 10 mg/kg in rats and 8 µg/kg and 0.1 mg/kg to 0.4 mg/kg in men.

Compound 1, a metabolite thereof, or a pharmaceutically acceptable salt of any of the foregoing, may not only facilitate the maturation, release (ovulation), and retrieval of fresh mature oocytes (or eggs, used interchangeably herein) from the ovaries, leading to similar or improved overall pregnancy rates versus an hCG trigger, but also, may significantly mitigate the risk of key side effects, like OHSS, compared to hCG and GnRH agonists. Additionally, compared to currently available trigger agents (particularly, hCG-based trigger agents), Compound 1, a metabolite thereof, or a pharmaceutically acceptable salt of the foregoing, may provide an advantage of significantly reducing the rate of OHSS in all patients, including those with elevated levels of AMH or patients with FSH and LH receptor mutation sensitivity. Further, Compound 1, a metabolite thereof, or a pharmaceutically acceptable salt of any of the foregoing, may provide luteal phase support by activating the LH surge to a natural peak and with a long duration (>20 hours) mimicking the natural LH surge of 48 hours) with a low risk of OHSS. This benefit of Compound 1, a metabolite thereof, or a pharmaceutically acceptable salt of any of the foregoing, may eliminate the need for additional luteal phase support, such as daily IM progesterone injections or additional hCG supplementation, simplifying ART protocols and also allowing for the implantation of "fresh" embryos during the same menstrual cycle, potentially reducing the time to pregnancy.

Compared to currently available trigger agents, Compound 1, a metabolite thereof, or a pharmaceutically acceptable salt of any of the foregoing, may provide an advantage of shorter time to pregnancy. Compound 1, a metabolite thereof, or a pharmaceutically acceptable salt of any of the foregoing, may afford increased rates of fresh embryo transfer, reducing the need for segmentation (freezing the egg or embryo between retrieval and implantation). Due to the mode of action of Compound 1, a metabolite thereof, or a pharmaceutically acceptable salt of any of the foregoing, there may be less negative impact on the endometrium compared to current treatments. Thus, the endometrium may be ready for implantation (higher endometrial receptivity) immediately after egg (oocyte) retrieval. This may allow for implantation within the same menstrual cycle as triggering and oocyte retrieval. Compared to hCG-based trigger agents (including dual triggers with GnRH agonists), Compound 1, a metabolite thereof, or a pharmaceutically acceptable salt of any of the foregoing, may result in less need for a segmentation freezing protocol, thereby reducing the number of IVF cycles; shortening time to pregnancy, while maintaining acceptable pregnancy rates; lowering costs; and reducing side effects, such as macrosomia (large for gestational age), placenta accreta, and preeclampsia, all with significantly lower OHSS rates. Compound 1, a metabolite thereof, or a pharmaceutically acceptable salt of any of the foregoing, may provide safety and efficacy attributes that represent an advantage compared to current treatments that require segmentation.

The present disclosure also relates to methods and uses comprising administration of Compound 1, a metabolite thereof, or a pharmaceutically acceptable salt of any of the foregoing, for increasing endogenous LH levels in a human female subject undergoing ART, such as in IVF, ICSI, oocyte donation and banking, regulation of a menstrual cycle so a human female subject may conceive via intercourse or IUI, ovulation induction, and/or in an ET process. An increase in endogenous LH levels may assist in both oocyte maturation and luteal phase support.

The present disclosure further relates to methods and uses comprising administration of Compound 1, a metabolite thereof, or a pharmaceutically acceptable salt of any of the foregoing, for inhibiting ovulation and the premature release of oocytes during the initial COS phase. These methods and uses may be applicable to ART protocols that utilize either a gonadotropin-releasing hormone (GnRH) agonist or antagonist during the initial COS phase.

Provided herein is the use of Compound 1, a metabolite thereof, or a pharmaceutically acceptable salt of any of the foregoing, for the manufacture of a medicament for treatment according to any of methods described herein. Provided also is Compound 1, a metabolite thereof, or a pharmaceutically acceptable salt of any of the foregoing, for use in any of the methods described herein.

Compounds of the Disclosure

As used herein, Compound 1 is 2-(N-Acetyl-D-tyrosyl-trans-4-hydroxy-L-prolyl-L-asparaginyl-L-threonyl-L-phenylalanyl)-hydrazinocarbonyl-L-leucyl-Nω-methyl-L-arginyl-L- tryptophanamide. The molecular formula is $C_{58}H_{80}N_{26}O_{14}$ and the molecular weight is 1225.35. Compound 1 is a free form and represented by the sequence:

Ac-D-Tyr-Hyp-Asn-Thr-Phe-AzaGly-Leu-Arg(Me)-Trp-NH2 (SEQ ID NO. 1), and by the structural formula:

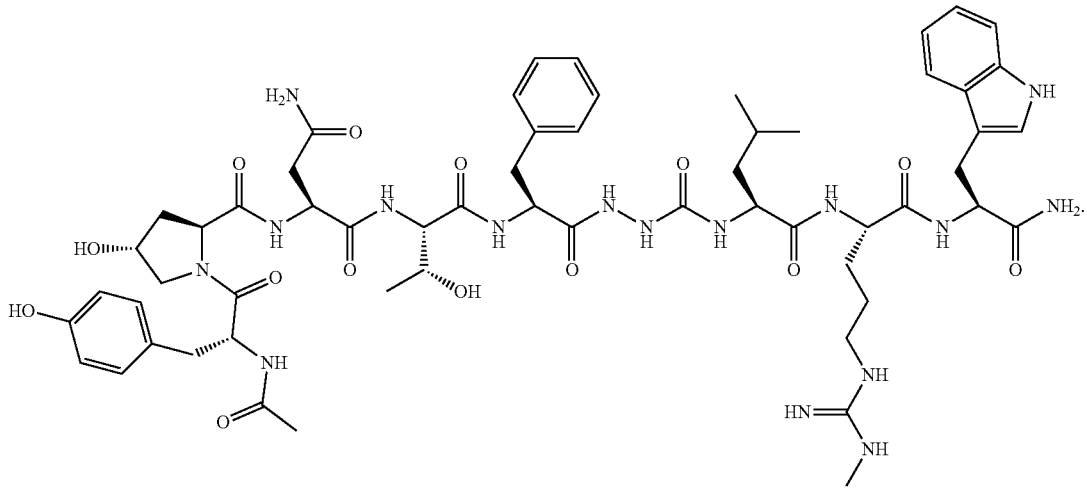 [SMILES: CNC(=N)NCCC[C@H](NC(=O)[C@H](CC(C)C)NC(=O)NNC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O]

In some embodiments, the compound of the disclosure is a metabolite of Compound 1. In certain such embodiments, the metabolite is Compound 2, represented by the following structural formula:

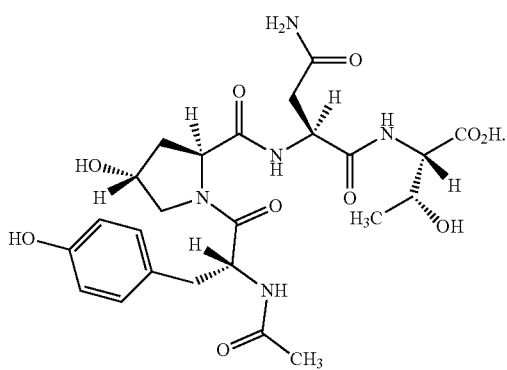 [SMILES: CC(=O)N[C@H](Cc1ccc(O)cc1)C(=O)N1C[C@H](O)C[C@H]1C(=O)N[C@@H](CC(N)=O)C(=O)N[C@H](C(=O)O)[C@@H](C)O]

In some embodiments, a pharmaceutically acceptable salt of Compound 1 and/or a metabolite thereof is used. "Physiologically acceptable," "pharmaceutically acceptable," or "pharmacologically acceptable" compounds and compositions may include materials which are not biologically, or otherwise, undesirable. For example, the material may be administered to an individual without causing any substantially undesirable biological effects or interacting in a deleterious manner with any of the components of the composition in which it is contained. In certain embodiments, the pharmaceutically acceptable salt of Compound 1 and/or a metabolite thereof is a pharmaceutically acceptable acid addition salt. Such salts include, but are not limited to, salts with inorganic acids (e.g., hydrochloric acid, hydrobromic acid, nitric acid, sulfuric acid, phosphoric acid, and the like) and salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like). In certain embodiments, the pharmaceutically acceptable salt of Compound 1 and/or a metabolite thereof is a pharmaceutically acceptable basic addition salt. Such salts include, but are not limited to, an inorganic base (e.g., alkali metals and alkaline earth metals such as sodium, potassium, calcium, magnesium, ammonia, and the like) or an organic base (e.g., trimethylamine, triethylamine, pyridine, picoline, ethanolamine, diethanolamine, triethanolamine, dicyclohexylamine, N,N'-dibenzylethylenediamine, and the like).

As used herein, a form of Compound 1 is 2-(N-Acetyl-D-tyrosyl-trans-4-hydroxy-L-prolyl-L-asparaginyl-L-threonyl-L-phenylalanyl)-hydrazinocarbonyl-L-leucyl-Nω-methyl-L- arginyl-L-tryptophanamide monoacetate. For the monoacetate salt, the molecular formula is $C_{58}H_{80}N_{16}O_{14} \cdot C_2H_4O_2$ and the molecular weight is 1285.41. The structural formula is the following:

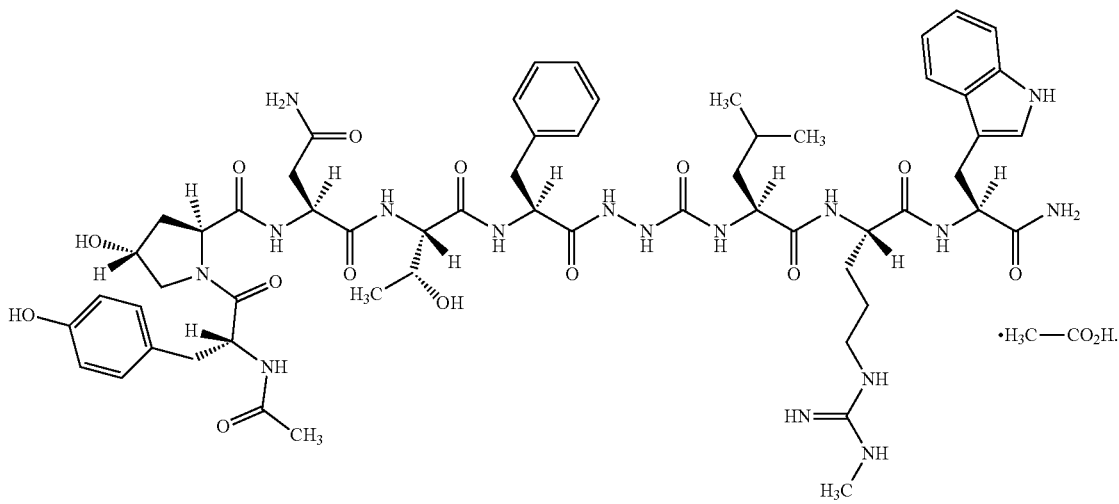

Throughout the present disclosure, amounts of Compound 1, or a metabolite thereof, refer to the amount of Compound 1 free form present in the formulation. The term "corresponding amount" as used herein refers to the amount of a pharmaceutically acceptable salt of Compound 1, or a metabolite thereof, required to obtain the amount of Compound 1, or a metabolite thereof, free form recited in the formulation. It would be clear to one of skill in the art how to calculate the "corresponding amount" of the salt of a compound, such as the corresponding amount of the pharmaceutically acceptable salt of Compound 1, taking into account the difference in molecular weight between the free form of a compound and a salt form. For example, 10.0 mg of compound free form, would correspond to 10.5 mg of the monoacetate salt.

Compound 1, or a pharmaceutically acceptable salt thereof, and pharmaceutical compositions containing Compound 1, or a pharmaceutically acceptable salt thereof, may be produced by methods described in U.S. Pat. Nos. 7,960,348 and 8,404,643, the disclosures of which are herein incorporated by reference.

Compound 1 has been described as a kisspeptin analog. Kisspeptin, a hypothalamic neuropeptide encoded by the KISS1 gene, is a central regulator of GnRH secretion and a recently discovered hormone which is vital for normal puberty. Kisspeptin is a peptide ligand agonist of the human G-protein-coupled receptor 54 (GPR54)/KISS1 receptor (KISS1R) (formerly known as OT7T175/GPR54). Mutations of or knock out of the KISS1R gene result in defective onset of puberty. In the hypothalamus, kisspeptin plays a key role in regulating the amount and pulsatility of gonadotropin-releasing hormone (GnRH) secretion. Administration of kisspeptin in mammals, including humans, induces GnRH and gonadotropin release, and this effect is most plausibly a direct effect of the peptide on the GnRH neurons. GnRH is the key component of the hypothalamic-pituitary-gonadal axis and controls the reproductive functions, such as spermatogenesis, follicular maturation and ovulation, and steroidogenesis. Therefore, kisspeptin is a critical regulator of the hypothalamic-pituitary-gonadal axis via controlling GnRH neurons. There are two modes of GnRH secretion. One mode is pulsatile GnRH secretion that mainly regulates spermatogenesis, folliculogenesis, and steroidogenesis, which is feedback (negatively) regulated by steroidal hormones. The other mode is GnRH surge, resulting in an LH surge that is observed in females only, and induces final maturation of oocytes and, eventually, ovulation. Kisspeptin neurons in the hypothalamus can regulate both modes of GnRH secretion. Pharmacologically, in multiple species, including humans, acute kisspeptin exposure may stimulate GnRH-gonadotropin secretion, whereas chronic (higher dose) kisspeptin exposure may suppress GnRH secretion and the hypothalamic-pituitary-gonadal-axis due to potential mechanisms of suppression, such as desensitization of GnRH receptors and/or depletion of GnRH reserves. Chronic administration of kisspeptin analogs suppresses intrinsic GnRH pulses and downstream pituitary gonadal functions. This may be due to the attenuation of the responsiveness of GnRH neurons to endogenous kisspeptin stimulation and the stimulation of GnRH neurons to release low levels of GnRH continuously.

Kisspeptin-54 has a half-life of 32 minutes and it stimulates the release of endogenous GnRH, which then stimulates gonadotropin release and subsequently sex hormones. Kisspeptin administration to healthy human male and female volunteers was shown to significantly increase plasma LH, FSH, and testosterone concentrations, and subcutaneous administration of kisspeptin to human female volunteers increased plasma LH in all phases of the menstrual cycle. The effect of kisspeptin was greatest in the pre-ovulatory phase, when trigger agents are typically administered, and least in the follicular phase of the cycle. Kisspeptin was also experimentally tried as a trigger in an ART protocol comprising a GnRH antagonist and FSH in both an IVF population of women and a high risk OHSS IVF population. Kisspeptin has only been used as a trigger in ART cycles using a GnRH antagonist protocol. Accordingly, an increased luteal phase defect may occur with kisspeptin ART protocols as GnRH antagonist protocols typically result in luteal phase defects when hCG is not the trigger. Kisspeptin was found to stimulate endogenous levels of LH, however, the duration of the LH surge was much shorter than the surge observed with hCG or GnRH agonist triggers, leading to the need for additional exogenous luteal phase support. With kisspeptin-54, the LH surge resolved by 36 hours. In some women, the full LH surge was not observed, thereby reducing oocyte yields. Further, higher doses of kisspeptin led to lower pregnancy rates and the ideal dose is not yet known.

Additional studies reported in Example 11 (FIGS. 15A and 16A) indicate that female subjects receiving kisspeptin-54 during the follicular phase (when LH levels are least affected by trigger agents) experienced an increase in LH peaking around 4-6 hours after administration of the kisspeptin trigger, with the LH surge lasting less than 14 hours. Despite its drawbacks, studies with kisspeptin-54 did indicate that fresh embryo transfer (transfer within the same menstrual cycle) is possible in high risk OHSS women.

Compound 1, or a pharmaceutically acceptable salt thereof, has a half-life of up to four hours. As shown in Example 11 (FIGS. 16B, 17, and 18), after administration of a 0.003 nmol/kg Compound 1 (approximately 0.00022 mg) dose during the follicular phase in women (when LH levels are least affected by trigger agents), peak serum LH levels are estimated to occur between 14-36 hours post-dosing and the LH surge lasted at least about 48 hours, the duration of the natural LH surge. Thus, administration of Compound 1, or a pharmaceutically acceptable salt thereof, may potentially be able to not only trigger final oocyte maturation, but also able to provide luteal support and, therefore, enhance the likelihood of successful implantation. Surprisingly, the LH surge observed with Compound 1 had a curve similar to that of the natural LH surge, being broader than the LH surges induced by GnRH agonist triggers, and potentially longer lasting. It was also surprising that Compound 1 had such a robust impact on LH levels during the follicular phase in women. As its impact was greater than that of kisspeptin-54, this indicates that Compound 1 should also cause a dramatic increase in LH levels during the pre-ovulatory phase, potentially greater both in amplitude and duration than those observed with kisspeptin-54 during the pre-ovulatory phase. As used herein, the pre-ovulatory phase may refer to the time period 15 to 16 days before the start of a woman's next predicted period.

Due to the nature of the LH surge observed with Compound 1, which more closely mimics the natural surge, it, or a metabolite thereof, may be an ideal agent for inclusion into ART protocols. Administration of Compound 1, a metabolite thereof, or a pharmaceutically acceptable salt of any of the foregoing, as a trigger could limit the need for luteal phase support. It could also allow for the option of fresh transfer of embryos, greatly shortening the time to pregnancy and the costs associated with multiple rounds of ART.

An additional advantage of Compound 1, a metabolite thereof, or a pharmaceutically acceptable salt of any of the foregoing, over current treatments is that its effects will depend upon the endogenous release of a woman's GnRH pool. This may result in a more physiologic stimulation of gonadotropins and prevent excessive stimulation, which limits current fertility treatments. As Compound 1, or a metabolite thereof, stimulates the release of endogenous LH into the woman's circulation, there is far less likelihood of potentially life-threatening OHSS.

Methods of Treatment and Uses of the Compounds of the Disclosure

The present disclosure provides for methods and uses for elevating endogenous LH level in a woman in need thereof comprising administering to the woman an initial dose of Compound 1, a metabolite thereof, or a pharmaceutically acceptable salt of any of the foregoing. In some embodiments, the woman is undergoing ART and is at risk for OHSS. In certain such embodiments, after the initial dose is administered, the woman's endogenous LH level in blood is elevated compared to the woman's endogenous LH level in blood prior to administration of the initial dose.

Throughout the disclosure, the doses or amounts of Compound 1, a metabolite thereof, or a pharmaceutically acceptable salt of any of the foregoing (for example, about 0.00003 mg to about 0.030 mg, about 0.0003 to about 0.003 mg, about 0.001 mg to about 0.003 mg, or about 0.001 mg to about 0.03 mg of Compound 1, or a corresponding amount of a pharmaceutically acceptable salt thereof), used in any of the methods or uses disclosed herein may be any of the doses or amounts disclosed herein below. Additionally, the formulations or pharmaceutical compositions comprising Compound 1, a metabolite thereof, or a pharmaceutically acceptable salt of any of the foregoing, used in any of the methods and uses disclosed herein may be any of the formulations or pharmaceutical compositions disclosed herein below. The doses and amounts of Compound 1, a metabolite thereof, or a pharmaceutically acceptable salt of any of the foregoing, and formulations or pharmaceutical compositions comprising Compound 1, a metabolite thereof, or a pharmaceutically acceptable salt of any of the foregoing, disclosed herein may be administered by any of the methods of administration disclosed herein.

Herein, the woman's endogenous LH level in blood prior to administration of the initial dose may be computed as the mean of five LH values immediately preceding the designated day of onset of the LH surge (i.e., 5 days preceding administration of Compound 1, a metabolite thereof, or a pharmaceutically acceptable salt of any of the foregoing). Elevating would be an increase above the woman's endogenous LH level in blood prior to administration of the initial dose. The end of elevation would be when the LH levels returns to the woman's endogenous LH level in blood prior to administration of the initial dose. As used herein, the LH peak is the highest LH value, the LH amplitude is the difference between the peak LH value and the woman's endogenous LH value in blood prior to administration of the initial dose, and the LH surge fold increase is the peak LH value divided by the woman's endogenous LH value in blood prior to administration of the initial dose. In the setting of COS, the woman's endogenous LH value in blood prior to administration of the initial dose ranges from 2-10 IU/L, with a peak range of LH surge between 20 to 120 IU/L, (Amplitude=peak−the woman's endogenous LH level in blood prior to administration of the initial dose). The fold increase is typically between 2 times and 60 times. In most women, a 2 times to 11 times fold increase in LH is expected (when done in COS setting or pre-ovulatory phase).

As will be appreciated by the skilled artisan, the success of ART regimens may depend on both the timing and dosage of administration of various agents throughout the treatment regimen and during various phases of a woman's menstrual cycle. As described herein, the various regimen depend on careful administration of agents including FSH or FSH/hMG to induce oocyte maturation and also the administration of additional agents (e.g., GnRH agonists or antagonists) at specific times during the menstrual cycle and in certain doses to ensure that multiple oocytes are maturing within a similar period such that after the administration of the trigger agent, oocytes that have undergone final maturation are available for retrieval before premature ovulation for use in e.g., oocyte banking, oocyte donation, IVF, ICSI, etc., or are allowed to ovulate and are subsequently fertilized by IUI or intercourse within a specified time after projected ovulation. Important to all of these aspects of ART is the control of LH levels. For example, there must be enough LH present to stimulate ("trigger") final maturation of multiple oocytes within a given time period and in sufficient quantity to result in oocyte yield high enough for successful oocyte retrieval (e.g., sufficient oocyte yield) and therefore available for ICSI or IVF. Additionally, where ET is contemplated, particularly within the same menstrual cycle, there needs to be an elevated level of LH sufficient to continue production of progesterone from the corpus luteum to help ensure support of the endometrium (also referred to as luteal support) and thereby enhance the likelihood of successful implantation of the embryo, thus leading to successful pregnancy and live birth. Similarly, where ovulation takes place followed by IUI or intercourse, luteal support and a receptive endometrium are also important for the same reasons. Based on control of the timing of administration and dose administered of Compound 1, a metabolite thereof, or a pharmaceutically acceptable salt of any of the foregoing, in order to increase a woman's endogenous LH levels at the right amount and at the right time, Compound 1, a metabolite thereof, or a pharmaceutically acceptable salt of any of the foregoing, may be safely employed in various ART regimens described herein. As described herein, the use of Compound 1, a metabolite thereof, or a pharmaceutically acceptable salt of any of the foregoing, elevates the endogenous LH level in blood. As the source of the LH is the woman's own pituitary gland, instead of exogenous LH or an agent that agonizes the LH receptor, the risk of stimulating supraphysiological amounts of LH (e.g., overstimulating) that may lead to OHSS or other complications is greatly reduced, while also allowing for high oocyte yield at oocyte retrieval and supporting successful implantation during ET.

The present disclosure includes methods and uses comprising administration of Compound 1, a metabolite thereof, or a pharmaceutically acceptable salt of any of the foregoing, in assisted reproductive technologies, such as IVF, ICSI, oocyte donation and banking, regulation of a menstrual cycle so a human female subject may conceive via intercourse or intrauterine insemination (IUI), ovulation induction, and/or in an ET process.

As used herein, "in vitro fertilization" (IVF) may refer to a method comprising collecting an ovum, fertilizing the ovum in vitro with a spermatozoon and, when cleavage has progressed to a certain degree, inserting the ovum into the uterine cavity. That is, it may include the processes of ovulation induction, ovum collection, IVF and culture, and embryo transfer. In IVF, induction of final maturation may allow for egg (oocyte) retrieval when the eggs (oocytes) are fully mature. Further, in IVF, final maturation induction may be preceded by COS.

"Embryo transfer" may refer to, within the IVF processes, the process of implanting an embryo in the uterine cavity. One to several embryos inserted into the uterine cavity may be implanted in the uterus, thereby possibly resulting in pregnancy. The term may also encompass frozen embryo transfer and gamete intrafallopian transfer (GIFT) that do not involve in vitro fertilization. "An embryo transfer process" may refer to the entire period during which insertion of an embryo or gamete into the uterine cavity, a sequence of processes of implantation of the embryo or gamete in the uterus and pregnancy, drug administration before and after embryo transfer to achieve pregnancy, and the like are performed.

"Intracytoplasmic sperm injection" (ICSI) may refer to the laboratory procedure where a single sperm is picked up with a fine glass needle and is injected directly into each egg. In conventional IVF, the eggs and sperm are mixed together in a dish and the sperm fertilizes the egg 'naturally.' However to have a chance that this will occur, large numbers of actively swimming normal sperm are required. For many couples, the number of suitable sperm available may be very limited or there may be other factors preventing fertilization, so conventional IVF is not an option, but ICSI is. ICSI refers to the laboratory procedure where a single sperm is picked up with a fine glass needle and is injected directly into each egg. This is carried out in the laboratory by experienced embryologists using specialist equipment. Very few sperm are required and the ability of the sperm to penetrate the egg is no longer important as this has been assisted by the ICSI technique. ICSI does not guarantee that fertilization will occur as the normal cellular events of fertilization still need to occur once the sperm has been placed in the egg.

In some embodiments of the methods and uses described herein, the ART is oocyte donation. In some embodiments of the methods and uses described herein, the ART is oocyte banking. In some embodiments of the methods and uses described herein, the ART is ICSI. In some embodiments of the methods and uses described herein, the ART is IVF. In some embodiments of the methods and uses described herein, the ART is an ET process. In some embodiments of the methods and uses described herein, the ART is ovulation induction. In some embodiments of the methods and uses described herein, the ART is IUI. In some embodiments of the methods and uses described herein, the ART is regulation of a menstrual cycle so a human female subject may conceive via intercourse.

The human female subjects of the methods and uses described herein may include women trying to get pregnant. The human female subjects of the methods and uses described herein may include women trying to ovulate. The human female subjects of the methods and uses described herein may include women trying to donate or bank oocytes (e.g., egg donors). The human female subjects of the methods and uses described herein may include women trying to act as surrogates. The human female subjects of the methods and uses described herein may include women undergoing COS. The human female subjects of the methods and uses described herein may also include women at risk for OHSS. The human female subjects of the methods and uses described herein may also include women who are infertile; anovulatory; of advanced maternal age (i.e., over 35 years of age); or experiencing secondary ovarian failure, oligomenorrhea, amenorrhea, endometriosis, or polyscystic ovarian syndrome (PCOS); or combinations of any of the foregoing. The human female subjects of the methods and uses described herein may include women experiencing anovulatory infertility not due to primary ovarian failure. The human female subjects of the methods and uses described herein may include women experiencing anovulatory infertility due to primary ovarian failure (e.g., where the woman is incapable of final oocyte maturation or ovulation even under COS regimens). The human female subjects of the methods and uses described herein may include women experiencing anovulatory infertility due to secondary ovarian failure. Human female subject(s) and woman (women) are used interchangeably herein.

Women at risk for OHSS may include, but are not limited to, women with one or more of PCOS, serum AMH greater than 15 pmol/L, total AFC greater than 23 via ultrasound, serum estradiol (E2) greater than 3000 pg/mL, or women who have experienced one or more previous episodes of OHSS. In some embodiments, women who are at risk for OHSS have AMH greater than 30 pmol/L, and in some embodiments, greater than 40 pmol/L. In some embodiments, women who are at risk for OHSS have a serum estradiol E2 greater than 3500 pg/mL. In other embodiments, the serum E2 is greater than 4000 pg/mL, or greater than 5000 pg/mL. In still other embodiments, women at risk for OHSS have serum estradiol E2 greater than 6000 pg/mL. Women at risk for OHSS may include, but are not limited to, women under 30 years old, women with low (lean) body weight or low BMI, women with rapidly rising E2 levels, women with a large number of follicles, and combinations of the foregoing.

Controlled ovarian stimulation (COS) and controlled ovarian hyperstimulation (COH) are used interchangeably herein and may refer to medical treatment to induce the development of multiple ovarian follicles to obtain multiple oocytes at follicular aspiration. COS may comprise three basic elements: 1. exogenous gonadotrophins to stimulate multi-follicular development; 2. cotreatment with either gonadotropin-releasing hormone (GnRH) agonist or antagonists to suppress pituitary function and prevent premature ovulation; and 3. triggering of final oocyte maturation prior to oocyte retrieval.

Use of Compound 1, a metabolite thereof, or a pharmaceutically acceptable salt of any of the foregoing, as a trigger agent during ART or for luteal phase support may result in shorter time to pregnancy, particularly relative to hCG-based trigger agents, as there should be less need for segmentation freeze protocols that result in the need for more IVF cycles. "Triggering," as used herein, may mean induction, via an LH surge, of the progression from prophase I to a second arrest at metaphase II, which remains until fertilization. This induction of final maturation initiates the mechanisms that eventually result in ovulation, and thereby make the oocytes destined to undergo ovulation unless artificial oocyte retrieval is performed first. As used herein, the "luteal phase," is the period between ovulation and either establishment of pregnancy or onset of menstrual cycle 2 weeks later. The luteal phase is characterized by the formation of corpus luteum, which is dependent on LH receptor stimulation by either LH or hCG to secrete the steroid hormones estrogen and progesterone. Following implantation, the developing blastocyst secretes hCG to maintain function of the corpus luteum. Interventions in ART, such as administration of GnRH agonists, may lead to reduced LH levels resulting in inadequate production of progesterone, luteal phase insufficiency, and possible loss of the pregnancy. "Luteal phase support" assists in counteracting luteal phase insufficiency by increasing levels of LH and/or LH receptor stimulation, therefore maintaining corpus luteum function, and/or increasing progesterone and promoting embryo implantation.

The disclosure also includes methods and uses comprising administration of Compound 1, a metabolite thereof, or a pharmaceutically acceptable salt of any of the foregoing, for decreasing the rate of OHSS. In certain such embodiments, administration of Compound 1, a metabolite thereof, or a pharmaceutically acceptable salt of any of the foregoing, provides comparable or improved pregnancy rates, decreasing the time to pregnancy, and inhibiting premature ovulation. The "inhibition of premature ovulation" may refer to inhibiting a follicle/oocyte from being released (ovulating) prematurely (i.e., earlier than oocyte maturation and timing of ovum collection for IVF or other ART regimen) due to the natural LH surge that induces ovulation. Once natural ovulation occurs, exogenous collection of ovum may become difficult, and IVF or other fertilization techniques cannot be performed, so natural ovulation is to be avoided in these circumstances.

As described above, OHSS is a syndrome characterized by ovarian enlargement and an acute fluid shift into the extravascular space. Symptoms may include, but are not limited to, abdominal distention and discomfort, hydrothorax, diminished renal perfusion, edema localized to the ovaries, ovarian diameter>5 cm or >8 cm, free fluid in abdomen, hematocrit>45%, white cell count>15*109/L, ALT or AST>2×ULN, total protein>80 g/L, creatinine>110 mol/L, or, in more severe cases, ascites and/or pleural effusion and sequelae thereof, resulting from increased vascular permeability. Complications of OHSS may include but are not limited to, hemoconcentration, hypovolemia, and electrolyte imbalances. Mild OHSS may be classified as follows: Grade 1—abdominal distention and discomfort, mild to moderate abdominal pain, abdominal bloating or increased waist size, tenderness in the area of the ovaries, and sudden weight increase of more than 6.6 pounds (3 kilograms); and Grade 2—Grade 1 disease plus nausea, vomiting, and/or diarrhea, as well as ovarian enlargement of 5-12 cm. Moderate OHSS may be classified as follows: Grade 3—features of mild OHSS plus ultrasonographic evidence of ascites and diminished renal perfusion and function. Severe OHSS may be classified as follows: Grade 4—features of moderate OHSS plus clinical evidence of ascites and/or hydrothorax, breathing difficulties or shortness of breath, severe abdominal pain, severe nausea and vomiting, blood clots in legs, decreased urination, and a tight or enlarged abdomen; and Grade 5—all of the above plus a change in the blood volume, increased blood viscosity due to hemoconcentration, coagulation abnormalities, and rapid weight gain, such as 33 to 44 pounds (15 to 20 kilograms) in five to 10 days. In severe cases, OHSS may cause death. OHSS may result from increased vascular permeability usually caused by the effects of exogenous hCG. Methods and uses described herein comprising administration of Compound 1, a metabolite thereof, or a pharmaceutically acceptable salt of any of the foregoing, may be used to treat or prevent OHSS or to treat or prevent one or more OHSS symptoms. As used herein, "treating" or "treatment" of a condition, such as a specified disease or disorder, may include treating one or more symptoms of the condition and/or preventing the occurrence of the condition. Treatment may include ameliorating one or more symptoms (e.g., pain) or preventing one or more symptoms, such as alleviating or preventing abdominal distention and discomfort associated with OHSS.

In some embodiments of the methods and uses described herein, the woman may not experience one or more symptoms of OHSS after administration of the initial dose of Compound 1, a metabolite thereof, or a pharmaceutically acceptable salt of any of the foregoing.

In some embodiments of the methods and uses described herein, one or more symptoms of OHSS may be treated after administration of the initial dose of Compound 1, a metabolite thereof, or a pharmaceutically acceptable salt of any of the foregoing.

In some embodiments of the methods and uses described herein, after administration of the initial dose of Compound 1, a metabolite thereof, or a pharmaceutically acceptable salt of any of the foregoing, the woman may not experience a worsening of one or more symptoms of OHSS.

In some embodiments of the methods and uses described herein, after administration of the initial dose of Compound 1, a metabolite thereof, or a pharmaceutically acceptable salt of any of the foregoing, one or more symptoms of OHSS may be ameliorated.

In some embodiments of the methods and uses described herein, after administration of the initial dose of Compound 1, a metabolite thereof, or a pharmaceutically acceptable salt of any of the foregoing, the woman may not experience one or more symptoms selected from the group consisting of ascites, pleural effusion, and reduced renal perfusion.

In some embodiments of the methods and uses described herein, after administration of the initial dose of Compound 1, a metabolite thereof, or a pharmaceutically acceptable salt of any of the foregoing, one or more symptoms selected from the group consisting of ascites, pleural effusion, and reduced renal perfusion may be treated.

In some embodiments of the methods and uses described herein, after administration of the initial dose of Compound 1, a metabolite thereof, or a pharmaceutically acceptable salt of any of the foregoing, ovary size may not increase to greater than 5 cm in diameter. In some embodiments of the methods and uses described herein, after administration of the initial dose of Compound 1, a metabolite thereof, or a pharmaceutically acceptable salt of any of the foregoing, ovary size may not increase to greater than 8 cm in diameter.

The use of hCG causes the ovary to undergo extensive luteinization, where large amounts of estrogens, progesterone, and local cytokines are released. VEGF (vascular endothelial growth factor) production from follicles under the effect of hCG may increase vascular hyperpermeability underlying OHSS. In the methods and uses described herein, use of Compound 1, a metabolite thereof, or a pharmaceutically acceptable salt of any of the foregoing, may inhibit or reduce VEGF and, thus, reduce vascular permeability associated with OHSS. Compound 1, a metabolite thereof, or a pharmaceutically acceptable salt of any of the foregoing, may have the ability to induce ovulation in COS without increasing hCG or VEGF levels. Compound 1, a metabolite thereof, or a pharmaceutically acceptable salt of any of the foregoing, may also have the ability to provide luteal phase support without increasing VEGF levels.

Although GnRH agonists, when used as trigger agents, are associated with lower risk of OHSS, they also result in much lower pregnancy rates. Use of Compound 1, a metabolite thereof, or a pharmaceutically acceptable salt of any of the foregoing, as a trigger agent may result in higher pregnancy rates compared to GnRH agonist triggers. In some embodiments, use of Compound 1, a metabolite thereof, or a pharmaceutically acceptable salt of any of the foregoing, as a trigger agent may result in higher pregnancy rates compared to hCG triggers. In some embodiments, use of Compound 1, a metabolite thereof, or a pharmaceutically acceptable salt of any of the foregoing, as a trigger agent may result in biochemical pregnancy rates greater than 40%. Biochemical pregnancy may refer to serum hCG>10 mIU/mL 11 days after embryo transfer. In some embodiments, use of Compound 1, a metabolite thereof, or a pharmaceutically acceptable salt of any of the foregoing, as a trigger agent may result in clinical pregnancy rates greater than 40%. Clinical pregnancy may refer to intrauterine gestational sac with heartbeat on ultrasound at 6 weeks gestation. In some embodiments, use of Compound 1, a metabolite thereof, or a pharmaceutically acceptable salt of any of the foregoing, as a trigger agent may result in live birth rates greater than 40%. Compound 1, a metabolite thereof, or a pharmaceutically acceptable salt of any of the foregoing, may induce ovulation, without excess VEGF production in follicles, without sustained increases of hCG and overstimulation of the LH receptors, and without excess amounts of estrogens, progesterone, or local cytokines, thus possibly mitigating the risk of OHSS. Oocyte maturation and ovulation induction with Compound 1, a metabolite thereof, or a pharmaceutically acceptable salt of any of the foregoing, as a trigger agent may ultimately result in pregnancy rates comparable or higher than those seen with currently available trigger agents. Compound 1, a metabolite thereof, or a pharmaceutically acceptable salt of any of the foregoing, may also mitigate the symptoms of polycystic ovarian syndrome (PCOS), as they may stimulate normalization of ovulation in patients with ovarian dysfunction.

In some embodiments, use of Compound 1, a metabolite thereof, or a pharmaceutically acceptable salt of any of the foregoing, for luteal phase support during ART may significantly decrease the risk of OHSS compared to conventional therapy (i.e., hCG luteal phase support). Compound 1, a metabolite thereof, or a pharmaceutically acceptable salt of any of the foregoing, may provide luteal phase support, without excess VEGF production in follicles and without excess amounts of estrogens, progesterone, or local cytokines, thus possibly mitigating the risk of OHSS. Use of Compound 1, a metabolite thereof, or a pharmaceutically acceptable salt of any of the foregoing, for luteal phase support may also ultimately result in pregnancy rates comparable or higher than those seen with currently available luteal phase support agents. In some embodiments, use of Compound 1, a metabolite thereof, or a pharmaceutically acceptable salt of any of the foregoing, for luteal phase support may result in biochemical pregnancy rates greater than 40%. In some embodiments, use of Compound 1, a metabolite thereof, or a pharmaceutically acceptable salt of any of the foregoing, for luteal phase support may result in clinical pregnancy rates greater than 40%. In some embodiments, use of Compound 1, a metabolite thereof, or a pharmaceutically acceptable salt of any of the foregoing, for luteal phase support may result in live birth rates greater than 40%.

The present disclosure provides methods and uses for increasing pregnancy rates following induction of ovulation with Compound 1, a metabolite thereof, or a pharmaceutically acceptable salt of any of the foregoing, instead of hCG or a GnRH agonist trigger agent. In some embodiments, Compound 1, a metabolite thereof, or a pharmaceutically acceptable salt of any of the foregoing, is administered to a human female subject as a trigger agent and administration follows the phase of COS. In some embodiments, Compound 1, a metabolite thereof, or a pharmaceutically acceptable salt of any of the foregoing, may effectively promote maturation of follicles and induce ovulation (i) without increasing the total blood concentration level of VEGF or (ii) by increasing the total level of VEGF for less than 24 hours after administration. In some embodiments, Compound 1, a metabolite thereof, or a pharmaceutically acceptable salt of any of the foregoing, are used for luteal phase support to increase pregnancy rates.

The present disclosure also provides methods and uses for increasing pregnancy rates following induction of ovulation with a trigger agent comprising administration of Compound 1, a metabolite thereof, or a pharmaceutically acceptable salt of any of the foregoing, for luteal phase support. In some embodiments, administration of Compound 1, a metabolite thereof, or a pharmaceutically acceptable salt of any of the foregoing, follows or occurs at substantially the same time as triggering. In certain such embodiments, Compound 1, a metabolite thereof, or a pharmaceutically acceptable salt of any of the foregoing, may provide luteal phase support (i) without increasing the total blood concentration level of VEGF or (ii) by increasing the total level of VEGF for less than 24 hours after administration.

Progestogens, such as progesterone, may or may not be administered in connection with methods and uses described herein. In some embodiments, progesterone is not administered with the methods and uses described herein. Indeed, one possible advantage of administering multiple doses of Compound 1, a metabolite thereof, or a pharmaceutically acceptable salt of any of the foregoing, is that progestogen may not be required for luteal phase support. This would greatly simplify ART protocols, as many require daily administration of a progestogen, such as progesterone, often by injection. Sometimes, administration of a progestogen, such as progesterone, is required for 3 months or more after egg retrieval. Eliminating or reducing the need for a progestogen, such as progesterone, through administration of Compound 1, a metabolite thereof, or a pharmaceutically acceptable salt of any of the foregoing, would ease the burden imposed by ART and simplify protocols.

The present disclosure further provides methods and uses for reducing the likelihood of developing OHSS following inducement of ovulation with Compound 1, a metabolite thereof, or a pharmaceutically acceptable salt of any of the foregoing, instead of an hCG-containing trigger regimen. In some embodiments, the method or use follows the phase of COS and entails administering to a human female subject Compound 1, a metabolite thereof, or a pharmaceutically acceptable salt of any of the foregoing, as a trigger agent, that may effectively promote maturation of follicles and induce ovulation. In some embodiments, use of Compound 1, a metabolite thereof, or a pharmaceutically acceptable salt of any of the foregoing, as a trigger agent (i) does not increase the total blood concentration level of VEGF or (ii) increases the total level of VEGF for less than 24 hours after administration.

The present disclosure further provides for reducing the likelihood of developing OHSS following inducement of ovulation by using Compound 1, a metabolite thereof, or a pharmaceutically acceptable salt of any of the foregoing, for luteal phase support. In certain such embodiments, administration of Compound 1, a metabolite thereof, or a pharmaceutically acceptable salt of any of the foregoing, follows or occurs at substantially the same time as triggering. In some embodiments, use of Compound 1, a metabolite thereof, or a pharmaceutically acceptable salt of any of the foregoing, for luteal phase support (i) does not increase the total blood concentration level of VEGF or (ii) increases the total level of VEGF for less than 24 hours after administration.

The disclosure provides for methods of using Compound 1, a metabolite thereof, or a pharmaceutically acceptable salt of any of the foregoing, to increase the endogenous LH level in a woman in need thereof undergoing ART, wherein at least about 36 hours after the initial dose is administered, the woman's endogenous LH level in blood is elevated compared to the woman's endogenous LH level in blood prior to administration of the initial dose. In some embodiments, at least about 24 hours after the initial dose of Compound 1, a metabolite thereof, or a pharmaceutically acceptable salt of any of the foregoing, is administered, the woman's endogenous LH level in blood is elevated compared to the woman's endogenous LH level in blood prior to administration of the initial dose. In some embodiments, at least about 40 hours after the initial dose of Compound 1, a metabolite thereof, or a pharmaceutically acceptable salt of any of the foregoing, is administered, the woman's endogenous LH level in blood is elevated compared to the woman's endogenous LH level in blood prior to administration of the initial dose. In some embodiments, at least about 44 hours after the initial dose of Compound 1, a metabolite thereof, or a pharmaceutically acceptable salt of any of the foregoing, is administered, the woman's endogenous LH level in blood is elevated compared to the woman's endogenous LH level in blood prior to administration of the initial dose. In some embodiments, at least about 48 hours after the initial dose of Compound 1, a metabolite thereof, or a pharmaceutically acceptable salt of any of the foregoing, is administered, the woman's endogenous LH level in blood is elevated compared to the woman's endogenous LH level in blood prior to administration of the initial dose. In some embodiments, at least about 52 hours after the initial dose of Compound 1, a metabolite thereof, or a pharmaceutically acceptable salt of any of the foregoing, is administered, the woman's endogenous LH level in blood is elevated compared to the woman's endogenous LH level in blood prior to administration of the initial dose.

The disclosure also provides for methods of using Compound 1, a metabolite thereof, or a pharmaceutically acceptable salt of any of the foregoing, to increase the endogenous LH level in a woman in need thereof undergoing ART, wherein the maximum endogenous LH level in blood occurs at least about 12 hours after administration of the initial dose. In some embodiments, after administration of an initial dose of Compound 1, a metabolite thereof, or a pharmaceutically acceptable salt of any of the foregoing, the maximum endogenous LH level in blood occurs between about 12 hours and about 48 hours after administration of the initial dose. In some embodiments, after administration of an initial dose of Compound 1, a metabolite thereof, or a pharmaceutically acceptable salt of any of the foregoing, the maximum endogenous LH level in blood occurs between about 12 hours and about 36 hours after administration of the initial dose. In some embodiments, after administration of an initial dose of Compound 1, a metabolite thereof, or a pharmaceutically acceptable salt of any of the foregoing, the maximum endogenous LH level in blood occurs between about 12 hours and about 24 hours after administration of the initial dose. In some embodiments, after administration of an initial dose of Compound 1, a metabolite thereof, or a pharmaceutically acceptable salt of any of the foregoing, the maximum endogenous LH level in blood occurs between about 12 hours and about 18 hours after administration of the initial dose. In some embodiments, after administration of an initial dose of Compound 1, a metabolite thereof, or a pharmaceutically acceptable salt of any of the foregoing, the maximum endogenous LH level in blood occurs between about 14 hours after administration of the initial dose. In some embodiments, after administration of an initial dose of Compound 1, a metabolite thereof, or a pharmaceutically acceptable salt of any of the foregoing, the maximum endogenous LH level in blood occurs between about 16 hours after administration of the initial dose. In some embodiments, after administration of an initial dose of Compound 1, a metabolite thereof, or a pharmaceutically acceptable salt of any of the foregoing, the maximum endogenous LH level in blood occurs between about 18 hours after administration of the initial dose. In some embodiments, after administration of an initial dose of Compound 1, a metabolite thereof, or a pharmaceutically acceptable salt of any of the foregoing, the maximum endogenous LH level in blood occurs between about 20 hours after administration of the initial dose. In some embodiments, after administration of an initial dose of Compound 1, a metabolite thereof, or a pharmaceutically acceptable salt of any of the foregoing, the maximum endogenous LH level in blood occurs between about 22 hours after administration of the initial dose. In some embodiments, after administration of an initial dose of Compound 1, a metabolite thereof, or a pharmaceutically acceptable salt of any of the foregoing, the maximum endogenous LH level in blood occurs between about 24 hours after administration of the initial dose. In some embodiments, after administration of an initial dose of Compound 1, a metabolite thereof, or a pharmaceutically acceptable salt of any of the foregoing, the maximum endogenous LH level in blood occurs between about 28 hours after administration of the initial dose. In some embodiments, after administration of an initial dose of Compound 1, a metabolite thereof, or a pharmaceutically acceptable salt of any of the foregoing, the maximum endogenous LH level in blood occurs between about 32 hours after administration of the initial dose. In some embodiments, after administration of an initial dose of Compound 1, a metabolite thereof, or a pharmaceutically acceptable salt of any of the foregoing, the maximum endogenous LH level in blood occurs between about 36 hours after administration of the initial dose.

The disclosure provides for methods and uses of increasing endogenous LH level in a woman undergoing ART and in need of luteal phase support, comprising administering to the woman an initial dose of Compound 1, a metabolite thereof, or a pharmaceutically acceptable salt of any of the foregoing, after said woman has received a trigger dose of an oocyte maturation agent as part of an ART regimen. An oocyte maturation agent, or trigger agent, may be used to promote the final maturation of oocytes in ART regimens prior to oocyte retrieval (e.g., IVF, ICSI) or prior to ovulation as part of treatment of e.g., PCOS, where after ovulation, IUI or intercourse is timed to maximize the chance of conception. Oocyte maturation agents may include, for example, Compound 1, a metabolite thereof, or a pharmaceutically acceptable salt of any of the foregoing, hCG, recombinant luteinizing hormone (rLH), or a GnRH agonist. In some embodiments, the GnRH agonist is selected from the group consisting of leuprorelin acetate, gonadorelin, buserelin, triptorelin, goserelin, nafarelin, histrelin, deslorelin, meterelin, lecirelin, or pharmaceutically acceptable salts of any of the foregoing. In some embodiments, one or more doses of Compound 1, a metabolite thereof, or a pharmaceutically acceptable salt of any of the foregoing, may be administered to the woman in need of luteal phase support either prior to oocyte retrieval, after oocyte retrieval, or both before and after oocyte retrieval. Likewise, for ART regimens not incorporating retrieval of the oocyte, one or more doses of Compound 1, a metabolite thereof, or a pharmaceutically acceptable salt of any of the foregoing, may be administered to the woman in need of luteal phase support either prior to ovulation, after ovulation, or both before and after ovulation.

In some embodiments of the methods and uses described herein, a woman's endogenous LH level in blood is elevated between about 12 hours to about 96 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 12 hours to about 84 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 12 hours to about 72 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 12 hours to about 60 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 12 hours to about 48 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 14 hours to about 84 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 14 hours to about 72 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 14 hours to about 60 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 14 hours to about 48 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 24 hours to about 84 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 24 hours to about 72 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 24 hours to about 60 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, a woman's endogenous LH level in blood is elevated between about 24 hours to about 48 hours after administration of the initial dose of Compound 1, a metabolite thereof, or a pharmaceutically acceptable salt of any of the foregoing, compared to the woman's endogenous LH level in blood prior to administration of the initial dose.

In some embodiments of the methods and uses described herein, the woman's endogenous LH level in blood is elevated for at least about 36 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for at least about 48 hours after administration of the initial dose of Compound 1, a metabolite thereof, or a pharmaceutically acceptable salt of any of the foregoing, compared to the woman's endogenous LH level in blood prior to administration of the initial dose. One potential advantage of the methods and uses described herein is the convenience of an LH level increase beyond 36 hours compared to current triggers. If ovulation reliably happens after approximately 48 hours from the initial dose of Compound 1, a metabolite thereof, or a pharmaceutically acceptable salt of any of the foregoing, the methods and uses described herein would be beneficial for the logistics of scheduling ART appointments compared to the current standard of care. Currently, if a trigger is given around 8 pm, then egg collection occurs 36 hours later (8 am). If egg collection could reliably occur at ~48 hours, as provided in the current disclosure, patients could be given a trigger and have egg collection during normal business hours. In some embodiments of the methods and uses described herein, the woman's endogenous LH level in blood is elevated for at least about 48 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 16 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 12 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 11 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 10 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 9 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 8 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 7 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 6 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 5 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 4 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 3 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 36 hours to about 2 days after administration of the initial dose of Compound 1, a metabolite thereof, or a pharmaceutically acceptable salt of any of the foregoing, compared to the woman's endogenous LH level in blood prior to administration of the initial dose.

In some embodiments of the methods and uses described herein, the woman's endogenous LH level in blood is elevated for about 48 hours to about 16 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 48 hours to about 12 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 48 hours to about 11 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 48 hours to about 10 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 48 hours to about 9 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 48 hours to about 8 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 48 hours to about 7 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 48 hours to about 6 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 48 hours to about 5 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 48 hours to about 4 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 48 hours to about 3 days after administration of the initial dose of Compound 1, a metabolite thereof, or a pharmaceutically acceptable salt of any of the foregoing, compared to the woman's endogenous LH level in blood prior to administration of the initial dose.

In some embodiments of the methods and uses described herein, the woman's endogenous LH level in blood is elevated for about 24 hours to about 16 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 24 hours to about 12 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 24 hours to about 11 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 24 hours to about 10 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 24 hours to about 9 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 24 hours to about 8 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 24 hours to about 7 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 24 hours to about 6 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 24 hours to about 5 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 24 hours to about 4 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 24 hours to about 3 days after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein, the woman's endogenous LH level in blood is elevated for about 24 hours to about 2 days after administration of the initial dose of Compound 1, a metabolite thereof, or a pharmaceutically acceptable salt of any of the foregoing, compared to the woman's endogenous LH level in blood prior to administration of the initial dose.

Compound 1, a metabolite thereof, or a pharmaceutically acceptable salt of any of the foregoing, may be used to promote the maturation of an ova or ovum, which may then be subsequently retrieved and fertilized by IVF or ICSI and then transplanted in the uterus (ET). Alternatively, the ova or ovum may be released from the ovaries (induced ovulation) and be subsequently fertilized via sexual intercourse or IUI. For appropriate and successful oocyte retrieval, there must first occur, the maturation of oocytes and the induction of those oocytes at the appropriate time. The COS phase may help to prevent premature ovulation and the use of Compound 1, a metabolite thereof, or a pharmaceutically acceptable salt of any of the foregoing, as the trigger agent may facilitate the maturation of the oocytes and allow for retrieval, in vitro fertilization, and embryo transfer or induce release of oocytes (ovulation) and allow for fertilization via sexual intercourse or IUI. As such, administration of Compound 1, a metabolite thereof, or a pharmaceutically acceptable salt of any of the foregoing, may result in pregnancy rates that are similar or higher than the current rates, shorter time to pregnancy, and reduced risk for the development of OHSS.

The present disclosure provides methods and uses comprising administration of Compound 1, a metabolite thereof, or a pharmaceutically acceptable salt of any of the foregoing, for promoting oocyte maturation and triggering ovulation in assisted reproductive technologies (ART). The methods and uses described herein may permit use of Compound 1, a metabolite thereof, or a pharmaceutically acceptable salt of any of the foregoing, for promoting oocyte maturation and triggering ovulation in ART in the absence of administration of another triggering agent, such as hCG, exogenous LH, and/or a GnRH agonist. In some embodiments of the methods and uses described herein, the initial dose of Compound 1, a metabolite thereof, or a pharmaceutically acceptable salt of any of the foregoing, promotes oocyte maturation. In some embodiments of the methods and uses described herein, oocyte maturation occurs without the administration of exogenous hCG or exogenous LH. In certain such embodiments, the yield of mature oocytes is at least 50%. In certain such embodiments, the yield of mature oocytes is at least 75%. Oocyte yield may refer to the percentage of mature (metaphase 2; M2) oocytes collected from the number of follicles 14 mm on final ultrasound scan prior to trigger administration. Oocytes may be independently classified as M2 by presence of the first polar body and round ooplasm. In some embodiments, administration of a trigger comprising Compound 1, a metabolite thereof, or a pharmaceutically acceptable salt of any of the foregoing, yields an increased amount of mature oocytes compared to hCG triggering.

As used herein, a "mature" oocyte is one that has reached the metaphase II stage (M2). Oocytes are classified as M2 by the presence of the first polar body and round ooplasm. Oocytes resume meiotic maturation in response to the midcycle LH surge. This final oocyte maturation may be induced medically with either hCG or a GnRH agonist. The former binds the LH receptor, while the GnRH agonist promotes the release of endogenous gonadotropin stores from the hypophysis. The resumption of meiosis (so called nuclear maturation) occurs 14-18 hours after the beginning of the LH surge; meiosis I is completed within 35 hours and the oocytes reach the metaphase II stage (M2). Meanwhile, in response to the LH surge, the cumulus cells display almost complete expansion by 20 hours; then the mature cumulus-oocyte complex detach from the follicular wall before ovulation. While nuclear maturation and cumulus expansion are closely linked, it is unclear if different LH levels are needed to regulate the two processes.

According to the present disclosure, in some embodiments, administration of Compound 1, a metabolite thereof, or a pharmaceutically acceptable salt of any of the foregoing, promotes oocyte maturation and induces (triggers) ovulation in the human female subject (i) without increasing the level of VEGF or (ii) increasing such level for less than 24 hours.

The present disclosure provides for methods and uses for inducing ovulation using Compound 1, a metabolite thereof, or a pharmaceutically acceptable salt of any of the foregoing. In certain such embodiments, the method or use may have the steps of administering to a human female subject an amount of FSH or the like, coupled with a GnRH agonist or antagonist to facilitate the initial COS phase of ART. In some embodiments, the initial COS phase may be followed by the administration of Compound 1, a metabolite thereof, or a pharmaceutically acceptable salt of any of the foregoing, as a trigger agent that effectively promotes maturation of oocytes and induces ovulation. In some embodiments, administration of Compound 1, a metabolite thereof, or a pharmaceutically acceptable salt of any of the foregoing, as a trigger agent that effectively promotes maturation of oocytes and induces ovulation (i) without increasing the total blood concentration level of VEGF or (ii) by increasing the total level of VEGF for less than 24 hours. In some embodiments, during the COS phase, a GnRH antagonist or a GnRH agonist may be administered in an amount and for a period of time sufficient to act to suppress ovulation in a controlled fashion and is given in conjunction with FSH or FSH analogs. In some embodiments, the GnRH antagonist is relugolix.

The present disclosure also provides for methods and uses comprising administration of Compound 1, a metabolite thereof, or a pharmaceutically acceptable salt of any of the foregoing, for inducing ovulation in an anovulatory, human female subject suffering from secondary ovarian failure. Secondary ovarian failures originate in the hypothalamus and pituitary glands when they fail to hormonally stimulate the ovaries and subsequent ovarian function. In some embodiments, the method or use comprises the steps of (1) pretreating the subject with human gonadotropins and (2) administering to the subject Compound 1, a metabolite thereof, or a pharmaceutically acceptable salt of any of the foregoing.

The present disclosure also provides for methods and uses comprising administration of Compound 1, a metabolite thereof, or a pharmaceutically acceptable salt of any of the foregoing, for providing luteal phase support in an anovulatory, human female subject suffering from primary ovarian failure. Primary ovarian failure is the depletion or dysfunction of ovarian follicles with cessation of menses before age 40 years. "Primary ovarian insufficiency" is the preferred term for primary ovarian failure advocated by the National Institutes of Health because ovarian function is intermittent or unpredictable in many cases. Because 5-10% of women with primary ovarian insufficiency experience spontaneous conception and delivery, primary ovarian insufficiency can be distinguished from natural menopause and also may be described as decreased ovarian reserve. In some embodiments, the methods and uses may further comprise an ET process.

The present disclosure provides for methods and uses comprising administration of Compound 1, a metabolite thereof, or a pharmaceutically acceptable salt of any of the foregoing, for inducing final follicular maturation and early luteinization in a woman undergoing ART, wherein said woman has undergone pituitary desensitization and has been pretreated with follicle stimulating hormones. In certain such embodiments, after the initial dose of Compound 1, a metabolite thereof, or a pharmaceutically acceptable salt of any of the foregoing, is administered, the woman's endogenous LH level in blood is elevated compared to the woman's endogenous LH level in blood prior to administration of the initial dose. In some embodiments of the methods and uses described herein wherein administration of Compound 1, a metabolite thereof, or a pharmaceutically acceptable salt of any of the foregoing, is for inducing final follicular maturation and early luteinization in a woman undergoing ART, and said woman has undergone pituitary desensitization and has been pretreated with follicle stimulating hormones, the woman is at risk for OHSS. In some embodiments of the methods and uses described herein wherein administration of Compound 1, a metabolite thereof, or a pharmaceutically acceptable salt of any of the foregoing, is for inducing final follicular maturation and early luteinization in a woman undergoing ART, and said woman has undergone pituitary desensitization and has been pretreated with follicle stimulating hormones, at least about 36 hours after administration, the woman's endogenous LH level in blood is elevated compared to the woman's endogenous LH level in blood prior to administration of the initial dose. In some embodiments of the methods and uses described herein wherein administration of Compound 1, a metabolite thereof, or a pharmaceutically acceptable salt of any of the foregoing, is for inducing final follicular maturation and early luteinization in a woman undergoing ART, and said woman has undergone pituitary desensitization and has been pretreated with follicle stimulating hormones, the maximum endogenous LH level in blood occurs at least about 12 hours after administration of an initial dose of Compound 1, a metabolite thereof, or a pharmaceutically acceptable salt of any of the foregoing. In some embodiments of the methods and uses described herein wherein administration of Compound 1, a metabolite thereof, or a pharmaceutically acceptable salt of any of the foregoing, is for inducing final follicular maturation and early luteinization in a woman undergoing ART, and said woman has undergone pituitary desensitization and has been pretreated with follicle stimulating hormones, the maximum endogenous LH level in blood occurs between about 12 hours and about 48 hours after administration of an initial dose of Compound 1, a metabolite thereof, or a pharmaceutically acceptable salt of any of the foregoing. In some embodiments of the methods and uses described herein wherein administration of Compound 1, a metabolite thereof, or a pharmaceutically acceptable salt of any of the foregoing, is for inducing final follicular maturation and early luteinization in a woman undergoing ART, and said woman has undergone pituitary desensitization and has been pretreated with follicle stimulating hormones, the woman's endogenous LH level in blood is elevated between about 12 hours to about 96 hours after administration of an initial dose of Compound 1, a metabolite thereof, or a pharmaceutically acceptable salt of any of the foregoing, compared to the woman's endogenous LH level in blood prior to administration of the initial dose. In some embodiments of the methods and uses described herein wherein administration of Compound 1, a metabolite thereof, or a pharmaceutically acceptable salt of any of the foregoing, is for inducing final follicular maturation and early luteinization in a woman undergoing ART, and said woman has undergone pituitary desensitization and has been pretreated with follicle stimulating hormones, the woman's endogenous LH level in blood is elevated for at least about 36 hours after administration compared to the woman's endogenous LH level in blood prior to administration of the initial dose. In some embodiments of the methods and uses described herein wherein administration of Compound 1, a metabolite thereof, or a pharmaceutically acceptable salt of any of the foregoing, is for inducing final follicular maturation and early luteinization in a woman undergoing ART, and said woman has undergone pituitary desensitization and has been pretreated with follicle stimulating hormones, the woman's endogenous LH level in blood is elevated for at least about 24 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein wherein administration of Compound 1, a metabolite thereof, or a pharmaceutically acceptable salt of any of the foregoing, is for inducing final follicular maturation and early luteinization in a woman undergoing ART, and said woman has undergone pituitary desensitization and has been pretreated with follicle stimulating hormones, the endogenous LH level in blood is elevated for about 36 hours to about 16 days after the initial dose of Compound 1, a metabolite thereof, or a pharmaceutically acceptable salt of any of the foregoing. In some embodiments of the methods and uses described herein wherein administration of Compound 1, a metabolite thereof, or a pharmaceutically acceptable salt of any of the foregoing, is for inducing final follicular maturation and early luteinization in a woman undergoing ART, and said woman has undergone pituitary desensitization and has been pretreated with follicle stimulating hormones, the endogenous LH level in blood is elevated for about 36 hours to about 12 days after the initial dose of Compound 1, a metabolite thereof, or a pharmaceutically acceptable salt of any of the foregoing. In some embodiments of the methods and uses described herein wherein administration of Compound 1, a metabolite thereof, or a pharmaceutically acceptable salt of any of the foregoing, is for inducing final follicular maturation and early luteinization in a woman undergoing ART, and said woman has undergone pituitary desensitization and has been pretreated with follicle stimulating hormones, the endogenous LH level in blood is elevated for about 24 hours to about 16 days after the initial dose of Compound 1, a metabolite thereof, or a pharmaceutically acceptable salt of any of the foregoing. In some embodiments of the methods and uses described herein wherein administration of Compound 1, a metabolite thereof, or a pharmaceutically acceptable salt of any of the foregoing, is for inducing final follicular maturation and early luteinization in a woman undergoing ART, and said woman has undergone pituitary desensitization and has been pretreated with follicle stimulating hormones, the endogenous LH level in blood is elevated for about 24 hours to about 12 days after the initial dose of Compound 1, a metabolite thereof, or a pharmaceutically acceptable salt of any of the foregoing.

The present disclosure provides for methods and uses comprising administration of Compound 1, a metabolite thereof, or a pharmaceutically acceptable salt of any of the foregoing, for inducing ovulation in woman who is anovulatory infertile and the infertility is not due to primary ovarian failure. In certain such embodiments, after the initial dose of Compound 1, a metabolite thereof, or a pharmaceutically acceptable salt of any of the foregoing, is administered, the woman's endogenous LH level in blood is elevated compared to the woman's endogenous LH level in blood prior to administration of the initial dose.

In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, the woman is at risk for OHSS. In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, at least about 36 hours after an initial dose Compound 1, a metabolite thereof, or a pharmaceutically acceptable salt of any of the foregoing, is administered, the woman's endogenous LH level in blood is elevated compared to the woman's endogenous LH level in blood prior to administration of the initial dose. In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, at least about 24 hours after an initial dose Compound 1, a metabolite thereof, or a pharmaceutically acceptable salt of any of the foregoing, is administered, the woman's endogenous LH level in blood is elevated compared to the woman's endogenous LH level in blood prior to administration of the initial dose. In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, the maximum endogenous LH level in blood occurs at least about 12 hours after administration of an initial dose of Compound 1, a metabolite thereof, or a pharmaceutically acceptable salt of any of the foregoing. In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, the maximum endogenous LH level in blood occurs between about 12 hours and about 48 hours after administration of an initial dose of Compound 1, a metabolite thereof, or a pharmaceutically acceptable salt of any of the foregoing. In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, the woman's endogenous LH level in blood is elevated between about 12 hours to about 96 hours after administration of an initial dose of Compound 1, a metabolite thereof, or a pharmaceutically acceptable salt of any of the foregoing, compared to the woman's endogenous LH level in blood prior to administration of the initial dose. In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, the woman's endogenous LH level in blood is elevated for at least about 36 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, the endogenous LH level in blood is elevated for at least about 36 hours to about 16 days after the initial dose of Compound 1, a metabolite thereof, or a pharmaceutically acceptable salt of any of the foregoing. In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, the endogenous LH level in blood is elevated for at least about 36 hours to about 12 days after the initial dose of Compound 1, a metabolite thereof, or a pharmaceutically acceptable salt of any of the foregoing. In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, the woman's endogenous LH level in blood is elevated for at least about 24 hours after administration of the initial dose of Compound 1, a metabolite thereof, or a pharmaceutically acceptable salt of any of the foregoing, compared to the woman's endogenous LH level in blood prior to administration of the initial dose. In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, the endogenous LH level in blood is elevated for at least about 24 hours to about 16 days after the initial dose of Compound 1, a metabolite thereof, or a pharmaceutically acceptable salt of any of the foregoing. In some embodiments of the methods and uses described herein wherein administration of Compound 1, a metabolite thereof, or a pharmaceutically acceptable salt of any of the foregoing, is for inducing ovulation in woman who is anovulatory infertile and the infertility is not due to primary ovarian failure, the endogenous LH level in blood is elevated for at least about 24 hours to about 12 days after the initial dose of Compound 1, a metabolite thereof, or a pharmaceutically acceptable salt of any of the foregoing.

Larger follicle size at the time of triggering may improve the yield of mature oocytes. The disclosure provides for administration of doses of Compound 1, a metabolite thereof, or a pharmaceutically acceptable salt of any of the foregoing, wherein the initial dose is administered when at least three ovarian follicles of at least about 14 mm are visible via ultrasound. In some embodiments of the methods and uses described herein, the initial doses of Compound 1, a metabolite thereof, or a pharmaceutically acceptable salt of any of the foregoing, are administered when at least three ovarian follicles of at least about 18 mm are visible via ultrasound.

The disclosure also provides for administration of doses of Compound 1, a metabolite thereof, or a pharmaceutically acceptable salt of any of the foregoing, wherein the initial dose is administered after ovulation. In some embodiments of the methods and uses described herein, the initial dose of Compound 1, a metabolite thereof, or a pharmaceutically acceptable salt of any of the foregoing, is administered prior to ovulation.

In some embodiments, the methods and uses described herein comprise oocyte retrieval. The disclosure provides for administration of doses of Compound 1, a metabolite thereof, or a pharmaceutically acceptable salt of any of the foregoing, wherein the initial dose is administered after oocyte retrieval. In some embodiments of the methods and uses described herein, the initial dose of Compound 1, a metabolite thereof, or a pharmaceutically acceptable salt of any of the foregoing, is administered prior to oocyte retrieval.

In some embodiments of the methods and uses described herein, prior to administration of the initial dose of Compound 1, a metabolite thereof, or a pharmaceutically acceptable salt of any of the foregoing, a woman's pituitary is desensitized to GnRH prior to administration of the initial dose. In certain embodiments of the methods and uses described herein, the initial dose of Compound 1, a metabolite thereof, or a pharmaceutically acceptable salt of any of the foregoing, is administered when serum estradiol concentration is at least about 0.49 nmol/L. In certain embodiments of the methods and uses described herein, the initial dose of Compound 1, a metabolite thereof, or a pharmaceutically acceptable salt of any of the foregoing, is administered when serum estradiol concentration is at least about 0.91 nmol/L.

In some embodiments of the methods and uses described herein, an embryo is implanted after administration of an initial dose of Compound 1, a metabolite thereof, or a pharmaceutically acceptable salt of any of the foregoing. In certain such embodiments, implantation occurs within about 2 to about 10 days after administration of the initial dose, such as about 2 days, about 3 days, about 4 days, about 5 days, about 6 days, about 7 days, about 8 days, about 9 days, or about 10 days. In some embodiments of the methods and uses described herein, embryo implantation occurs within about 1 to about 7 days after oocyte retrieval, such as about 1 day, about 2 days, about 3 days, about 4 days, about 5 days, about 6 days, or about 7 days. In certain embodiments of the methods and uses described herein, the embryo is fresh (i.e., the embryo has not been frozen). In certain such embodiments, the embryo is implanted within the same menstrual cycle as oocyte retrieval. Due to the mode of action of Compound 1, a metabolite thereof, or a pharmaceutically acceptable salt of any of the foregoing, there may be less negative impact on the endometrium compared to current treatments. Thus, the endometrium may be ready for implantation (higher endometrial receptivity) immediately after egg retrieval. By not using hCG-based or GnRH agonist trigger agents (including dual triggers with GnRH agonists), Compound 1, a metabolite thereof, or a pharmaceutically acceptable salt of any of the foregoing, may result in less need for a segmentation freezing protocol, thereby reducing the number of IVF cycles; shortening time to pregnancy, while maintaining acceptable pregnancy rates; lowering costs; and reducing reduced side effects, such as macrosomia (large for gestational age), risk of placenta accreta, and risk of preeclampsia, with significantly lower OHSS rates. Compound 1, a metabolite thereof, or a pharmaceutically acceptable salt of any of the foregoing, may provide safety and efficacy attributes that represent an advantage compared to current treatments that require segmentation.

Because fresh embryos may be used in the uses and methods of the present disclosure, the disclosure also provides for decreasing the time to pregnancy following inducement of ovulation with Compound 1, a metabolite thereof, or a pharmaceutically acceptable salt of any of the foregoing, instead of hCG or a GnRH agonist trigger agent. In some embodiments, Compound 1, a metabolite thereof, or a pharmaceutically acceptable salt of any of the foregoing, is administered to a human female subject as a trigger agent and administration follows the phase of COS. In certain such embodiments, Compound 1, a metabolite thereof, or a pharmaceutically acceptable salt of any of the foregoing, may effectively promote maturation of follicles and induce ovulation (i) without increasing the total blood concentration level of VEGF or (ii) by increasing the total level of VEGF for less than 24 hours after administration.

The present disclosure also provides methods and uses for decreasing the time to pregnancy following inducement of ovulation with a trigger agent comprising administration of Compound 1, a metabolite thereof, or a pharmaceutically acceptable salt of any of the foregoing, for luteal phase support. In some embodiments, administration of Compound 1, a metabolite thereof, or a pharmaceutically acceptable salt of any of the foregoing, follows or occurs at substantially the same time as triggering. In certain such embodiments, Compound 1, a metabolite thereof, or a pharmaceutically acceptable salt of any of the foregoing, may provide luteal phase support (i) without increasing the total blood concentration level of VEGF or (ii) by increasing the total level of VEGF for less than 24 hours after administration.

The disclosure provides for methods and uses comprising administration of doses of Compound 1, a metabolite thereof, or a pharmaceutically acceptable salt of any of the foregoing, wherein the method or use induces ovulation. In certain such embodiments, the human female subject conceives via intercourse or IUI after administration of at least the initial dose of Compound 1, a metabolite thereof, or a pharmaceutically acceptable salt of any of the foregoing. Administration of Compound 1, a metabolite thereof, or a pharmaceutically acceptable salt of any of the foregoing, to trigger oocyte release without oocyte retrieval may result in a predictable time of ovulation, with the interval from administration to ovulation ranging from 30 to 62 hours after administration, or from 36 to 48 hours after administration. This may allow for sexual intercourse or IUI to conveniently be scheduled at ovulation, maximizing the chances of conception. Administration of Compound 1, a metabolite thereof, or a pharmaceutically acceptable salt of any of the foregoing, may also help women who have trouble ovulating to ovulate and conceive via intercourse or IUI. In some embodiments, triggering oocyte release using Compound 1, a metabolite thereof, or a pharmaceutically acceptable salt of any of the foregoing, may be reserved for women who require IUI and in whom LH monitoring proves difficult or unreliable. In some embodiments, triggering oocyte release using Compound 1, a metabolite thereof, or a pharmaceutically acceptable salt of any of the foregoing, may be used when LH monitoring hasn't shown an LH surge by cycle day 18 (where cycle day 1 is the first day of the preceding menstruation) and there is an ovarian follicle of over 20 mm in size.

In some embodiments of the methods and uses described herein, after administration of at least the initial dose of Compound 1, a metabolite thereof, or a pharmaceutically acceptable salt of any of the foregoing, the human female subject conceives or gives birth. In some embodiments, the human female subject gives birth via a Caesarean section. In some embodiments, the human female subject gives birth vaginally.

In some embodiments of the methods and uses described herein, the amount or dose, such as the initial dose, of Compound 1, or a corresponding amount of a pharmaceutically acceptable salt thereof, administered or used is about 0.00003 mg to about 0.030 mg. In some embodiments of the methods and uses described herein, the amount or dose, such as the initial dose, of Compound 1, or a corresponding amount of a pharmaceutically acceptable salt thereof, administered or used is about 0.001 mg to about 0.030 mg. In some embodiments of the methods and uses described herein, the amount or dose, such as the initial dose, of Compound 1, or a corresponding amount of a pharmaceutically acceptable salt thereof, administered or used is about 0.001 mg to about 0.003 mg. In some embodiments of the methods and uses described herein, the amount or dose, such as the initial dose, of Compound 1, or a corresponding amount of a pharmaceutically acceptable salt thereof, administered or used is about 0.00003 mg to about 0.0003 mg. In some embodiments of the methods and uses described herein, the amount or dose, such as the initial dose, of Compound 1, or a corresponding amount of a pharmaceutically acceptable salt thereof, administered or used is about 0.00003 mg to about 0.003 mg. In some embodiments of the methods and uses described herein, the amount or dose, such as the initial dose, of Compound 1, or a corresponding amount of a pharmaceutically acceptable salt thereof, administered or used is about 0.00003 mg to about 0.00006 mg. In some embodiments of the methods and uses described herein, the amount or dose, such as the initial dose, of Compound 1, or a corresponding amount of a pharmaceutically acceptable salt thereof, administered or used is about 0.00003 mg to about 0.00009 mg. In some embodiments of the methods and uses described herein, the amount or dose, such as the initial dose, of Compound 1, or a corresponding amount of a pharmaceutically acceptable salt thereof, administered or used is about 0.00003 mg to about 0.00015 mg. In some embodiments of the methods and uses described herein, the amount or dose, such as the initial dose, of Compound 1, or a corresponding amount of a pharmaceutically acceptable salt thereof, administered or used is about 0.00003 mg to about 0.0006 mg. In some embodiments of the methods and uses described herein, the amount or dose, such as the initial dose, of Compound 1, or a corresponding amount of a pharmaceutically acceptable salt thereof, administered or used is about 0.00003 mg to about 0.0009 mg. In some embodiments of the methods and uses described herein, the amount or dose, such as the initial dose, of Compound 1, or a corresponding amount of a pharmaceutically acceptable salt thereof, administered or used is about 0.00003 mg to about 0.0015 mg. In some embodiments of the methods and uses described herein, the amount or dose, such as the initial dose, of Compound 1, or a corresponding amount of a pharmaceutically acceptable salt thereof, administered or used is about 0.00003 mg to about 0.006 mg. In some embodiments of the methods and uses described herein, the amount or dose, such as the initial dose, of Compound 1, or a corresponding amount of a pharmaceutically acceptable salt thereof, administered or used is about 0.00003 mg to about 0.009 mg. In some embodiments of the methods and uses described herein, the amount or dose, such as the initial dose, of Compound 1, or a corresponding amount of a pharmaceutically acceptable salt thereof, administered or used is about 0.00003 mg to about 0.015 mg.

In some embodiments of the methods and uses described herein, the amount or dose, such as the initial dose, of Compound 1, or a corresponding amount of a pharmaceutically acceptable salt thereof, administered or used is about 0.0003 mg to about 0.030 mg. In some embodiments of the methods and uses described herein, the amount or dose, such as the initial dose, of Compound 1, or a corresponding amount of a pharmaceutically acceptable salt thereof, administered or used is about 0.0003 mg to about 0.0006 mg. In some embodiments of the methods and uses described herein, the amount or dose, such as the initial dose, of Compound 1, or a corresponding amount of a pharmaceutically acceptable salt thereof, administered or used is about 0.0003 mg to about 0.0009 mg. In some embodiments of the methods and uses described herein, the amount or dose, such as the initial dose, of Compound 1, or a corresponding amount of a pharmaceutically acceptable salt thereof, administered or used is about 0.0003 mg to about 0.0015 mg. In some embodiments of the methods and uses described herein, the amount or dose, such as the initial dose, of Compound 1, or a corresponding amount of a pharmaceutically acceptable salt thereof, administered or used is about 0.0003 mg to about 0.006 mg. In some embodiments of the methods and uses described herein, the amount or dose, such as the initial dose, of Compound 1, or a corresponding amount of a pharmaceutically acceptable salt thereof, administered or used is about 0.0003 mg to about 0.009 mg. In some embodiments of the methods and uses described herein, the amount or dose, such as the initial dose, of Compound 1, or a corresponding amount of a pharmaceutically acceptable salt thereof, administered or used is about 0.0003 mg to about 0.015 mg.

In some embodiments of the methods and uses described herein, the amount or dose, such as the initial dose, of Compound 1, or a corresponding amount of a pharmaceutically acceptable salt thereof, administered or used is about 0.003 mg to about 0.030 mg. In some embodiments of the methods and uses described herein, the amount or dose, such as the initial dose, of Compound 1, or a corresponding amount of a pharmaceutically acceptable salt thereof, administered or used is about 0.003 mg to about 0.006 mg. In some embodiments of the methods and uses described herein, the amount or dose, such as the initial dose, of Compound 1, or a corresponding amount of a pharmaceutically acceptable salt thereof, administered or used is about 0.003 mg to about 0.009 mg. In some embodiments of the methods and uses described herein, the amount or dose, such as the initial dose, of Compound 1, or a corresponding amount of a pharmaceutically acceptable salt thereof, administered or used is about 0.003 mg to about 0.015 mg.

In some embodiments of the methods and uses described herein, the amount or dose, such as the initial dose, of Compound 1, or a corresponding amount of a pharmaceutically acceptable salt thereof, administered or used is about 0.0003 mg to about 0.003 mg. In some embodiments of the methods and uses described herein, the amount or dose, such as the initial dose, of Compound 1, or a corresponding amount of a pharmaceutically acceptable salt thereof, administered or used is about 0.0006 mg to about 0.003 mg. In some embodiments of the methods and uses described herein, the amount or dose, such as the initial dose, of Compound 1, or a corresponding amount of a pharmaceutically acceptable salt thereof, administered or used is about 0.0009 mg to about 0.003 mg. In some embodiments of the methods and uses described herein, the amount or dose, such as the initial dose, of Compound 1, or a corresponding amount of a pharmaceutically acceptable salt thereof, administered or used is about 0.0015 mg to about 0.003 mg.

In some embodiments of the methods and uses described herein, the amount or dose, such as the initial dose, of Compound 1, or a corresponding amount of a pharmaceutically acceptable salt thereof, administered or used is about 0.00006 mg to about 0.030 mg. In some embodiments of the methods and uses described herein, the amount or dose, such as the initial dose, of Compound 1, or a corresponding amount of a pharmaceutically acceptable salt thereof, administered or used is about 0.00009 mg to about 0.030 mg. In some embodiments of the methods and uses described herein, the amount or dose, such as the initial dose, of Compound 1, or a corresponding amount of a pharmaceutically acceptable salt thereof, administered or used is about 0.00015 mg to about 0.030 mg. In some embodiments of the methods and uses described herein, the amount or dose, such as the initial dose, of Compound 1, or a corresponding amount of a pharmaceutically acceptable salt thereof, administered or used is about 0.0006 mg to about 0.030 mg. In some embodiments of the methods and uses described herein, the amount or dose, such as the initial dose, of Compound 1, or a corresponding amount of a pharmaceutically acceptable salt thereof, administered or used is about 0.0009 mg to about 0.030 mg. In some embodiments of the methods and uses described herein, the amount or dose, such as the initial dose, of Compound 1, or a corresponding amount of a pharmaceutically acceptable salt thereof, administered or used is about 0.0015 mg to about 0.030 mg. In some embodiments of the methods and uses described herein, the amount or dose, such as the initial dose, of Compound 1, or a corresponding amount of a pharmaceutically acceptable salt thereof, administered or used is about 0.006 mg to about 0.030 mg. In some embodiments of the methods and uses described herein, the amount or dose, such as the initial dose, of Compound 1, or a corresponding amount of a pharmaceutically acceptable salt thereof, administered or used is about 0.009 mg to about 0.030 mg. In some embodiments of the methods and uses described herein, the amount or dose, such as the initial dose, of Compound 1, or a corresponding amount of a pharmaceutically acceptable salt thereof, administered or used is about 0.015 mg to about 0.030 mg.

In some embodiments of the methods and uses described herein, the amount or dose, such as the initial dose, of Compound 1, or a corresponding amount of a pharmaceutically acceptable salt thereof, administered or used is about 0.00003 mg. In some embodiments of the methods and uses described herein, the amount or dose, such as the initial dose, of Compound 1, or a corresponding amount of a pharmaceutically acceptable salt thereof, administered or used is about 0.030 mg. In some embodiments of the methods and uses described herein, the amount or dose, such as the initial dose, of Compound 1, or a corresponding amount of a pharmaceutically acceptable salt thereof, administered or used is about 0.0003 mg. In some embodiments of the methods and uses described herein, the amount or dose, such as the initial dose, of Compound 1, or a corresponding amount of a pharmaceutically acceptable salt thereof, administered or used is about 0.003 mg. In some embodiments of the methods and uses described herein, the amount or dose, such as the initial dose, of Compound 1, or a corresponding amount of a pharmaceutically acceptable salt thereof, administered or used is about 0.00005 mg. In some embodiments of the methods and uses described herein, the amount or dose, such as the initial dose, of Compound 1, or a corresponding amount of a pharmaceutically acceptable salt thereof, administered or used is about 0.0005 mg. In some embodiments of the methods and uses described herein, the amount or dose, such as the initial dose, of Compound 1, or a corresponding amount of a pharmaceutically acceptable salt thereof, administered or used is about 0.005 mg. In some embodiments of the methods and uses described herein, the amount or dose, such as the initial dose, of Compound 1, or a corresponding amount of a pharmaceutically acceptable salt thereof, administered or used is about 0.010 mg. In some embodiments of the methods and uses described herein, the amount or dose, such as the initial dose, of Compound 1, or a corresponding amount of a pharmaceutically acceptable salt thereof, administered or used is about 0.0001 mg. In some embodiments of the methods and uses described herein, the amount or dose, such as the initial dose, of Compound 1, or a corresponding amount of a pharmaceutically acceptable salt thereof, administered or used is about 0.001 mg.

Doses of Compound 1, or a corresponding amount of a pharmaceutically acceptable salt therefore, may also be expressed as, for example nmol/kg (e.g., as expressed in Example 11) or µg/kg. For example, 0.003 nmol/kg and 0.03 nmol/kg roughly translate to 0.0037 µg/kg and 0.037 µg/kg of Compound 1 free form, respectively. For a 60 kg woman, the 0.003 nmol/kg dose would be approximately 0.22 µg, or 0.00022 mg, and the 0.03 nmol/kg dose would be 2.2 µg, or 0.0022 mg.

In some embodiments of the methods and uses described herein, the amount or dose of a metabolite of Compound 1, such as Compound 2, or a corresponding amount of a pharmaceutically acceptable salt thereof, administered or used is about 0.00002 mg to about 0.020 mg. In some embodiments of the methods and uses described herein, the amount or dose of a metabolite of Compound 1, such as Compound 2, or a corresponding amount of a pharmaceutically acceptable salt thereof, administered or used is about 0.001 mg to about 5 mg. In some embodiments of the methods and uses described herein, the amount or dose of a metabolite of Compound 1, such as Compound 2, or a corresponding amount of a pharmaceutically acceptable salt thereof, administered or used is about 0.00002 mg to about 0.002 mg. In some embodiments of the methods and uses described herein, the amount or dose of a metabolite of Compound 1, such as Compound 2, or a corresponding amount of a pharmaceutically acceptable salt thereof, administered or used is about 0.0002 mg to about 0.002 mg. In some embodiments of the methods and uses described herein, the amount or dose of a metabolite of Compound 1, such as Compound 2, or a corresponding amount of a pharmaceutically acceptable salt thereof, administered or used is about 0.00002 mg to about 5 mg. In some embodiments of the methods and uses described herein, the amount or dose of a metabolite of Compound 1, such as Compound 2, or a corresponding amount of a pharmaceutically acceptable salt thereof, administered or used is about 0.0002 mg to about 0.020 mg.

Combination Therapies

As briefly described above, Compound 1, a metabolite thereof, or a pharmaceutically acceptable salt of any of the foregoing, may be administered in combination with other agents employed in ART. Such agents may include those used in the COS phase (e.g., FSH, hMG, GnRH agonists or antagonists, and combinations thereof); triggering agents such as GnRH agonists, hCG, and combinations thereof; and hCG, estradiol, a progestogen, such as progesterone, and combinations thereof for luteal phase support prior to embryo transfer, IUI, or intercourse. Compound 1, a metabolite thereof, or a pharmaceutically acceptable salt of any of the foregoing, may also be administered in combination with each other. In some embodiments, multiple sequential doses of Compound 1, a metabolite thereof, or a pharmaceutically acceptable salt of any of the foregoing, may be administered in the methods and uses described herein. Therapeutically effective amounts of agents used in combination may vary depending on the method of administration, the agent selected, and the condition of the female human subject. As used herein, a "therapeutically effective amount" may refer to an amount of a compound sufficient to cause a particular effect (e.g., triggering of oocyte final maturation, support of the endometrium, etc.).

Administration of these agents in combination typically is carried out over a defined time period (usually minutes, hours, days or weeks depending upon the combination selected). In certain embodiments, agents are administered in a sequential manner, that is, wherein each agent is administered at a different time, as well as administration of these agents, or at least two of the agents, in a substantially simultaneous manner. Substantially simultaneous administration may be accomplished, for example, by administering to the human female subject a single injection having a fixed ratio of each agent or in multiple, single injections for each of the agents. Sequential or substantially simultaneous administration of each agent may be effected by any appropriate route including, but not limited to, oral routes, intravenous routes, subcutaneous, intramuscular routes, and direct absorption through mucous membrane tissues. The agents may be administered by the same route or by different routes. Alternatively, for example, all therapeutic agents may be administered by intravenous injection. When injected, Compound 1, a metabolite thereof, or a pharmaceutically acceptable salt of any of the foregoing, may be combined with other agents employed in ART in order to reduce the number of injections given to a patient.

Compound 1, a metabolite thereof, or a pharmaceutically acceptable salt of any of the foregoing, may be used in combination with a number of therapies included in ART. These therapies, include but are not limited to, those used in the COS phase of the ART process (e.g., follicle growth agents, such as FSH, hMG, and the like that are used to stimulate oocyte development and growth and GnRH agonists or antagonists that are used to control ovarian stimulation and prevent premature ovulation or combinations of any of the foregoing).

In some embodiments of the methods and uses described herein, FSH is administered prior to administration of the initial dose of Compound 1, a metabolite thereof, or a pharmaceutically acceptable salt of any of the foregoing. In some embodiments of the methods and uses described herein, FSH is administered about 5 days to about 12 days prior to administration of the initial dose of Compound 1, a metabolite thereof, or a pharmaceutically acceptable salt of any of the foregoing. In certain such embodiments, administration of FSH is about 5 days, about 6 days, about 7 days, about 8 days, about 9 days, about 10 days, about 11 days, or about 12 days prior to administration of the initial dose of Compound 1, a metabolite thereof, or a pharmaceutically acceptable salt of any of the foregoing.

In some embodiments of the methods and uses described herein, a GnRH antagonist is administered prior to administration of the initial dose of Compound 1, a metabolite thereof, or a pharmaceutically acceptable salt of any of the foregoing. In some embodiments of the methods and uses described herein, a GnRH antagonist is administered about 2 days to about 10 days prior to administration of the initial dose of Compound 1, a metabolite thereof, or a pharmaceutically acceptable salt of any of the foregoing, such as about 3 days to about 5 days prior to administration of the initial dose of Compound 1, a metabolite thereof, or a pharmaceutically acceptable salt of any of the foregoing. In certain such embodiments, administration of the GnRH antagonist is about 2 days, about 3 days, about 4 days, about 5 days, about 6 days, about 7 days, about 8 days, about 9 days, or about 10 days prior to administration of the initial dose of Compound 1, a metabolite thereof, or a pharmaceutically acceptable salt of any of the foregoing.

In some embodiments of the methods and uses described herein, a GnRH agonist is administered prior to administration of the initial dose of Compound 1, a metabolite thereof, or a pharmaceutically acceptable salt of any of the foregoing. In some embodiments of the methods and uses described herein, a GnRH agonist is administered about 14 days to about 28 days prior to administration of the initial dose of Compound 1, a metabolite thereof, or a pharmaceutically acceptable salt of any of the foregoing, such as about 14 days to about 17 days prior to administration of the initial dose of Compound 1, a metabolite thereof, or a pharmaceutically acceptable salt of any of the foregoing. In certain such embodiments, administration of the GnRH agonist is about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days prior to administration of the initial dose of Compound 1, a metabolite thereof, or a pharmaceutically acceptable salt of any of the foregoing.

As to the GnRH agonists previously referred to that may be used in combination with Compound 1, a metabolite thereof, or a pharmaceutically acceptable salt of any of the foregoing, in ART during the COS phase to prevent premature ovulation, these agents include the following: a GnRH (gonadotropin-releasing hormone) superactive agonist such as leuprorelin acetate, gonadorelin, buserelin, triptorelin, goserelin, nafarelin, histrelin, deslorelin, meterelin, lecirelin, or pharmaceutically acceptable salts of any of the foregoing, and the like; or a GnRH antagonist such as cetrorelix, ganirelix, abarelix, nal-blu, antide, azaline B, degarelix, D63153 (ozarelix), OBE2109, teverelix, elagolix, relugolix, or pharmaceutically acceptable salts of any of the foregoing, and the like. In some embodiments during the COS phase to prevent premature ovulation, the GnRH agonist is leuprorelin acetate.

In some embodiments during the COS phase to prevent premature ovulation, the GnRH antagonist may be relugolix, or a pharmaceutically acceptable salt thereof. Relugolix is N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea and is represented by the formula:

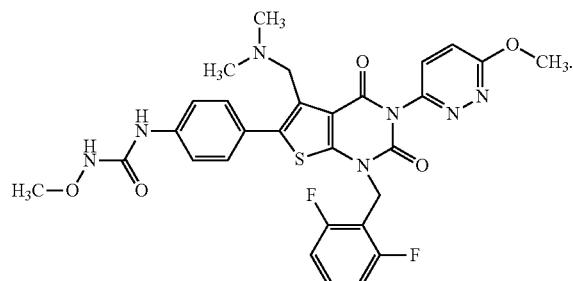

Relugolix is orally active and antagonizes GnRH through the GnRH receptors that are present in the pituitary anterior lobe basophiles (secretory cells), and inhibits the GnRH-stimulated secretion of LH and FSH from these cells. In some embodiments of the methods and uses described herein, the dose of relugolix, or a corresponding amount of a pharmaceutically acceptable salt thereof, is about 20 mg to about 120 mg, such as 80 mg. In some embodiments of the methods and uses described herein, the dose of relugolix, or a corresponding amount of a pharmaceutically acceptable salt thereof, is less than about 20 mg, less than about 40 mg, less than about 80 mg, or less than about 120 mg.

Relugolix, or a pharmaceutically acceptable salt thereof, is an orally-available GnRH antagonist that may be useful in the COS phase of ART when used with FSH or FSH/hMG, to prevent premature ovulation by suppressing the naturally-occurring LH surge. This then may allow the use of Compound 1, a metabolite thereof, or a pharmaceutically acceptable salt of any of the foregoing, as a trigger to promote oocyte maturation for subsequent retrieval, fertilization (in vitro), ET, ICSI, oocyte donation and banking, intercourse or IUI, or ovulation induction.

Relugolix, when used in combination with Compound 1, a metabolite thereof, or a pharmaceutically acceptable salt of any of the foregoing (as the trigger agent), may lower rates of OHSS, increase pregnancy rates, and shorten time to pregnancy compared to when GnRH agonists are administered instead of relugolix. Additionally, in some embodiments, a formulation for injection comprising Compound 1, a metabolite thereof, or a pharmaceutically acceptable salt of any of the foregoing, may be used with oral FSH and an oral GnRH antagonist, such as relugolix, possibly making the ART cycle predominantly oral versus the current protocol comprising many injections.

Compound 1, a metabolite thereof, or a pharmaceutically acceptable salt of any of the foregoing, may also be used with other triggering agents for oocyte maturation (i.e., oocyte maturation agents). In some embodiments of the methods and uses described herein, the initial dose of Compound 1, a metabolite thereof, or a pharmaceutically acceptable salt of any of the foregoing, may be administered after administration of a GnRH agonist as an oocyte maturation agent. In some embodiments of the methods and uses described herein, the initial dose of Compound 1, a metabolite thereof, or a pharmaceutically acceptable salt of any of the foregoing, may be administered at the same time as administration of a GnRH agonist as an oocyte maturation agent. In some embodiments of the methods and uses described herein, the initial dose of Compound 1, a metabolite thereof, or a pharmaceutically acceptable salt of any of the foregoing, may be administered before administration of a GnRH agonist as an oocyte maturation agent. In some embodiments, the GnRH agonist is selected from the group consisting of leuprorelin acetate, gonadorelin, buserelin, triptorelin, goserelin, nafarelin, histrelin, deslorelin, meterelin, lecirelin, or pharmaceutically acceptable salts of any of the foregoing. In some embodiments, oocyte maturation occurs after administration of a GnRH agonist. In certain such embodiments, the yield of mature oocytes is at least 50%. In certain such embodiments, the yield of mature oocytes is at least 75%. As noted above, oocyte yield may refer to the percentage of mature oocytes collected from the number of follicles 14 mm on final ultrasound scan prior to trigger administration. The disclosure provides that when Compound 1, a metabolite thereof, or a pharmaceutically acceptable salt of any of the foregoing, is administered in combination with a GnRH agonist as an oocyte maturation agent, the human female subject may not experience a worsening of one or more symptoms of OHSS. The disclosure also provides that when Compound 1, a metabolite thereof, or a pharmaceutically acceptable salt of any of the foregoing, is administered in combination with a GnRH agonist as an oocyte maturation agent, one or more symptoms of OHSS may be treated.

Compound 1, a metabolite thereof, or a pharmaceutically acceptable salt of any of the foregoing, may be used with hCG as an oocyte maturation agent. In some embodiments, hCG is administered at the same time as administration of Compound 1, a metabolite thereof, or a pharmaceutically acceptable salt of any of the foregoing. In some embodiments, hCG is administered before administration of Compound 1, a metabolite thereof, or a pharmaceutically acceptable salt of any of the foregoing. In some embodiments, hCG is administered after administration of Compound 1, a metabolite thereof, or a pharmaceutically acceptable salt of any of the foregoing. In some embodiments, hCG is administered within 24 hours of administration of Compound 1, a metabolite thereof, or a pharmaceutically acceptable salt of any of the foregoing. In some embodiments, hCG is administered within 48 hours of administration of Compound 1, a metabolite thereof, or a pharmaceutically acceptable salt of any of the foregoing. Ovulation will occur between 38 and 40 hours after a single hCG injection and trans-vaginal oocyte retrieval is typically performed between 34 and 36 hours after hCG injection, just prior to when the follicles would rupture. In certain embodiments, oocyte maturation occurs after administration of exogenous hCG. In certain such embodiments, the yield of mature oocytes is at least 50%. In certain such embodiments, the yield of mature oocytes is at least 75%. As noted above, oocyte yield may refer to the percentage of mature oocytes collected from the number of follicles 14 mm on final ultrasound scan prior to trigger administration. The disclosure provides that when Compound 1, a metabolite thereof, or a pharmaceutically acceptable salt of any of the foregoing, is administered in combination with hCG as an oocyte maturation agent, the human female subject may not experience a worsening of one or more symptoms of OHSS. The disclosure also provides that when Compound 1, a metabolite thereof, or a pharmaceutically acceptable salt of any of the foregoing, is administered in combination with hCG as an oocyte maturation agent, one or more symptoms of OHSS may be treated. In some embodiments, hCG used in ART may be recombinant or urine-derived.

In some embodiments of the methods and uses described herein, recombinant luteinizing hormone (rLH) may be used to achieve oocyte maturation. In certain such embodiments, rLH is administered at the same time as Compound 1, a metabolite thereof, or a pharmaceutically acceptable salt of any of the foregoing. In some embodiments, rLH is administered after Compound 1, a metabolite thereof, or a pharmaceutically acceptable salt of any of the foregoing. In some embodiments, rLH is administered before Compound 1, a metabolite thereof, or a pharmaceutically acceptable salt of any of the foregoing.

The disclosure provides for use of Compound 1, a metabolite thereof, or a pharmaceutically acceptable salt of any of the foregoing, with both a GnRH agonist and hCG in combination as oocyte maturation agents. In some embodiments, Compound 1, a metabolite thereof, or a pharmaceutically acceptable salt of any of the foregoing, is administered at the same time as the GnRH agonist and hCG. In some embodiments, Compound 1, a metabolite thereof, or a pharmaceutically acceptable salt of any of the foregoing, is administered at before the GnRH agonist and hCG. In some embodiments, Compound 1, a metabolite thereof, or a pharmaceutically acceptable salt of any of the foregoing, is administered after the GnRH agonist and hCG.

In some embodiments of the methods and uses described herein, Compound 1, or a pharmaceutically acceptable salt thereof, is used in combination with a metabolite of Compound 1, such as Compound 2, or a pharmaceutically acceptable salt thereof, as oocyte maturation agents. In certain embodiments of the methods and uses described herein, multiple doses of Compound 1, or a pharmaceutically acceptable salt thereof, for example, two doses, are used for oocyte maturation. In certain embodiments of the methods and uses described herein, multiple doses of a metabolite of Compound 1, such as Compound 2, or a pharmaceutically acceptable salt thereof, for example, two doses, are used for oocyte maturation.

In addition, Compound 1, a metabolite thereof, or a pharmaceutically acceptable salt of any of the foregoing, may be used in an ET process, with intercourse or IUI, or in ovulation induction in combination with a promoter for implantation or pregnancy such as luteal phase support with estradiol, a progestogen, such as progesterone, low dose hCG, or combinations thereof. In some embodiments of the methods and uses described herein, a combination of estradiol and a progestogen, such as progesterone, are administered for luteal phase support. In some embodiments of the methods and uses described herein, a progestogen, such as progesterone, is administered in combination with Compound 1, a metabolite thereof, or a pharmaceutically acceptable salt of any of the foregoing, for luteal phase support. In some embodiments of the methods and uses described herein, estradiol is administered in combination with Compound 1, a metabolite thereof, or a pharmaceutically acceptable salt of any of the foregoing, for luteal phase support. In some embodiments of the methods and uses described herein, estradiol and a progestogen, such as progesterone, are administered in combination with Compound 1, a metabolite thereof, or a pharmaceutically acceptable salt of any of the foregoing, for luteal phase support. In some embodiments of the methods and uses described herein, one or more doses of a progestogen, such as progesterone, are administered for luteal phase support. In certain embodiments, a progestogen, such as progesterone, may be administered from oocyte retrieval until up to 12 weeks after retrieval. In some embodiments, a progestogen, such as progesterone, may be administered at oocyte retrieval. In some embodiments, a progestogen, such as progesterone, may be administered from oocyte retrieval until one week after retrieval. In some embodiments, a progestogen, such as progesterone, may be administered from oocyte retrieval until two weeks after retrieval. In some embodiments, a progestogen, such as progesterone, may be administered from oocyte retrieval until three weeks after retrieval. In some embodiments, a progestogen, such as progesterone, may be administered from oocyte retrieval until four weeks after retrieval. In some embodiments, a progestogen, such as progesterone, may be administered from oocyte retrieval until five weeks after retrieval. In some embodiments, a progestogen, such as progesterone, may be administered from oocyte retrieval until six weeks after retrieval. In some embodiments, a progestogen, such as progesterone, may be administered from oocyte retrieval until seven weeks after retrieval. In some embodiments, a progestogen, such as progesterone, may be administered from oocyte retrieval until eight weeks after retrieval. In some embodiments, a progestogen, such as progesterone, may be administered from oocyte retrieval until nine weeks after retrieval. In some embodiments, a progestogen, such as progesterone, may be administered from oocyte retrieval until ten weeks after retrieval. In some embodiments, a progestogen, such as progesterone, may be administered from oocyte retrieval until eleven weeks after retrieval.

In some embodiments of the methods and uses described herein, a progestogen, such as progesterone, is administered for luteal support after administration of a Compound 1, a metabolite thereof, or a pharmaceutically acceptable salt of any of the foregoing, trigger. In some embodiments of the methods and uses described herein, estradiol is administered for luteal support after administration of a Compound 1, a metabolite thereof, or a pharmaceutically acceptable salt of any of the foregoing, trigger. In some embodiments of the methods and uses described herein, a progestogen, such as progesterone, and estradiol are administered for luteal support after administration of Compound 1, a metabolite thereof, or a pharmaceutically acceptable salt of any of the foregoing, trigger.

For luteal phase support, in some embodiments, the methods and uses described herein provide for use of natural preparations of progesterone (P4), including dydrogesterone, medrogesterone, and progesterone itself. In some embodiments of the methods and uses described herein, P4 may be administered orally, intramuscularly (IM), or vaginally. An IM progestogen, such as progesterone, may be prepared in sesame oil, coconut oil, or peanut oil and the dosage is 50 mg once daily. There are several vaginal formulations of a progestogen, such as progesterone, including gels, suppositories, and inserts. Prometrium® may be used as a vaginal preparation, with a recommended dose of 200 mg inserted vaginally 3 times a day. The vaginal gel Crinone® 8% (Columbia Laboratories Inc.; Livingston, N.J.) may be applied once a day and contains 90 mg of a progestogen, such as progesterone. One-hundred milligrams of Endometrin® (Ferring Pharmaceuticals Inc.; Suffern, N.Y.) may be administered vaginally 2 or 3 times daily.

In certain embodiments of the methods and uses described herein, low dose hCG is administered for luteal phase support. In some embodiments of the methods and uses described herein, low dose hCG is administered for luteal phase support after a Compound 1, a metabolite thereof, or a pharmaceutically acceptable salt of any of the foregoing, trigger. In certain embodiments of the methods and uses described herein, low dose hCG is administered in combination with a progestogen, such as progesterone, for luteal phase support after a Compound 1, a metabolite thereof, or a pharmaceutically acceptable salt of any of the foregoing, trigger. In certain embodiments of the methods and uses described herein, low dose hCG is administered in combination with estradiol for luteal phase support after a Compound 1, a metabolite thereof, or a pharmaceutically acceptable salt of any of the foregoing, trigger. In certain embodiments of the methods and uses described herein, low dose hCG is administered in combination with a progestogen, such as progesterone, and estradiol for luteal phase support after a Compound 1, a metabolite thereof, or a pharmaceutically acceptable salt of any of the foregoing, trigger.

In some embodiments of the methods and uses described herein, low dose hCG is administered in combination with Compound 1, a metabolite thereof, or a pharmaceutically acceptable salt of any of the foregoing, for luteal phase support. In certain embodiments of the methods and uses described herein, low dose hCG is administered in combination with Compound 1, a metabolite thereof, or a pharmaceutically acceptable salt of any of the foregoing, and a progestogen, such as progesterone, for luteal phase support. In certain embodiments of the methods and uses described herein, low dose hCG is administered in combination with Compound 1, a metabolite thereof, or a pharmaceutically acceptable salt of any of the foregoing, and estradiol for luteal phase support. In certain embodiments of the methods and uses described herein, low dose hCG is administered in combination with Compound 1, a metabolite thereof, or a pharmaceutically acceptable salt of any of the foregoing, a progestogen, such as progesterone, and estradiol for luteal phase support.

In some embodiments, Compound 1, a metabolite thereof, or a pharmaceutically acceptable salt of any of the foregoing, is administered for luteal support after a woman receives an hCG trigger. In some embodiments, Compound 1, a metabolite thereof, or a pharmaceutically acceptable salt of any of the foregoing, is administered for luteal support after a woman receives a GnRH agonist trigger. In some embodiments, Compound 1, a metabolite thereof, or a pharmaceutically acceptable salt of any of the foregoing, is administered for luteal support after a woman receives both hCG and a GnRH agonist trigger. In some embodiments, Compound 1, a metabolite thereof, or a pharmaceutically acceptable salt of any of the foregoing, is administered for luteal support after a woman receives a Compound 1, a metabolite thereof, or a pharmaceutically acceptable salt of any of the foregoing, trigger. In some embodiments, Compound 1, a metabolite thereof, or a pharmaceutically acceptable salt of any of the foregoing, is administered for luteal support after a woman receives both a GnRH agonist trigger and a Compound 1, a metabolite thereof, or a pharmaceutically acceptable salt of any of the foregoing, trigger. In some embodiments, Compound 1, a metabolite thereof, or a pharmaceutically acceptable salt of any of the foregoing, is administered for luteal support after a woman receives both an hCG trigger and a Compound 1, a metabolite thereof, or a pharmaceutically acceptable salt of any of the foregoing, trigger. In some embodiments, Compound 1, a metabolite thereof, or a pharmaceutically acceptable salt of any of the foregoing, is administered for luteal support after a woman receives an hCG trigger, a GnRH agonist trigger, and a Compound 1, a metabolite thereof, or a pharmaceutically acceptable salt of any of the foregoing, trigger.

In some embodiments of the methods and uses described herein, Compound 1, or a pharmaceutically acceptable salt thereof, is used in combination with a metabolite of Compound 1, such as Compound 2, or a pharmaceutically acceptable salt thereof, for luteal phase support. In certain embodiments of the methods and uses described herein, multiple doses of Compound 1, or a pharmaceutically acceptable salt thereof, for example, two doses, are used for luteal phase support. In certain embodiments of the methods and uses described herein, multiple doses of a metabolite of Compound 1, such as Compound 2, or a pharmaceutically acceptable salt thereof, for example, two doses, are used for luteal phase support.

An advantage of Compound 1, or a pharmaceutically acceptable salt thereof, is that it may be used not only as a trigger for ovulation, but may be re-administered one or more times to provide additional LH for luteal phase support. This may reduce the need for progesterone injections and supplementation. Current ART protocols typically use a GnRH agonist trigger followed by low dose hCG for luteal phase support, but this increases the risk of OHSS. Administration of one or more doses of Compound 1, or a pharmaceutically acceptable salt thereof, may reduce the risk of OHSS present in current ART protocols and act as a trigger for oocyte maturation and/or as luteal phase support. Multiple doses of Compound 1, or a pharmaceutically acceptable salt thereof, may reduce the risk of OHSS by preventing an increase in serum VEGF, thus, reducing vascular permeability.

In some embodiments, Compound 1, a metabolite thereof, or a pharmaceutically acceptable salt of any of the foregoing, is administered in combination with a protease inhibitor. In certain such embodiments, administration of Compound 1, a metabolite thereof, or a pharmaceutically acceptable salt of any of the foregoing, in combination with a protease inhibitor is for luteal phase support. In certain such embodiments, the formulation administered comprises both Compound 1, a metabolite thereof, or a pharmaceutically acceptable salt of any of the foregoing, and a protease inhibitor. In some embodiments, the formulation comprising both Compound 1, a metabolite thereof, or a pharmaceutically acceptable salt of any of the foregoing, and a protease inhibitor is immediate release, extended or sustained release, or delayed release. In certain such embodiments, the formulation may exhibit an immediate release profile. In some embodiments, the formulation comprising both Compound 1, a metabolite thereof, or a pharmaceutically acceptable salt of any of the foregoing, and a protease inhibitor may exhibit an extended or sustained release profile. In some embodiments, the formulation comprising both Compound 1, a metabolite thereof, or a pharmaceutically acceptable salt of any of the foregoing, and a protease inhibitor may exhibit a delayed release profile. In some embodiments, the formulation comprising Compound 1, a metabolite thereof, or a pharmaceutically acceptable salt of any of the foregoing, is administered separately than the formulation comprising a protease inhibitor. Possible protease inhibitors that may be used in the methods and uses of the disclosure include, but are not limited to, 4-(2-aminoethyl) benzenesulfonyl fluoride hydrochloride (AEBSF), EDTA, bestatin, E-64, leupeptin, such as leupeptin hemisulfate monohydrate, aprotinin, (2S, 3S)-3-carboxyoxirane-2-carbonyl]-leucine (4-guanidinobutyl)amide hemihydrate, and salts of any of the foregoing.

Formulations, Dosing, and Administration

The disclosure provides formulations or pharmaceutical compositions comprising Compound 1, a metabolite thereof, or a pharmaceutically acceptable salt of any of the foregoing, and a pharmaceutically acceptable excipient or carrier for use in the methods and uses disclosed herein. In ART, Compound 1, a metabolite thereof, or a pharmaceutically acceptable salt of any of the foregoing, may be administered as a formulation or pharmaceutical composition with one or more pharmaceutically acceptable carriers or excipients.

The amount of Compound 1, a metabolite thereof, or a pharmaceutically acceptable salt of any of the foregoing, administered may vary according to the weight, age, and medical condition of the human female subject. Therapeutically effective amounts of Compound 1, a metabolite thereof, or a pharmaceutically acceptable salt of any of the foregoing, used herein may vary depending on the method of administration, the agent selected, and the condition of the female human subject.

Compound 1, or a pharmaceutically acceptable salt thereof, is stable and may be stored at 4° C. versus many peptide drugs which must be stored and reconstituted at −20° C.

Formulations of the disclosure may be formulated for differing rates of release, such as immediate release, extended or sustained release, or delayed release. In some embodiments, the formulations may exhibit an immediate release profile. In some embodiments, the formulations may exhibit an extended or sustained release profile. In some embodiments, the formulations may exhibit a delayed release profile.

The carrier or excipients of the formulations of the disclosure may be a blend of excipients, and amounts, which may optimize the efficacy of the formulation. Excipients include, for example, various organic or inorganic excipients or carrier substances.

Formulations comprising Compound 1, a metabolite thereof, or a pharmaceutically acceptable salt of any of the foregoing, may be administered via injection, e.g., intravenously (IV), intramuscularly (IM) or subcutaneously (SC). In some embodiments, the injection is IM. In other embodiments, the injection is SC. In some embodiments, the SC injection is a bolus. In some embodiments, the SC injection is an infusion. Injection typically entails delivery of a discrete amount of a liquid composition with a hypodermic needle and a syringe or other injection devices known in the art. Examples of injection may also include infusion and intravenous devices. Injection may take place immediately or over a period of time.

An injectable dosage formulation comprising Compound 1, a metabolite thereof, or a pharmaceutically acceptable salt of any of the foregoing, may be based on water or oil as a vehicle or carrier. Examples of vehicles or carriers include, but are not limited to, water for injection, alcohol, propylene glycol, macrogol, sesame oil, corn oil, olive oil, vegetable oil, cottonseed oil, corn oil, etc. In some embodiments, the vehicle or carrier is water for injection. Alternately, the injectable dosage formulation may take the form of an emulsion, suspension, or solution. The injectable dosage formulation may have other ingredients, such as dispersing agents, dissolution aids, suspending agents, stabilizers, surfactants, solubilizing agents, surfactants, buffering agents, isotonizing agents, pH adjusting agents, and soothing agents. Suitable dispersing agents include, but are not limited to, Tween 80® (Atlas Powder Company USA), HCO 60™ (Nikko Chemicals Co., Ltd.), polyethylene glycol, carboxymethyl cellulose, sodium alginate, hydroxypropylmethyl cellulose, dextrose, and dextrin. In some embodiments, the dispersing agent is dextrose. Suitable stabilizers include, but are not limited to, ascorbic acid and sodium pyrosulfite. Suitable surfactants include, but are not limited to, polysorbate 80 and macrogol. Suitable solubilizing agents include, but are not limited to, glycerin and ethanol. Suitable buffering agents include, but are not limited to, phosphoric acid or its alkali metal salts, citric acid or its alkali metal salts, acetates, and carbonates. Suitable isotonizing agents include, but are not limited to, sodium chloride, glycerine, potassium chloride, mannitol, sorbitol, glycerol, and glucose. In some embodiments, the isotonizing agent is mannitol. Suitable pH adjusting agents include, but are not limited to, hydrochloric acid, acetic acid, and sodium hydroxide. In some embodiments, the pH adjusting agent is acetic acid. Suitable preservatives include, but are not limited to, ethyl p-oxybenzoate, benzoic acid, methylparabene, propylparabene, and benzyl alcohol. Suitable solubilizers include, but are not limited to, concentrated glycerin and meglumine. Suitable dissolution aids include, but are not limited to, propylene glycol and saccharose. Suitable soothing agents include, but are not limited to, glucose and benzyl alcohol. Examples of dissolution aids include polyethylene glycol, propylene glycol, D-mannitol, benzyl benzoate, ethanol, trisaminomethane, cholesterol, triethanolamine, sodium carbonate, sodium citrate, etc. Examples of suspending agents include surfactants such as stearyl triethanolamine, sodium laurylsulfate, lauryl aminopropionate, lecithin, benzalkonium chloride, benzethonium chloride, glycerine monostearate, etc.; hydrophilic polymers such as polyvinyl alcohol, polyvinyl pyrrolidone, sodium carboxymethylcellulose, methylcellulose, hydroxymethylcellulose, hydroxyethylcellulose, hydroxypropylcellulose, etc. Other excipients that may be used include, for example, lactose, sucrose, starch, cornstarch, crystalline cellulose, silicic anhydride, light anhydrous silicic acid, and the like.

Other additives, such as preservatives, antioxidants, and coloring agents, may also be used. Possible preservatives include, but are not limited to, paraoxybenzoic acid ester, chlorobutanol, benzyl alcohol, phenethyl alcohol, dehydroacetic acid, sorbic acid, and the like. Possible antioxidants include, but are not limited to, sulfite, ascorbic acid, and the like. Possible coloring agents include, but are not limited to, ferric oxides.

In some embodiments, the injectable formulation of the disclosure comprises Compound 1, a metabolite thereof, or a pharmaceutically acceptable salt of any of the foregoing, mannitol, acetic acid, and water for injection. In certain such embodiments, the formulation further comprises glucose and/or dextrose.

In some embodiments, the injectable formulation of the disclosure may be adjusted to pH of 2 to 12, preferably 2.5 to 8.0 by adding a pH adjusting-agent.

The amount administered in the injectable dosage formulation may be effective to promote egg maturation in ART, such as IVF, ICSI, oocyte donation and banking, regulation of a menstrual cycle so a human female subject may conceive via intercourse or IUI, ovulation induction, and/or an ET process. In some embodiments, injectable formulations of the disclosure may be administered as a single dose. In some embodiments, injections may be carried out when release and retrieval of mature oocytes is desired, such as during the trigger phase, prior to oocyte retrieval from the ovaries, IVF, ICSI, oocyte donation and banking, regulation of a menstrual cycle so a human female subject may conceive via intercourse or IUI, and implantation of fertilized embryo into the uterus. In some embodiments, injectable formulations of the disclosure may be administered as a single dose. In some embodiments, injectable formulations of the disclosure may be administered as a divided dose. In some embodiments, two doses of an injectable formulation of the disclosure may be administered. In some embodiments, the second injectable dose is administered within about 8 to about 60 hours after administration of the initial dose. In some embodiments, three doses of an injectable formulation of the disclosure may be administered. In some embodiments, the third injectable dose is administered within about 8 to about 60 hours after administration of the second dose. In some embodiments, a third injectable dose is administered and is followed by administration of one to five additional injectable doses. In some embodiments wherein a third injectable dose is administered and is followed by administration of one to five additional injectable doses, the administration of the one to five additional doses is within about 8 to about 60 hours after the prior dose is administered.

Compound 1, a metabolite thereof, or a pharmaceutically acceptable salt of any of the foregoing, may also be administered in a depot formulation. Injectable depot forms may be made by forming microencapsulated matrices of the drug in biodegradable polymers such as polylactide-polyglycolide, poly(orthoesters), poly(anhydrides), and (poly)glycols, such as PEG. Depending upon the ratio of drug to polymer and the nature of the particular polymer employed, the rate of drug release may be controlled. Depot injectable formulations may also be prepared by entrapping the drug in liposomes or microemulsions which are compatible with body tissues.

The injectable formulations of the disclosure may be sterilized, for example, by filtration through a bacterial-retaining filter, or by incorporating sterilizing agents in the form of sterile solid compositions which may be dissolved or dispersed in sterile water or other sterile injectable medium just prior to use.

Compound 1, a metabolite thereof, or a pharmaceutically acceptable salt of any of the foregoing, may also be administered in an intranasal formulation. The formulation may take the form of a liquid so that it may be sprayed into the nostrils, although a semi-solid formulation, such as an intranasal cream, may be possible. Liquid intranasal formulations may take the form of a solution, suspension, or emulsion and may be aqueous or non-aqueous. The ingredients listed above for the injectable dosage form may also be employed according to methods known in the art to prepare an intranasal formulation.

The amount of Compound 1, a metabolite thereof, or a pharmaceutically acceptable salt of any of the foregoing, administered intranasally may be effective to promote egg maturation in ART, such as IVF, ICSI, oocyte donation and banking, regulation of a menstrual cycle so a human female subject may conceive via intercourse or IUI, ovulation induction, and/or an ET process. In some embodiments, intranasal formulations of the disclosure may be administered in a single dose. In some embodiments, intranasal administration may be carried out when release and retrieval of mature oocytes is desired, such as during the trigger phase, prior to oocyte retrieval from the ovaries, IVF, ICSI, oocyte donation and banking, regulation of a menstrual cycle so a human female subject may conceive via intercourse or IUI, and implantation of fertilized embryo into the uterus. In some embodiments, the intranasal formulations of the disclosure may be administered in a single dose. In some embodiments, the intranasal formulations of the disclosure may be administered in a divided dose. In some embodiments, two doses of an intranasal formulation of the disclosure may be administered. In some embodiments, the second intranasal dose is administered within about 8 to about 60 hours after administration of the initial dose. In some embodiments, three doses of an intranasal formulation of the disclosure may be administered. In some embodiments, the third intranasal dose is administered within about 8 to about 60 hours after administration of the second dose. In some embodiments, a third intranasal dose is administered and is followed by administration of one to five additional intranasal doses. In some embodiments wherein a third intranasal dose is administered and is followed by administration of one to five additional intranasal doses, the administration of the one to five additional doses is within about 8 to about 60 hours after the prior dose is administered.

In addition, conventional additives such as a preservative, an antioxidant, a colorant, a sweetener, an adsorbent, a wetting agent, etc. may be appropriately used in suitable amounts, in all dosage forms if necessary. Possible preservatives include, for example, p-hydroxybenzoates, paraoxybenzoic acid ester, chlorobutanol, benzyl alcohol, phenethyl alcohol, dehydroacetic acid, sorbic acid, ethyl p-oxybenzoate, benzoic acid, methylparabene, propylparabene, and the like. Possible antioxidants include, for example, sulfite, ascorbic acid, α-tocopherol, and the like.

Dosage forms containing Compound 1, and pharmaceutically acceptable salts thereof, are disclosed, for example, in U.S. Patent Application Publication Nos. 2012/0302508, 2013/0210742, 2011/0312898, and 2011/0212890, the disclosures of which are herein incorporated by reference. The publications also disclose various indications and end uses for Compound 1.

In some embodiments, formulations or pharmaceutical compositions of the disclosure comprise about 0.00003 mg to about 0.030 mg of Compound 1, or a corresponding amount of a pharmaceutically acceptable salt thereof. In some embodiments, formulations or pharmaceutical compositions of the disclosure comprise about 0.001 mg to about 0.030 mg of Compound 1, or a corresponding amount of a pharmaceutically acceptable salt thereof. In some embodiments, formulations or pharmaceutical compositions of the disclosure comprise about 0.001 mg to about 0.003 mg of Compound 1, or a corresponding amount of a pharmaceutically acceptable salt thereof. In some embodiments, formulations or pharmaceutical compositions of the disclosure comprise about 0.00003 mg to about 0.0003 mg of Compound 1, or a corresponding amount of a pharmaceutically acceptable salt thereof. In some embodiments, formulations or pharmaceutical compositions of the disclosure comprise about 0.00003 mg to about 0.003 mg of Compound 1, or a corresponding amount of a pharmaceutically acceptable salt thereof. In some embodiments, formulations or pharmaceutical compositions of the disclosure comprise about 0.00003 mg to about 0.00006 mg of Compound 1, or a corresponding amount of a pharmaceutically acceptable salt thereof. In some embodiments, formulations or pharmaceutical compositions of the disclosure comprise about 0.00003 mg to about 0.00009 mg of Compound 1, or a corresponding amount of a pharmaceutically acceptable salt thereof. In some embodiments, formulations or pharmaceutical compositions of the disclosure comprise about 0.00003 mg to about 0.00015 mg of Compound 1, or a corresponding amount of a pharmaceutically acceptable salt thereof. In some embodiments, formulations or pharmaceutical compositions of the disclosure comprise about 0.00003 mg to about 0.0006 mg of Compound 1, or a corresponding amount of a pharmaceutically acceptable salt thereof. In some embodiments, formulations or pharmaceutical compositions of the disclosure comprise about 0.00003 mg to about 0.0009 mg of Compound 1, or a corresponding amount of a pharmaceutically acceptable salt thereof. In some embodiments, formulations or pharmaceutical compositions of the disclosure comprise about 0.00003 mg to about 0.0015 mg of Compound 1, or a corresponding amount of a pharmaceutically acceptable salt thereof. In some embodiments, formulations or pharmaceutical compositions of the disclosure comprise about 0.00003 mg to about 0.006 mg of Compound 1, or a corresponding amount of a pharmaceutically acceptable salt thereof. In some embodiments, formulations or pharmaceutical compositions of the disclosure comprise about 0.00003 mg to about 0.009 mg of Compound 1, or a corresponding amount of a pharmaceutically acceptable salt thereof. In some embodiments, formulations or pharmaceutical compositions of the disclosure comprise about 0.00003 mg to about 0.015 mg of Compound 1, or a corresponding amount of a pharmaceutically acceptable salt thereof.

In some embodiments, formulations or pharmaceutical compositions of the disclosure comprise about 0.0003 mg to about 0.030 mg of Compound 1, or a corresponding amount of a pharmaceutically acceptable salt thereof. In some embodiments, formulations or pharmaceutical compositions of the disclosure comprise about 0.0003 mg to about 0.0006 mg of Compound 1, or a corresponding amount of a pharmaceutically acceptable salt thereof. In some embodiments, formulations or pharmaceutical compositions of the disclosure comprise about 0.0003 mg to about 0.0009 mg of Compound 1, or a corresponding amount of a pharmaceutically acceptable salt thereof. In some embodiments, formulations or pharmaceutical compositions of the disclosure comprise about 0.0003 mg to about 0.0015 mg of Compound 1, or a corresponding amount of a pharmaceutically acceptable salt thereof. In some embodiments, formulations or pharmaceutical compositions of the disclosure comprise about 0.0003 mg to about 0.006 mg of Compound 1, or a corresponding amount of a pharmaceutically acceptable salt thereof. In some embodiments, formulations or pharmaceutical compositions of the disclosure comprise about 0.0003 mg to about 0.009 mg of Compound 1, or a corresponding amount of a pharmaceutically acceptable salt thereof. In some embodiments, formulations or pharmaceutical compositions of the disclosure comprise about 0.0003 mg to about 0.015 mg of Compound 1, or a corresponding amount of a pharmaceutically acceptable salt thereof.

In some embodiments, formulations or pharmaceutical compositions of the disclosure comprise about 0.003 mg to about 0.030 mg of Compound 1, or a corresponding amount of a pharmaceutically acceptable salt thereof. In some embodiments, formulations or pharmaceutical compositions of the disclosure comprise about 0.003 mg to about 0.006 mg of Compound 1, or a corresponding amount of a pharmaceutically acceptable salt thereof. In some embodiments, formulations or pharmaceutical compositions of the disclosure comprise about 0.003 mg to about 0.009 mg of Compound 1, or a corresponding amount of a pharmaceutically acceptable salt thereof. In some embodiments, formulations or pharmaceutical compositions of the disclosure comprise about 0.003 mg to about 0.015 mg of Compound 1, or a corresponding amount of a pharmaceutically acceptable salt thereof.

In some embodiments, formulations or pharmaceutical compositions of the disclosure comprise about 0.0003 mg to about 0.003 mg of Compound 1, or a corresponding amount of a pharmaceutically acceptable salt thereof. In some embodiments, formulations or pharmaceutical compositions of the disclosure comprise about 0.0006 mg to about 0.003 mg of Compound 1, or a corresponding amount of a pharmaceutically acceptable salt thereof. In some embodiments, formulations or pharmaceutical compositions of the disclosure comprise about 0.0009 mg to about 0.003 mg of Compound 1, or a corresponding amount of a pharmaceutically acceptable salt thereof. In some embodiments, formulations or pharmaceutical compositions of the disclosure comprise about 0.0015 mg to about 0.003 mg of Compound 1, or a corresponding amount of a pharmaceutically acceptable salt thereof.

In some embodiments, formulations or pharmaceutical compositions of the disclosure comprise about 0.00006 mg to about 0.030 mg of Compound 1, or a corresponding amount of a pharmaceutically acceptable salt thereof. In some embodiments, formulations or pharmaceutical compositions of the disclosure comprise about 0.00009 mg to about 0.030 mg of Compound 1, or a corresponding amount of a pharmaceutically acceptable salt thereof. In some embodiments, formulations or pharmaceutical compositions of the disclosure comprise about 0.00015 mg to about 0.030 mg of Compound 1, or a corresponding amount of a pharmaceutically acceptable salt thereof. In some embodiments, formulations or pharmaceutical compositions of the disclosure comprise about 0.0006 mg to about 0.030 mg of Compound 1, or a corresponding amount of a pharmaceutically acceptable salt thereof. In some embodiments, formulations or pharmaceutical compositions of the disclosure comprise about 0.0009 mg to about 0.030 mg of Compound 1, or a corresponding amount of a pharmaceutically acceptable salt thereof. In some embodiments, formulations or pharmaceutical compositions of the disclosure comprise about 0.0015 mg to about 0.030 mg of Compound 1, or a corresponding amount of a pharmaceutically acceptable salt thereof. In some embodiments, formulations or pharmaceutical compositions of the disclosure comprise about 0.006 mg to about 0.030 mg of Compound 1, or a corresponding amount of a pharmaceutically acceptable salt thereof. In some embodiments, formulations or pharmaceutical compositions of the disclosure comprise about 0.009 mg to about 0.030 mg of Compound 1, or a corresponding amount of a pharmaceutically acceptable salt thereof. In some embodiments, formulations or pharmaceutical compositions of the disclosure comprise about 0.015 mg to about 0.030 mg of Compound 1, or a corresponding amount of a pharmaceutically acceptable salt thereof.

In some embodiments, formulations or pharmaceutical compositions of the disclosure comprise about 0.00003 mg of Compound 1, or a corresponding amount of a pharmaceutically acceptable salt thereof. In some embodiments, formulations or pharmaceutical compositions of the disclosure comprise about 0.030 mg of Compound 1, or a corresponding amount of a pharmaceutically acceptable salt thereof. In some embodiments, formulations or pharmaceutical compositions of the disclosure comprise about 0.0003 mg of Compound 1, or a corresponding amount of a pharmaceutically acceptable salt thereof. In some embodiments, formulations or pharmaceutical compositions of the disclosure comprise about 0.003 mg of Compound 1, or a corresponding amount of a pharmaceutically acceptable salt thereof. In some embodiments, formulations or pharmaceutical compositions of the disclosure comprise about 0.00005 mg of Compound 1, or a corresponding amount of a pharmaceutically acceptable salt thereof. In some embodiments, formulations or pharmaceutical compositions of the disclosure comprise about 0.0005 mg of Compound 1, or a corresponding amount of a pharmaceutically acceptable salt thereof. In some embodiments, formulations or pharmaceutical compositions of the disclosure comprise about 0.005 mg of Compound 1, or a corresponding amount of a pharmaceutically acceptable salt thereof. In some embodiments, formulations or pharmaceutical compositions of the disclosure comprise about 0.010 mg of Compound 1, or a corresponding amount of a pharmaceutically acceptable salt thereof. In some embodiments, formulations or pharmaceutical compositions of the disclosure comprise about 0.0001 mg of Compound 1, or a corresponding amount of a pharmaceutically acceptable salt thereof. In some embodiments, formulations or pharmaceutical compositions of the disclosure comprise about 0.001 mg of Compound 1, or a corresponding amount of a pharmaceutically acceptable salt thereof.

In some embodiments, formulations or pharmaceutical compositions of the disclosure comprise about 0.00002 mg to about 0.020 mg of a metabolite of Compound 1, such as Compound 2, or a corresponding amount of a pharmaceutically acceptable salt thereof. In some embodiments, formulations or pharmaceutical compositions of the disclosure comprise about 0.001 mg to about 5 mg of a metabolite of Compound 1, such as Compound 2, or a corresponding amount of a pharmaceutically acceptable salt thereof. In some embodiments, formulations or pharmaceutical compositions of the disclosure comprise about 0.00002 mg to about 0.002 mg of a metabolite of Compound 1, such as Compound 2, or a corresponding amount of a pharmaceutically acceptable salt thereof. In some embodiments, formulations or pharmaceutical compositions of the disclosure comprise about 0.0002 mg to about 0.002 mg of a metabolite of Compound 1, such as Compound 2, or a corresponding amount of a pharmaceutically acceptable salt thereof. In some embodiments, formulations or pharmaceutical compositions of the disclosure comprise about 0.00002 mg to about 5 mg of a metabolite of Compound 1, such as Compound 2, or a corresponding amount of a pharmaceutically acceptable salt thereof. In some embodiments, formulations or pharmaceutical compositions of the disclosure comprise about 0.0002 mg to about 0.020 mg of a metabolite of Compound 1, such as Compound 2, or a corresponding amount of a pharmaceutically acceptable salt thereof.

In some embodiments, a formulation or pharmaceutical composition of the disclosure may be administered in a single dose. In some embodiments, a formulation or pharmaceutical composition of the disclosure may be administered in a divided dose. In some embodiments, an initial dose of a formulation or pharmaceutical composition of the disclosure provides luteal phase support. In some embodiments, an initial dose of a formulation or pharmaceutical composition of the disclosure is a trigger for oocyte maturation. In some embodiments, two doses of a formulation or pharmaceutical composition of the disclosure may be administered. A second dose of a formulation or pharmaceutical composition of the disclosure may result in more viable oocytes and better pregnancy rates for some women. Further, a second dose may be needed to achieve a full LH surge and to obtain mature oocytes and could be given in both oocyte donation and banking and IVF/ICSI cycles. In some embodiments, a second dose may be needed for luteal phase support. In certain such embodiments, the second dose may be needed in an ART protocol involving fresh transfer of an embryo. In some embodiments, the second dose is administered within about 8 to about 60 hours after administration of the initial dose. In certain such embodiments, the second dose is administered within about 8 to about 12 hours after administration of the initial dose. In some embodiments, the second dose is administered within about 8 to about 16 hours after administration of the initial dose. In some embodiments, the second dose is administered within about 8 to about 24 hours after administration of the initial dose. In some embodiments, the second dose is administered within about 8 to about 32 hours after administration of the initial dose. In some embodiments, the second dose is administered within about 8 to about 40 hours after administration of the initial dose. In some embodiments, the second dose is administered within about 8 to about 48 hours after administration of the initial dose. In some embodiments, the second dose is administered within about 8 to about 54 hours after administration of the initial dose. In some embodiments, the second dose is administered within about 12 to about 16 hours after administration of the initial dose. In some embodiments, the second dose is administered within about 12 to about 24 hours after administration of the initial dose. In some embodiments, the second dose is administered within about 12 to about 32 hours after administration of the initial dose. In some embodiments, the second dose is administered within about 12 to about 40 hours after administration of the initial dose. In some embodiments, the second dose is administered within about 12 to about 48 hours after administration of the initial dose. In some embodiments, the second dose is administered within about 12 to about 54 hours after administration of the initial dose. In some embodiments, the second dose is administered within about 24 to about 36 hours after administration of the initial dose. In some embodiments, the second dose is administered within about 24 to about 48 hours after administration of the initial dose. In some embodiments, the second dose is administered within about 24 to about 60 hours after administration of the initial dose. In some embodiments, the second dose is administered within about 36 to about 48 hours after administration of the initial dose. In some embodiments, the second dose is administered within about 36 to about 60 hours after administration of the initial dose. In some embodiments, the second dose is administered within about 48 to about 60 hours after administration of the initial dose.

In some embodiments, three doses of a formulation or pharmaceutical composition of the disclosure may be administered. In some embodiments, the third dose of a formulation or pharmaceutical composition of the disclosure provides luteal phase support. In some embodiments, the third dose is administered within about 8 to about 60 hours after administration of the second dose. In certain such embodiments, the third dose is administered within about 8 to about 12 hours after administration of the second dose. In some embodiments, the third dose is administered within about 8 to about 16 hours after administration of the second dose. In some embodiments, the third dose is administered within about 8 to about 24 hours after administration of the second dose. In some embodiments, the third dose is administered within about 8 to about 32 hours after administration of the second dose. In some embodiments, the third dose is administered within about 8 to about 40 hours after administration of the second dose. In some embodiments, the third dose is administered within about 8 to about 48 hours after administration of the second dose. In some embodiments, the third dose is administered within about 8 to about 54 hours after administration of the second dose. In some embodiments, the third dose is administered within about 12 to about 16 hours after administration of the second dose. In some embodiments, the third dose is administered within about 12 to about 24 hours after administration of the second dose. In some embodiments, the third dose is administered within about 12 to about 32 hours after administration of the second dose. In some embodiments, the third dose is administered within about 12 to about 40 hours after administration of the second dose. In some embodiments, the third dose is administered within about 12 to about 48 hours after administration of the second dose. In some embodiments, the third dose is administered within about 12 to about 54 hours after administration of the second dose. In some embodiments, the third dose is administered within about 24 to about 36 hours after administration of the second dose. In some embodiments, the third dose is administered within about 24 to about 48 hours after administration of the second dose. In some embodiments, the third dose is administered within about 24 to about 60 hours after administration of the second dose. In some embodiments, the third dose is administered within about 36 to about 48 hours after administration of the second dose. In some embodiments, the third dose is administered within about 36 to about 60 hours after administration of the second dose. In some embodiments, the third dose is administered within about 48 to about 60 hours after administration of the second dose.

In some embodiments, a third dose of a formulation or pharmaceutical composition of the disclosure is administered and is followed by administration of one to five additional doses. In some embodiments, the one to five additional doses of a formulation or pharmaceutical composition of the disclosure administered after a third dose of a formulation or pharmaceutical composition of the disclosure provide luteal phase support. In some embodiments, the one to five additional doses of a formulation or pharmaceutical composition of the disclosure administered after a third dose of a formulation or pharmaceutical composition of the disclosure are administered after oocyte retrieval. In some embodiments wherein a third dose of a formulation or pharmaceutical composition of the disclosure is administered and is followed by administration of one to five additional doses, the administration of the one to five additional doses is within about 8 to about 60 hours after the prior dose is administered. In certain such embodiments, the one to five additional doses are administered within about 8 to about 12 hours after administration of the prior dose. In some embodiments, the one to five additional doses are administered within about 8 to about 16 hours after administration of the prior dose. In some embodiments, the one to five additional doses are administered within about 8 to about 24 hours after administration of the prior dose. In some embodiments, the one to five additional doses are administered within about 8 to about 32 hours after administration of the prior dose. In some embodiments, the one to five additional doses are administered within about 8 to about 40 hours after administration of the prior dose. In some embodiments, the one to five additional doses are administered within about 8 to about 48 hours after administration of the prior dose. In some embodiments, the one to five additional doses are administered within about 8 to about 54 hours after administration of the prior dose. In some embodiments, the one to five additional doses are administered within about 12 to about 16 hours after administration of the prior dose. In some embodiments, the one to five additional doses are administered within about 12 to about 24 hours after administration of the prior dose. In some embodiments, the one to five additional doses are administered within about 12 to about 32 hours after administration of the prior dose. In some embodiments, the one to five additional doses are administered within about 12 to about 40 hours after administration of the prior dose. In some embodiments, the one to five additional doses are administered within about 12 to about 48 hours after administration of the prior dose. In some embodiments, the one to five additional doses are administered within about 12 to about 54 hours after administration of the prior dose. In some embodiments, the one to five additional doses are administered within about 24 to about 36 hours after administration of the prior dose. In some embodiments, the one to five additional doses are administered within about 24 to about 48 hours after administration of the prior dose. In some embodiments, the one to five additional doses are administered within about 24 to about 60 hours after administration of the prior dose. In some embodiments, the one to five additional doses are administered within about 36 to about 48 hours after administration of the prior dose. In some embodiments, the one to five additional doses are administered within about 36 to about 60 hours after administration of the prior dose. In some embodiments, the one to five additional doses are administered within about 48 to about 60 hours after administration of the prior dose.

The following are examples of embodiments of the disclosure and are not to be construed as limiting.

EXAMPLES

Throughout the Figures and Examples, the term "API-FB" is used to refer to the free form of Compound 1. The term "API-MA" is used to refer to the monoacetate salt form of Compound 1.

Additionally, throughout the Figures and Examples, the dosage amounts used refer to the amount of API-FB present in the formulation. It would be clear to one of skill in the art how to calculate the amount of API-FB taking into account the difference in molecular weight between API-FB and API-MA. For example, 10.0 mg of API-FB, would correspond to 10.5 mg of API-MA.

Baseline levels noted in the Examples refer to an individual's hormone levels prior to being administered one or more doses of a compound of the disclosure.

The activity of API-MA was examined in vitro and in vivo in a series of pharmacological studies.

In vitro receptor binding studies demonstrated that API-MA has high affinity for the human KISS1R, with an average $IC_{50}$ value of 230 pmol/L. In a human GPR54-calcium mobilization assay, the agonist activity of API-MA had a concentration producing a half maximal effective concentration ($EC_{50}$) of 266 pmol/L. The kisspeptin (45-54) $EC_{50}$ was 314 pmol/L.

Example 1

In Vitro Pharmacology

Binding Affinity of API-MA for KISS1R: The binding affinity of API-MA to membrane fractions of KISS1R-expressing recombinant cells was examined in a competitive binding assay. Varying concentrations of API-MA and $^{125}$I-kisspeptin (45-54) were incubated with the membrane fractions of recombinant cells expressing rat, dog, monkey, and human KISS1R.

The results of receptor binding studies showed that the binding affinity of API-MA to KISS1R of the species tested varied, with an $IC_{50}$ value ranging from 230 to 870 pmol/L. In recombinant Chinese hamster ovary cells (cell line h175-KB34) expressing the human KISS1R, the $IC_{50}$ value for API-MA was approximately 2.5 times higher than that for kisspeptin (45-54), the C-terminal 10 amino acid residue peptide of kisspeptin, with an $IC_{50}$ value of 230 pmol/L for API-MA versus 93 pmol/L for kisspeptin (45-54).

Example 2

Effects of API-MA on Intracellular $Ca^{2+}$ Levels in Chinese Hamster Ovary Cells Expressing KISS1R The effects of API-MA on intracellular $Ca^{2+}$ mobilization in KISS1R-expressing recombinant cells were evaluated by performing the fluorometric imaging plate reader assay. API-MA increased intracellular $Ca^{2+}$ levels in Chinese hamster ovary dihydrofolate reductase negative cells expressing rat, dog, monkey, or human KISS1R in a concentration dependent manner. The $EC_{50}$ values of API-MA in cells expressing rat, dog, monkey, or human type receptor were 632, 2010, 74.0, and 266 pmol/L, respectively. A reference compound, kisspeptin (45-54), showed $EC_{50}$ values of 310, 1680, 78.7, and 314 pmol/L, respectively. The ratios of $EC_{50}$ values of API-MA to that of kisspeptin (45-54), were 2.0, 1.2, 0.94, and 0.85 for cells expressing each type of receptor, respectively. These results suggest that the agonistic activity of API-MA to KISS1R is as potent as that of kisspeptin (45-54).

Secondary Pharmacodynamics: In a series of 127 enzyme and radio ligand binding assays, API-MA, at 10 µmol/L, did not show any significant inhibitory effect in the indicated enzyme and receptor binding assays.

Example 3

Pharmacokinetics and Drug Metabolism in Animals

The PK of API-MA was studied in rats, dogs, and monkeys. After SC administration, API-MA was rapidly absorbed, and the bioavailability of API-MA was good across species (>55%).

In Vitro Distribution and Metabolism Studies: The in vitro distribution ratios of [$^{14}$C]API-MA into the blood cells at the concentrations of 0.01, 0.1, 1, and 10 µg/mL API-FB (free form) were 7.8%, 8.0%, 7.1%, and 4.8% for rats, 2.4%, 2.0%, 1.6%, and 1.2% for dogs, and 2.0%, 0.0%, 0.0%, and 0.5% for humans, respectively. These results indicated that the distribution ratios of API-FB into the blood cells were low and almost constant in the concentration range of 0.01 to 10 µg/mL as API-FB in rats, dogs, and humans. The in vitro plasma protein binding ratios of [$^{14}$C]API-FB in rats, dogs, monkeys, and humans were determined by the ultracentrifugation method. In addition, the protein binding to human serum albumin (HSA), $\alpha_1$-acid glycoprotein (AGP), and HSA/AGP was investigated. The results from this study indicated that the plasma protein binding of API-FB was moderate in all species examined (range from 55.3% to 73.3%). In rats and dogs, a slight decrease in the binding ratio at the concentration range between 0.1 and 1.0 µg/mL API-FB was observed. In monkeys and humans, the binding was independent of the drug concentrations from 0.01 to 10 µg/mL API-FB. The binding ratio in the HSA/AGP mixture was lower than in human plasma and, unlike human plasma, the ratio had a tendency to decline in a concentration dependent manner, suggesting that API-FB bound not only to albumin and $\alpha_1$-acid glycoprotein but also to other protein(s) in human plasma.

Inhibition of CYP by API-MA was evaluated in vitro using recombinant CYPs; the data ($IC_{50}$ values>10 µg/L) indicate that API-MA is unlikely to be an inhibitor of CYP1A2, CYP2B6, CYP2C8, CYP2C9, CYP2C19, CYP2D6, or CYP3A4.

Pharmacokinetics in Rats: The PK of API-MA was studied in rats after SC and IV administration. The PK profile of API-MA in rats is summarized in Table 1.

After SC administration of API-MA at doses of 1 and 10 mg/kg, the increase in the maximum observed plasma concentration ($C_{max}$) of API-FB in plasma was less than dose-proportional (~2.3 times increase). The mean values were 381.3 and 284.6 ng/mL, respectively. On the other hand, the increase in area under the plasma concentration-time curve from time 0 to 24 hours ($AUC_{(0-24)}$) of API-FB after SC administration of 10 mg/kg was >2.5 times less than those observed at 1 mg/kg. The mean values for 10 and 1 mg/kg doses were 309 and 804 ng.hr/mL, respectively. The reason the $C_{max}$ and AUC values in rats were not dose-proportional is unknown. However, the time to reach the maximum observed plasma concentration ($T_{max}$) was roughly constant for all tested doses; values were between 0.3 and 0.9 hours. The terminal elimination half-life ($T_{1/2}$) was not determined due to the limited number of data points.

After IV administration of API-MA at a dose of 1 mg/kg, the plasma concentration at 5 minutes ($C_{5min}$) was 2672.3 ng/mL. The concentration then decreased biphasically, with a $T_{1/2}$ of 0.5 hours for the alpha phase. The $T_{1/2}$ for the beta phase was not calculated because of the limited number of data points. The $AUC_{(0-24)}$ value was 1457 ng.hr/mL.

The bioavailability of an SC dose of 1 mg/kg of API-MA in rats was good (55.3%).

The PK linearity of API-MA was also investigated in rats after IV administration. The plasma $C_{5min}$ and $AUC_{(0-24)}$ values increased dose-proportionally. The values for plasma $C_{5min}$ were 24.1, 250.0, and 2577.8 ng/mL and those for $AUC_{(0-24)}$ were 14, 140, and 1390 ng.hr/mL at doses of 0.01, 0.1, and 1 mg/kg, respectively. The elimination $T_{1/2}$ values were 0.4 hours at 0.01 and 0.1 mg/kg and 0.5 hours at 1 mg/kg. These findings indicate that the PK of API-FB was linear in rats after single IV administration over the dose range of 0.01 to 1 mg/kg. The greater than dose-proportional increase in the first-pass kinetics with SC administration would indicate nonlinear PK in rats after SC administration.

TABLE 1

PK Parameters of API-FB in Rats

| Dose Route | Dose (a) (mg/kg) | Tmax (hr) | Cmax (ng/mL) | AUC(0-24) (ng · hr/mL) | AUC/Dose ($10^{-6}$ kg · hr/mL) | BA (b) (%) |
|---|---|---|---|---|---|---|
| SC | 0.1 | 0.5 ± 0.0 | 90.0 ± 12.5 | 123 ± 9 | 1234 ± 92 | — |
|  | 1 | 0.9 ± 0.2 | 381.3 ± 75.5 | 804 ± 133 | 804 ± 133 | 55.3 ± 8.6 |
|  | 10 | 0.3 ± 0.0 | 284.6 ± 58.6 | 309 ± 70 | 31 ± 7 | — |
| IV | 1 | — | 2672.3 ± 234.3 (c) | 1457 ± 143 | — | — |

— = not estimated: BA = bioavailability.
Mean value ± standard deviation (SD) (n = 5).
(a) Vehicle is a mixture of dimethyl acetamide and 5% glucose solution (1:9, vol/vol).
(b) BA = (AUC SC/AUC IV) × (Dose IV/Dose SC) × 100.
(c) C5 min.

The concentrations of the radioactivity in the tissues of male albino and pigmented rats were investigated after a single IV administration of [$^{14}$C]API-MA at 1.049 mg/kg (1 mg/kg API-FB). The results of this study showed that API-MA-related compounds were distributed widely into the tissues, with lower concentrations than in the plasma in most of the tissues except for the kidneys and urinary bladder. The radioactivity, measured in albino rats, was rapidly eliminated from all of the tissues after IV administration of API-MA. It was also indicated that API-MA-related compounds had little affinity for melanin in vivo.

The urinary, fecal, biliary, and expiratory excretion of the dosed radioactivity was investigated after a single SC or IV administration of [$^{14}$C]API-MA at 1.049 mg/kg (1 mg/kg API-FB) to male Sprague-Dawley rats in two studies.

In the first study, urinary, fecal, and biliary excretions were investigated. After SC or IV administration, API-MA was mainly excreted in urine (84.7% and 76.6%, respectively), followed by bile (15.5% and 20.7%, respectively) and feces (0.2% and 0.3%, respectively) at 24 hours postdose.

In the second study, urinary, fecal, and expiratory excretions were investigated. After SC or IV administration, API-MA was mainly excreted in urine (78.1% and 70.0%, respectively) and feces (20.4% and 28.2%, respectively) at 48 hours postdose. The excretion via expiration was minimal. The results from this study also indicate that the excretion was almost completed by 48 hours postdose after SC or IV administration of [$^{14}$C]API-MA to rats.

Pharmacokinetics in Dogs: The PK of API-MA was studied in dogs after SC and IV administration. The PK profile of API-MA in dogs is summarized in Table 2 below.

After SC administration of API-MA to dogs, plasma $C_{max}$ and $AUC_{(0-24)}$ values increased in a dose-proportional manner over the dose range of 0.1 to 10 mg/kg. The plasma $C_{max}$ values were 86.6, 882.7, and 8842.5 ng/mL and the plasma $AUC_{(0-24)}$ values were 252, 2596, and 28,626 ng.hr/mL at the doses of 0.1, 1, and 10 mg/kg, respectively. The plasma $T_{max}$ values were within 0.8 to 1.0 hours for the tested doses.

After a bolus IV administration of API-MA at a dose of 1 mg/kg, the plasma $C_{5min}$ value was 4254.4 ng/mL, and the concentration decreased with a triphasic time course. The elimination $T_{1/2}$ value was 3.0 hours. The $AUC_{(0-24)}$ value was 3093 ng.hr/mL.

The bioavailability of API-MA after SC administration was good, with estimated values of 81.5%, 84.0%, and 92.7% at the doses of 0.1, 1, and 10 mg/kg, respectively.

On the basis of these results, although SC-administered API-MA underwent slight first-pass kinetics before absorption, API-MA was well absorbed in dogs, and the PK of API-MA showed a dose-proportional increase in the dose range from 0.1 to 10 mg/kg.

TABLE 2

| | | | | | | | | | |
|---|---|---|---|---|---|---|---|---|---|
| PK Parameters of API-FB in Dogs | | | | | | | | | |
| Dose | Dose (a) | Tmax | Cmax | T½ (hr) | | | AUC(0-24) | AUC/Dose | BA (b) |
| Route | (mg/kg) | (hr) | (ng/mL) | α | β | γ | (ng · hr/mL) | ($10^{-6}$ kg · hr/mL) | (%) |
| SC | 0.1 | 0.8 ± 0.3 | 86.6 ± 19.0 | ND | 1.4 ± 0.2 | NC | 252 ± 34 | 2518 ± 339 | 81.5 ± 11.5 |
| | 1 | 0.8 ± 0.3 | 882.7 ± 251.3 | ND | 1.4 ± 0.3 | 2.6 ± 0.2 | 2596 ± 219 | 2596 ± 219 | 84.0 ± 8.1 |
| | 10 | 1.0 ± 0.0 | 8842.5 ± 1202.1 | ND | 1.5 ± 0.4 | 2.6 ± 0.1 | 28.626 ± 1814 | 2863 ± 181 | 92.7 ± 7.7 |
| IV | 1 | — | 4254.4 ± 543.4 (c) | 0.2 ± 0.0 | 1.1 ± 0.0 | 3.0 ± 0.1 | 3093 ± 80 | — | — |

— = not estimated; BA = bioavailability; NC = not calculated; ND = not detected.
Mean value ± SD (n = 4).
(a) Vehicle is a mixture of dimethyl acetamide and 5% glucose solution (1:9, vol/vol).
(b) BA = (AUC SC/AUC IV) × (Dose IV/Dose SC) × 100.
(c) C5 min.

Pharmacokinetics in Monkeys: The PK of API-MA was studied in monkeys after SC and IV administration. The PK profile of API-MA in monkeys is summarized in Table 3 below.

After SC administration to monkeys, $C_{max}$ and $AUC_{(0-24)}$ values increased in a dose-proportional manner over the dose range of 0.1 to 10 mg/kg. The plasma $C_{max}$ values were 122.6, 1323.4, and 12,089.6 ng/mL, and for the plasma $AUC_{(0-24)}$, values were 295, 2791, and 31,576 ng.hr/mL at the doses of 0.1, 1, and 10 mg/kg, respectively. The $T_{max}$ values were within 0.3 to 0.4 hours for the tested doses. After reaching $C_{max}$, the concentrations decreased. A multi-exponential decline was noted after IV administration with mean terminal elimination $T_{1/2}$ of approximately 2.6 hours, which was similar to that obtained after IV administration. The steep distribution phase was not evident after SC dosing because the slow absorption of API-MA from the SC injection site partially masked the distribution phase.

After bolus IV administration of API-MA at a dose of 1 mg/kg, the plasma $C_{5min}$ value was 5027.0 ng/mL, and the concentration decreased with a triphasic time course. The elimination $T_{1/2}$ value was 3.2 hours. The $AUC_{(0-24)}$ value was 3160 ng.hr/mL.

The SC bioavailability of API-MA was good, with values of 94.9%, 90.1%, and 101.9% at doses of 0.1, 1.0, and 10 mg/kg, respectively.

These results indicate that API-MA was well absorbed in monkeys and that, when administered SC, API-MA underwent minimal or no first-pass effect before absorption. The PK of API-MA showed a dose-proportional increase in monkeys in the dose range from 0.1 to 10 mg/kg.

TABLE 3

PK Parameters of API-FB in Dogs

| Dose Route | Dose (a) (mg/kg) | Tmax (hr) | Cmax (ng/mL) | T$_{1/2}$ (hr) α | T$_{1/2}$ (hr) β | T$_{1/2}$ (hr) γ | AUC(0-24) (ng · hr/mL) | ADC/Dose ($10^{-6}$ kg · hr/mL) | BA (b) (%) |
|---|---|---|---|---|---|---|---|---|---|
| SC | 0.1 | 0.4 ± 0.1 | 122.6 ± 27.3 | ND | 1.6 ± 0.3 | NC | 295 ± 27 | 2950 ± 266 | 94.9 ± 12.4 |
|  | 1 | 0.3 ± 0.0 | 1323.4 ± 316.1 | ND | 1.4 ± 0.2 | 2.5 ± 0.2 | 2791 ± 262 | 2791 ± 262 | 90.1 ± 15.4 |
|  | 10 | 0.4 ± 0.1 | 12.089.0 ± 2370.2 | ND | 1.5 ± 0.3 | 2.6 ± 0.3 | 31.576 ± 1396 | 3157 ± 140 | 101.9 ± 14.3 |
| IV | 1 | — | 5027.0 ± 786.7 (e) | 0.3 ± 11.0 | 1.2 ± 0.1 | 3.2 ± 0.1 | 3160 ± 594 | NE | NE |

BA = bioavailability; NC = not calculated; ND = not detected; NE = not estimated.
Mean value ± SD (n = 4).
(a) Vehicle is a mixture of dimethyl acetamide and 5% glucose solution (1:9, vol/vol).
(b) BA = (AUC SC/AUC IV) × (Dose IV/Dose SC) × 100.
(e) C5 min.

Pharmacokinetics and Product Metabolism: The following PK parameters are summarized for plasma and urine API-MA, as appropriate, following administration of API-MA:

$C_{max}$, maximum observed plasma concentration.

$T_{max}$, time to reach $C_{max}$.

$C_{ss}$, steady-state plasma concentration.

$AUC_{(0-24)}$, area under the plasma concentration-time curve (AUC) from time 0 to 24 hours.

$AUC_{(0-inf)}$, AUC from time 0 to infinity.

$T_{1/2}$, terminal elimination half-life.

CL/F, apparent clearance (after subcutaneous [SC] dosing).

Fe, fraction of dose excreted in urine.

Example 4

Summary of Studies

Single Dose PK—Summary: In Japanese men, systemic exposure to API-MA, measured as $C_{max}$ and $AUC_{(0-inf)}$, increased dose-proportionally over the single dose range studied, 0.001 to 0.5 mg. Mean CL/F ranged from 13.7 to 19.8 L/hr. Median $T_{max}$ for SC bolus administration of API-MA ranged from 0.375 to 0.750 hour, suggesting rapid systemic uptake of API-MA from the SC dosing site. In general, mean $T_{1/2}$ values increased with increasing dose. This can be attributed to API-MA concentrations below the limit of quantitation of assay resulting in underestimation of $T_{1/2}$ and apparent dose dependency of this parameter after administration of low doses of API-MA. At the highest doses studied, 0.25 and 0.5 mg, mean $T_{1/2}$ was 3.77 to 4.27 hours. Mean Fe ranged from 4.24% to 7.10% of the administered dose for doses from 0.004 to 0.5 mg.

Based on PK data from a phase 1 study of API-MA conducted in European men, $AUC_{(0-inf)}$ increased dose-proportionally after the administration of single SC doses of 0.001 to 0.3 mg and 2-hour SC infusion of 1, 3, and 6 mg. The CL/F values ranged from 18.9 to 27.1 L/hr following single SC bolus and 2-hour infusion doses of API-MA. Median $T_{max}$ for SC bolus administration of API-MA ranged from 0.5 to 0.750 hour, indicating rapid systemic uptake of API-MA from the SC dosing site, which was not dose dependent over the SC dose range evaluated in this study. At the highest doses studied, 3 and 6 mg, mean $T_{1/2}$ was approximately 5.2 hours and generally increased with increasing dose. Fe ranged from 3.09% to 5.40% of the administered dose for doses from 0.003 to 6 mg.

Multiple-Dose PK—Summary: In a phase 1 study of prolonged (continuous over 13 days) SC INF of API-MA, the $C_{ss}$ of API-MA increased in an apparent dose-proportional fashion and the mean CL/F values ranged from 17.7 to 20.6 L/hr over the dose range evaluated (0.01 to 1 mg). In a study of hormone-naïve Japanese prostate cancer patients, API-MA was administered at doses of 0.5 or 1.0 mg/day as a 2-hour SC infusion for 14 days. Plasma concentrations of API-MA increased and reached $C_{max}$ immediately after the end of infusion, and then declined with a mean $T_{1/2}$ value of about 3 to 4 hours on both days 1 and 14 at both doses. There was an approximate dose-proportional increase in exposure of API-MA 0.5 and 1.0 mg/day doses via SC infusion. No accumulation of API-MA was observed after multiple SC administration for 14 days.

1-Month Depot Summary: In another study, prostate cancer patients who were either on GnRH agonist therapy or were potential future candidates for GnRH agonist therapy received either 6, 12, or 24 mg as a single 1-month depot injection (N=3 per dose group). A high-burst release of API-MA drug concentrations was observed within hours after administration of depot injection. The $AUC_{(0-24)}$ comprised over 60% of the area under the plasma concentration-time curve from time 0 to the time of last quantifiable concentration ($AUC_{(0-tlqc)}$) observed, showing a significant release of drug from formulation during the burst phase. Very low levels of drug concentrations were present over the next several days followed by a slow rise, consistent with presumed delayed and slow release from the formulation. In all cases, API-MA was not detectable by 8 weeks postdose.

Single Dose Pharmacokinetics of API-MA: This study was conducted in Japan as a randomized, double-blind, placebo-controlled, parallel-group, ascending dose study to evaluate API-MA safety, plasma and urine PK, and endocrine PD effects following administration of single SC bolus doses (0.001-0.5 mg) or a 2-hour SC infusion (0.25 and 0.5 mg) that was expected to stimulate testosterone levels. Thirty-seven healthy Japanese male subjects aged 50 to 74 years were enrolled into nine cohorts. Subjects enrolled in the first seven cohorts received 0.001, 0.004, 0.01, 0.04, 0.1, 0.25 or 0.5 mg of API-MA or placebo by single SC bolus. In the 0.001 mg cohort, 3 subjects received API-MA and two received placebo. In the remaining cohorts, 3 subjects received API-MA and one received placebo. Subjects enrolled in the eighth and ninth cohorts received 0.25 or 0.5 mg of API-MA or placebo by single 2-hour SC infusion. In both cohorts, 3 subjects received API-MA and one received placebo. The plasma PK analysis set consisted of 31 subjects (bolus cohorts: 25; infusion cohorts: 6), and the urine PK analysis set consisted of 35 subjects (bolus cohorts: 27; infusion cohorts: 8).

To measure plasma concentrations of API-MA in subjects in the SC bolus cohorts, blood specimens were collected at the following nominal times: predose, 0.083, 0.25, 0.5, 0.75, 1, 2, 3, 4, 6, 8, 12, 16, 24, 36, 48 and 72 hours postdose. To measure urinary excretion of API-MA, urine specimens were collected at the following nominal times: predose, 0 to 4, 4 to 8, 8 to 12, 12 to 24, 24 to 36, 36 to 48 and 48 to 72 hours postdose.

To measure plasma concentrations of API-MA in subjects in the SC infusion cohorts, blood specimens were collected at the following nominal times: predose and 0.25, 0.5, 1, 2, 2.25, 2.5, 2.75, 3, 4, 5, 6, 8, 10, 14, 24, 36, 48 and 72 hours after the start of the infusion. To measure urinary excretion of API-MA, urine specimens were collected at the following nominal times: predose and 0 to 4, 4 to 8, 8 to 12, 12 to 24, 24 to 36, 36 to 48 and 48 to 72 hours after the start of the infusion.

The mean plasma and urine PK parameter values for single dose API-MA administered by SC bolus and for single dose API-MA administered by 2-hour SC infusion are listed in Table 4 below.

mg. Dose-proportionality was assessed formally by fitting a power model to the data. The point estimate for the power exponent was 1.023 for $C_{max}$ (95% confidence interval [CI], 0.970-1.076) and 1.027 for $AUC_{(0-inf)}$ (95% CI, 0.979-1.075). Mean $C_{max}$ and $AUC_{(0-inf)}$ values following 2-hour SC infusion of 0.5 mg of API-MA were similar to the mean values following an SC bolus (8230 versus 9050 pg/mL and 34650 versus 29970 hr·pg/mL, respectively). Note that there was only one subject in the 0.25 mg infusion cohort. The mean CL/F ranged from 13.7 to 19.8 L/hr following administration of single bolus and 2-hour SC infusion doses of API-MA.

Median $T_{max}$ for SC bolus administration of API-MA ranged from 0.375 to 0.750 hour, suggesting rapid systemic uptake of API-MA from the SC dosing site. The rapid uptake of API-MA did not appear to be dose dependent.

In general, mean $T_{1/2}$ values increased with increasing dose. This can be attributed to API-MA concentrations below the limit of quantitation of assay resulting in underestimation of $T_{1/2}$ and apparent dose dependency of this

TABLE 4

Mean Single Dose SC Bolus and Single Dose 2-Hour SC Infusion PK Parameters

| Parameter | Dose (mg) Single-Dose SC Bolus | | | | | |
|---|---|---|---|---|---|---|
| | 0.001 | 0.004 | 0.01 | 0.04 | 0.1 | 0.25 |
| Plasma | | | | | | |
| N | 2 | 3 | 3 | 3 | 2 | 2 |
| Cmax (pg/mL) | 20.1 (3.3) | 61.7 (9.1) | 221 (28) | 966 (230) | 2415 (318) | 5895 (247) |
| Tmax (a) (hr) | 0.5 (0.5-0.5) | 0.5 (0.5-0.75) | 0.5 (0.5-0.75) | 0.5 (0.25-0.5) | 0.375 (0.25-0.5) | 0.75 (0.75-0.75) |
| AUC(0-inf) (hr · pg/mL) | 54.1 (3.7) | 205 (33) | 671 (49) | 2606 (868) | 5785 (1463) | 18320 (1713) |
| T½ (hr) | 1.59 (0.08) | 1.91 (0.25) | 1.82 (0.13) | 3.35 (1.00) | 3.58 (0.88) | 4.09 (0.33) |
| CL/F (L/hr) | 18.6 (1.3) | 19.8 (3.3) | 15.0 (1.1) | 16.7 (6.1) | 17.9 (4.5) | 13.7 (1.3) |
| Urine | | | | | | |
| N | 2 | 3 | 3 | 3 | 3 | 3 |
| Fe (%) | 0 (0) | 6.16 (1.48) | 5.40 (1.16) | 4.24 (1.51) | 5.20 (1.19) | 7.10 (0.46) |

| | Dose (mg) | | |
|---|---|---|---|
| | Single-Dose SC Bolus | Single-Dose 2-Hour SCINF | |
| Parameter | 0.5 | 0.25 | 0.5 |
| Plasma | | | |
| N | 3 | 1 | 3 |
| Cmax (pg/mL) | 9050 (1429) | 4020 (NC) | 8230 (1500) |
| Tmax (a) (hr) | 0.5 (0.5-0.75) | 2.25 (2.25 ± 2.25) | 2.5 (2.5-2.75) |
| AUC(0-inf) (hr · pg/mL) | 29970 (3950) | 13280 (NC) | 34650 (418.1) |
| T½ (hr) | 4.27 (0.56) | 3.77 (NC) | 4.02 (0.45) |
| CL/F (L/hr) | 16.9 (2.4) | 18.8 (NC) | 14.6 (1.8) |
| Urine | | | |
| N | 3 | 3 | 3 |
| Fe (%) | 6.33 (0.54) | 6.21 (1.94) | 5.22 (2.04) |

NC = not calculated.
(a) Median (range).

Following a single SC bolus of API-MA, systemic exposure to API-MA, measured as $C_{max}$ and $AUC_{(0-inf)}$, increased dose-proportionally over the dose range studied, 0.001 to 0.5 parameter after administration of low doses of API-MA. At the highest doses studied (0.25 and 0.5 mg), mean $T_{1/2}$ was 3.77 to 4.27 hours.

No API-MA was detected in the urine following a single SC bolus of 0.001 mg API-MA. Across the higher dose bolus and infusion cohorts (0.004 to 0.5 mg), mean single dose Fe ranged from 4.24% to 7.10% of the administered dose of API-MA. Plots of the cumulative urinary excretion of API-MA showed that excretion was essentially complete by 24 hours.

Example 5

Pharmacodynamic Effects of API-MA Administered as a SC Bolus

Another study was a phase 1 randomized, double-blind, placebo-controlled, parallel-group, ascending dose study of the safety, tolerability, plasma and urine PK, and endocrine pharmacodynamic effects of API-MA administered as a SC bolus (0.001-0.3 mg) or a 2-hour SC infusion (1-6 mg) that was expected to stimulate testosterone. The study was conducted in France.

Eighty-two healthy European male subjects aged 50 to 76 years were enrolled into nine cohorts. 81/82 subjects (98.8%) were white and 1/82 subject (1.2%) was black/African American. Subjects enrolled in the first six cohorts received 0.001, 0.003, 0.01, 0.03, 0.1, or 0.3 mg of API-MA or placebo by single SC bolus. In the 0.3 mg cohort, 6 subjects received API-MA and two received placebo. In the remaining cohorts, 7 subjects received API-MA and three received placebo. Subjects enrolled in the seventh, eighth, and ninth cohorts received 1, 3, or 6 mg of API-MA or placebo by single 2-hour SC infusion. In these cohorts, 6 subjects received API-MA and two received placebo.

To measure plasma concentrations of API-MA in subjects in the SC bolus cohorts, blood specimens were collected at the following nominal times: predose and 0.083, 0.25, 0.5, 0.75, 1, 2, 3, 4, 6, 8, 12, 16, 24, 36, 48 and 72 hours postdose. To measure urinary excretion of API-MA, urine specimens were collected at the following nominal times: from 12 hours prior to dosing until dosing and 0 to 6, 6 to 12, 12 to 24, 24 to 48 and 48 to 72 hours postdose.

To measure plasma concentrations of API-MA in subjects in the SC infusion cohorts, blood specimens were collected at the following nominal times: predose and 0.5, 1, 1.5, 2, 2.25, 2.5, 3, 4, 6, 8, 10, 14, 18, 26, 50 and 74 hours after the start of the infusion. To measure urinary excretion of API-MA, urine specimens were collected at the following nominal times: from 12 hours prior to dosing until dosing and 0 to 6, 6 to 12, 12 to 24, 24 to 48, and 48 to 72 hours after the start of the infusion.

Figure 2:
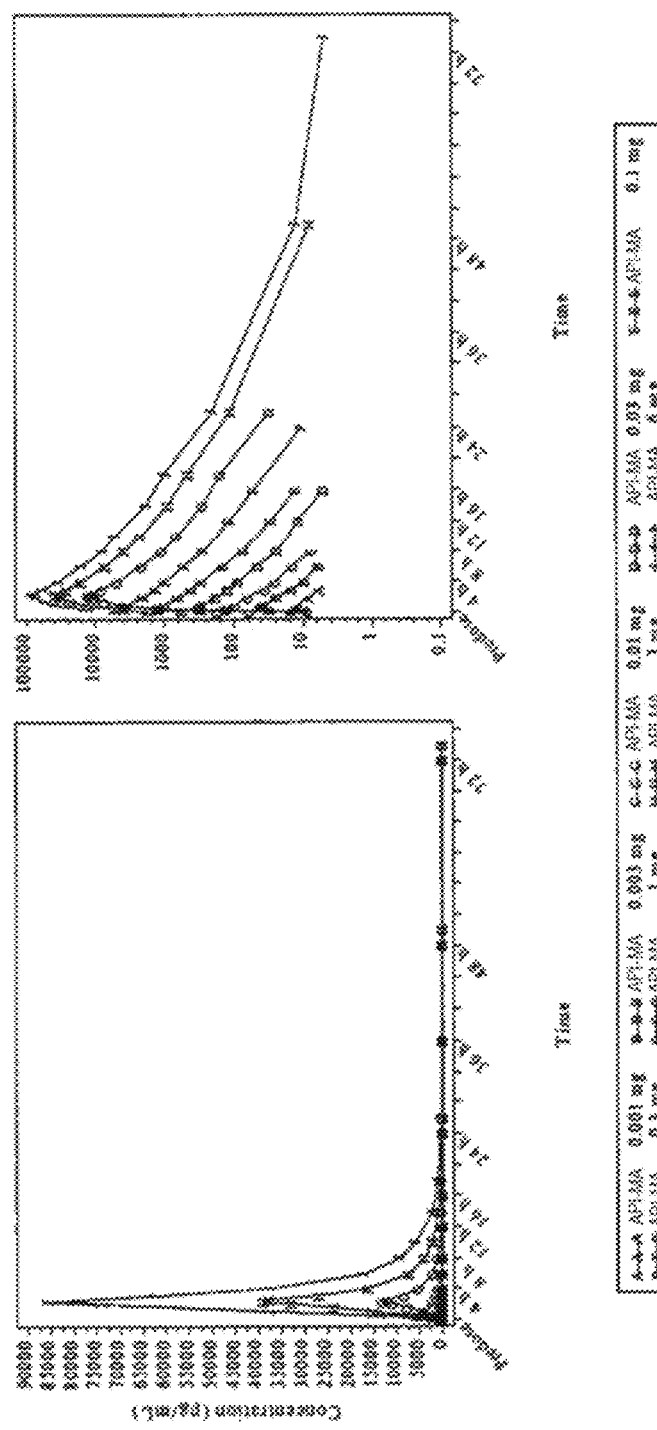
FIG. 2 provides plots depicting mean plasma concentrations of Compound 1 monoacetate (API-MA) up to 72 hours by treatment group when administered to healthy European men as described in Example 5.

Mean plasma API-MA concentration-time curves following a single SC administration of API-MA at doses ranging from 0.001 to 6 mg are shown in FIG. 2. The mean percent coefficient of variation (% CV) plasma and urine PK parameter values for single dose API-MA administered by SC bolus and for single dose API-MA administered by 2-hour SC infusion are listed in the following Tables 5 to 8.

TABLE 5

Mean (% CV) Plasma PK Parameters Following a Single SC Adminstration of API-MA at Doses Ranging From 0.001 to 0.3 mg

| | Geometric Mean (% CV) (a) | | | |
|---|---|---|---|---|
| Parameter | 0.001 mg (N = 7) | 0.003 mg (N = 7) | 0.01 mg (N = 7) | 0.03 mg (N = 7) |
| Cmax (pg/mL) | 13.253 (19.10) | 42.384 (30.36) | 140.140 (44.26) | 340.182 (17.60) |
| AUC(0-inf) (hr · pg/mL) | 47.459 (33.78) | 122.246 (16.03) | 370.975 (26.81) | 1108.096 (20.49) |
| AUC(0-tlqc) (hr · pg/mL) | 26.693 (21.64) | 100.915 (20.18) | 345.193 (28.87) | 1069.885 (20.65) |
| T½ (hr) (b) | 1.796 (1.20-4.58) | 1.425 (1.18-2.34) | 2.172 (1.82-2.72) | 2.610 (1.50-3.11) |
| Tmax (hr) (b) | 0.500 (0.25-1.00) | 0.750 (0.50-1.00) | 0.500 (0.25-0.75) | 0.500 (0.25-0.75) |
| CL/F (L/hr) | 21.071 (33.78) | 24.541 (16.03) | 26.956 (26.81) | 27.073 (20.49) |
| Vz/F (L) | 63.925 (27.13) | 55.862 (34.30) | 85.629 (34.48) | 95.981 (14.77) |

| | Geometric Mean (% CV) (a) | |
|---|---|---|
| Parameter | 0.1 mg (N = 7) | 0.3 mg (N = 6) |
| Cmax (pg/mL) | 1382.196 (26.77) | 4349.244 (34.08) |
| AUC(0-inf) (hr · pg/mL) | 3943.856 (14.92) | 13213.549 (25.03) |
| AUC(0-tlqc) (hr · pg/mL) | 3887.968 (14.81) | 13155.656 (25.06) |
| T½ (hr) (b) | 3.079 (2.29-3.56) | 3.451 (2.98-4.10) |
| Tmax (hr) (b) | 0.500 (0.25-0.75) | 0.625 (0.25-0.75) |
| CL/F (L/hr) | 25.356 (14.92) | 22.704 (25.03) |
| Vz/F (L) | 108.017 (21.08) | 114.225 (32.60) |

Vz/F = apparent volume of distribution.
(a) CV (%) = 100 × $\sqrt{(\exp(SDlog2) - 1)}$ where SDlog is the standard deviation of log-transformed values.
(b) Median (minimum-maximum) values.

TABLE 6

Mean (% CV) Plasma PK Parameters Following a 2-Hour
INF of API-MA at Doses Ranging From 1 to 6 mg

| Parameter | Geometric Mean (% CV) (a) | | |
|---|---|---|---|
| | 1 mg (N = 6) | 3 mg (N = 6) | 6 mg (N = 6) |
| Cmax (pg/mL) | 1.3050.559 (20.79) | 39402.798 (14.80) | 82477.820 (22.6.3) |
| AUC(0-inf) (hr · pg/mL) | 43825.188 (25.51) | 141488.720 (11.42) | 317753.435 (25.60) |
| AUC(0-tlqc) (hr · pg/mL) | 43656.011 (25.51) | 141392.642 (11.41) | 317666.507 (25.60) |
| T½ (hr) (b) | 3.643 (3.46-3.83) | 5.249 (3.19-5.86) | 5.264 (4.56-5.62) |
| Tmax (hr) (b) | 2.250 (2.00-2.25) | 2.250 (2.25-2.50) | 2.250 (2.00-2.50) |
| CL/F (L/hr) | 22.818 (25.51) | 21.203 (11.42) | 18.883 (25.60) |
| Vz/F (L) | 119.955 (27.97) | 149.910 (28.78) | 140.984 (28.67) |

Vz/F = apparent volume of distribution.
(a) CV (%) = 100 × √(exp(SDlog2) − 1) where SDlog is the standard deviation of log-transformed values.
(b) Median (minimum-maximum) values.

TABLE 7

Mean (% CV) Urine PK Parameters Following a Single SC Adminstration of API-MA at Doses Ranging From 0.001 to 0.3 mg

| Parameter | Geometric Mean (% CV) | | | | | |
|---|---|---|---|---|---|---|
| | 0.001 mg (N = 7) (a) | 0.003 mg (N = 7) | 0.01 mg (N = 7) | 0.03 mg (N = 7) | 0.1 mg (N = 7) | 0.3 mg (N = 6) |
| CLr (L/hr) | 1048.546 | 1180.964 (15.74) | 1073.430 (21.35) | 937.560 (30.52) | 1048.697 (24.89) | 860.937 (41.44) |
| Ae(0-t) (ng) | 34.658 | 119.177 (17.70) | 370.540 (20.69) | 1003.082 (31.55) | 4077.298 (28.29) | 11326.187 (30.17) |
| Fe (%) | 3.466 | 3.973 (17.70) | 3.705 (20.69) | 3.344 (31.56) | 4.077 (28.29) | 3.775 (30.17) |

(a) Only 1 subject with a concentration above lower limit of quantification (LLOQ), 6 subjects were set to 0.
Ae(0-t) = amount of drug excreted in urine from time 0 time t.
CLr = reval clearance.

TABLE 8

Mean (% CV) Urine PK Parameters Following a 2-Hour
INF of API-MA at Doses Ranging From 1 to 6 mg

| Parameter | Geometric Mean (% CV) | | |
|---|---|---|---|
| | 1 mg (N = 6) | 3 mg (N = 6) | 6 mg (N = 6) |
| CLr (L/hr) | 686.544 (29.02) | 835.762 (45.31) | 1016.230 (27.70) |
| Ae(0-t) (ng) | 29971.789 (27.97) | 118170.544 (41.46) | 322822.342 (10.34) |
| Fe (%) | 2.997 (27.97) | 3.939 (41.46) | 5.380 (10.34) |

Ae(0-t) = amount of drug excreted in urine from time 0 time t, CLr = renal clearance.

The peak concentration of API-MA ($C_{max}$) increased dose-proportionally following administration of single SC bolus doses ranging from 0.001 to 0.3 mg. The systemic exposure of API-MA measured as $AUC_{(0-inf)}$ increased dose-proportionally after the administration of single SC doses of 0.001 to 0.3 and 2-hour SC infusion of 1, 3, and 6 mg. The estimated exponents of the power equation were 1.003 for $C_{max}$ (95% CI, 0.956-1.050) and 1.019 for $AUC_{(0-inf)}$ (95% CI, 0.997-1.040). The CL/F values ranged from 18.9 to 27.1 L/hr following single SC bolus and 2-hour infusion doses of API-MA.

Median $T_{max}$ for SC bolus administration of API-MA ranged from 0.5 to 0.750 hour, indicating rapid systemic uptake of API-MA from the SC dosing site. The rapid SC uptake of API-MA was not dose dependent over SC dose range evaluated in this study.

In general, mean $T_{1/2}$ values increased with increasing dose. Examination of FIG. 2 suggests that the likely reason for the longer $T_{1/2}$ can potentially be attributed to the assay sensitivity and the inclusion of measurable API-MA concentrations at the terminal portion of the curve in the estimation of $T_{1/2}$ at higher doses. Hence the observed dose dependency of this parameter does not represent nonlinear pharmacokinetics for API-MA. At the highest doses studied, 3 and 6 mg, mean $T_{1/2}$ was approximately 5.2 hours.

Only a small amount of API-MA was detected in the urine following a single SC bolus of 0.001 mg API-MA. The mean (CV %) Fe for this cohort was 3.466%. Across the other dose bolus and infusion cohorts (0.003 to 6 mg), mean single dose Fe ranged from 2.997% to 5.380% of the administered dose of API-MA.

Example 6

Multiple-Dose Pharmacokinetics of API-MA

Another study was a phase 1 clinical study of multiple-dose administration of API-MA. The study was conducted in France. It was a randomized, double-blind, placebo-controlled, parallel-group, ascending dose study of the safety, tolerability, plasma PK, and endocrine pharmacodynamic effects of API-MA administered as an SC bolus (0.1 mg) on day 1 followed by continuous SC infusion (i.e., 24 hr/day) from Day 2 to Day 14 (0.01, 0.1, 0.3, or 1.0 mg/day), which was expected to suppress testosterone. Thirty healthy European male subjects aged 50 to 78 years were enrolled into four cohorts; 29/30 subjects (96.7%) were white and one subject (3.3%) was black.

To measure plasma concentrations of API-MA following SC bolus administration, blood specimens were collected at the following nominal times: predose and 0.083, 0.25, 0.5, 0.75, 1, 2, 4, 6, 12, 16, and 24 hours postdose. During SC infusion, blood specimens were collected at the following nominal times: 6, 12, 24, 54, 60, 72, 150, 156, 168, 222, 228, 240, 294, 300, and 312 hours following the start of the infusion.

The mean plasma PK parameter values for single dose API-MA administered by SC bolus are listed in Table 9 by dosing group for comparison with values after continuous 13-day SC INF on Days 2-14, as shown in Table 7. Because the single dose PK of API-MA could be assessed for only 24 hours before infusion of API-MA was begun, the only PK parameters that could be estimated were $C_{max}$, $T_{max}$, and $AUC_{(0-24)}$. The interindividual variability for the PK parameters was generally low, with % CV≤58%.

TABLE 9

Mean (% CV) PK Parameters by Dosing Group Following Single Dose SC Bolus (0.1 mg) on Day 1

| | Geometric Mean (% CV) | | | |
| --- | --- | --- | --- | --- |
| Parameter | 0.01 mg/day | 0.1 mg/day | 0.3 mg/day | 1.0 mg/day |
| N | 6 | 6 | 6 | 5 |
| Cmax (pg/mL) | 1870 (27) | 1590 (31) | 1650 (26) | 1290 (58) |
| Tmax (hr) (a) | 0.500 (0.500, 0.750) | 0.500 (0.250, 1.000) | 0.500 (0.250, 1.033) | 0.500 (0.250, 0.750) |
| AUC(0-tlqc) (hr · pg/mL) | 5080 (22) | 4280 (12) | 4680 (27) | 4050 (29) |

Note:

All groups received SC bolus (0.1 mg) on Day 1; dosing group indicates which randomized dose subjects received by SC INF from Day 2 to Day 14 (0.01-1.0 mg/day).

(a) Median (range).

(b) AUC(0-tlqc), in this case, is equal to AUC(0-24).

TABLE 10

(% CV) PK Parameters During Continuous 13-Day SC INF of API-MA (Days 2-14)

| | Geometric Mean (% CV) | | | |
| --- | --- | --- | --- | --- |
| Parameter | 0.01 mg/day | 0.1 mg/day | 0.3 mg/day | 1.0 mg/day |
| N | 6 | 6 | 6 | 5 |
| Css (pg/mL) | 20.2 (34) | 226 (17) | 708 (19) | 2280 (16) |
| CL/F (L/hr) | 20.6 (40) | 18.5 (18) | 17.7 (18) | 18.3 (16) |

Css = estimated as AUC(Day 2-Day 14)/actual time elapsed from collection of Day 2, 6-hours specimen until collection of Day 14, 24-hours specimen.

Another study was a phase 1 clinical study of multiple-dose administration of API-MA. It was an open-label, ascending dose study of API-MA administered via 2-hour SC infusion once daily for 14 days that was expected to suppress testosterone in Japanese hormone-naïve prostate cancer patients. Six patients received API-MA at doses of 0.5 mg (3 patients) and 1.0 mg (3 patients) a day for 14 days.

To measure plasma concentrations of API-MA, blood specimens were collected at the following times: Day 1 (predose and 2, 4, 6, 10 hours postdose); days 2, 4, 6, 8, 10, and 12 (predose); day 14 (predose and 2, 4, 6, 10, 24, 48 hours postdose); day 21; and day 28. To measure urinary excretion of API-MA, urine specimens were collected at the following times: Day 1 (predose and 0 to 4, 4 to 8, 8 to 12, 12 to 24 hours postdose) and day 14 (0 to 4, 4 to 8, 8 to 12, 12 to 24 hours postdose).

The mean plasma PK parameter values for API-MA administered by continuous 13-day SC infusion on Days 2-14 are listed in Table 7. The $C_{ss}$ increased in an apparent dose-proportional fashion over the dose range studied, 0.01 to 1.0 mg. Across the cohorts, CL/F ranged from 17.7 to 20.6 L/hr. The interindividual variability for the PK parameters was low, with CV %≤40%.

Figure 3:
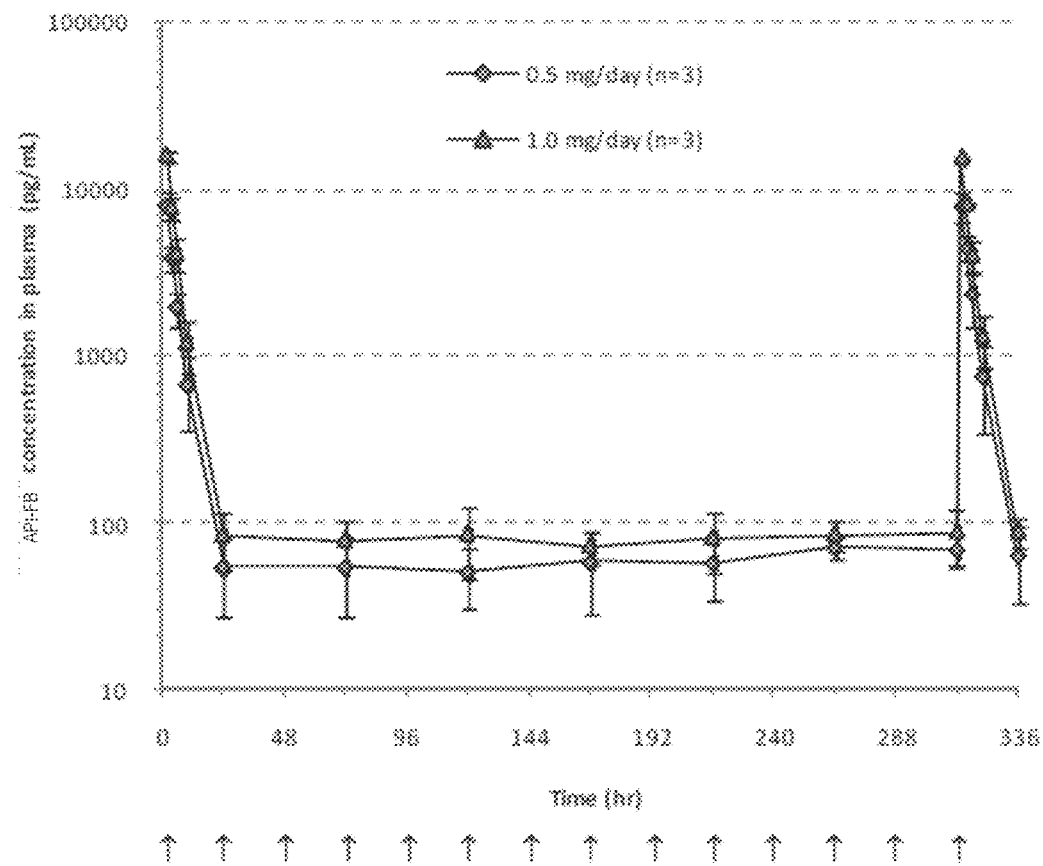
FIG. 3 is a plot depicting mean (±standard deviation [SD]) Compound 1 monoacetate (API-MA) concentration in plasma-time profiles after 2-hour subcutaneous (SC) administration of 0.5 and 1.0 mg/day API-MA for 14 days in healthy European men as described in Example 6.

Mean [±SD] API-FB concentrations in plasma-time profiles for multiple SC administration of API-MA at 0.5 and 1.0 mg/day for 14 days are depicted in FIG. 3. A summary of PK parameters on day 1 and day 14 at the two doses is shown in Table 11 below. $C_{max}$ and AUCs were similar on day 1 and 14, demonstrating no peptide accumulation. $C_{max}$ and AUC were dose-proportional.

TABLE 11

Summary of Mean (SD) PK Parameters on Days 1 and 14

|  | 0.5 | | 1.0 | |
| --- | --- | --- | --- | --- |
|  | Day 1 | Day 14 | Day 1 | Day 14 |
| N | 3 | 3 | 3 | 3 |
| Tmax (hr) | 2.11 (0.0344) | 2.08 (0.0165) | 2.11 (0.0510) | 2.11 (0.0587) |
| Cmax (pg/mL) | 8120 (1420) | 8130 (1710) | 16000 (1210) | 15500 (503) |
| $\lambda z$ (1/hr) | 0.200 (0.0160) | 0.198 (0.00349) | 0.221 (0.0187) | 0.205 (0.0103) |
| $T_{1/2}$ (hr) | 3.48 (0.290) | 3.50 (0.0614) | 3.15 (0.260) | 3.38 (0.164) |
| AUC(0-tau) (hr · pg/mL) | 36500 (7740) | 39100 (8050) | 70200 (5840) | 71200 (5650) |
| CL/F (L/hr) | 13.4 (3.27) | 12.6 (2.86) | 13.6 (1.10) | 13.4 (1.10) |
| Vz/F (L) | 66.9 (13.3) | 63.5 (13.2) | 61.6 (6.32) | 65.7 (7.83) |
| AUC(0-inf) (hr · pg/mL) | 36800 (7860) | NA | 70600 (5990) | NA |
| MRT(hr) | 4.78 (0.522) | NA | 4.64 (0.405) | NA |
| AI(AUC) | NA | 1.07 (0.0659) | NA | 1.01 (0.112) |
| AI($T_{1/2}$) | NA | 1.01 (0.0678) | NA | 1.07 (0.0429) |
| R(AUC) | NA | 1.07 (0.0676) | NA | 1.02 (0.111) |
| R(Cmax) | NA | 1.00 (0.0916) | NA | 0.967 (0.0502) |

All parameter and summary statistics are presented to three significant figures.

$\lambda z$ = apparent elimination rate constant, AI = accumulation index, AUC(0-tau) = area under the plasma concentration-time curve from 0 to tau (24 hours), MRT = mean residence time from time 0 to infinity, NA = not applicable, R = cumulative ratio, Vz/F = apparent volume of distribution.

Note:
R(AUC) is calculated as AUC(0-tau) (Day 14)/AUC(0-tau) (Day 1).

Note:
AI(AUC) is calculated as AUC(0-tau) (Day 14)/AUC(0-inf) (Day 1).

After SC administration of API-MA at 0.5 mg/day, as well as 1.0 mg/day, for 14 days, $C_{max}$ was observed immediately after the end of 2-hour infusion on Days 1 and 14 and then declined, with a mean $T_{1/2}$ value of about 3 to 4 hours on both days 1 and 14 at both doses. At 0.5 mg/day, the mean CL/F values were 13.4 and 12.6 L/hr on days 1 and 14, respectively, and at 1.0 mg/day were 13.6 and 13.4 L/hr on days 1 and 14, respectively, indicating apparent clearance of API-FB was almost the same for both doses. The Vz/F of API-FB was also similar at both dose levels. The estimated accumulation index (AI) calculated using the ratio of $AUC_{(0-tau)}$ after multiple dosing/$AUC_{(0-inf)}$ after the single dose, and R calculated as the ratio of $AUC_{(0-tau)}$ after multiple dosing/$AUC_{(0-tau)}$ after the single dose, were both approximately 1, indicating time independent PK of API-FB with minimal or no drug accumulation after 2-hr SC infusion of 0.5 and 1 mg doses daily for 14 days.

After SC administration of API-MA at 0.5 or 1.0 mg/day for 14 days, the urinary excretion of API-FB was almost complete by 8 hours postdose on days 1 and 14. The mean percent cumulative excretion at 24 hours postdose was 6.50% on day 1 and 8.99% on day 14 for the 0.5 mg/day dose, 8.86% on day 1 and 9.41% on day 14 for the 1.0 mg/day dose, respectively. These findings suggest that renal excretion does not considerably contribute to clearance of API-FB.

Example 7

1-Month Depot Pharmacokinetics of API-MA

Another study enrolled prostate cancer patients who had completed their primary treatment for prostate cancer at least 6 months prior to screening and were either on GnRH therapy or were potential future candidates for GnRH therapy. Nine patients were enrolled, three in each dose group (6, 12, and 24 mg). All were white men. Patients received API-MA as a single 1-month depot SC injection into the abdomen that was intended to initiate both a high-burst release of API-MA and rapid stimulation of hypothalamic-pituitary-gonadal-axis, and was expected to suppress testosterone. Overall, 4 of 9 patients received concomitant GnRH therapy. To measure plasma concentrations of API-MA, blood specimens were collected predose and at the following nominal times post 1-month depot injection: Month 1 (0.25, 0.5, 0.75, 1, 2, 4, 6 and 12 hours, and days 2, 3, 5, 8, 15, 22 and 29), month 2 (days 8, 15, 22 and 29), and month 3.

Figure 4:
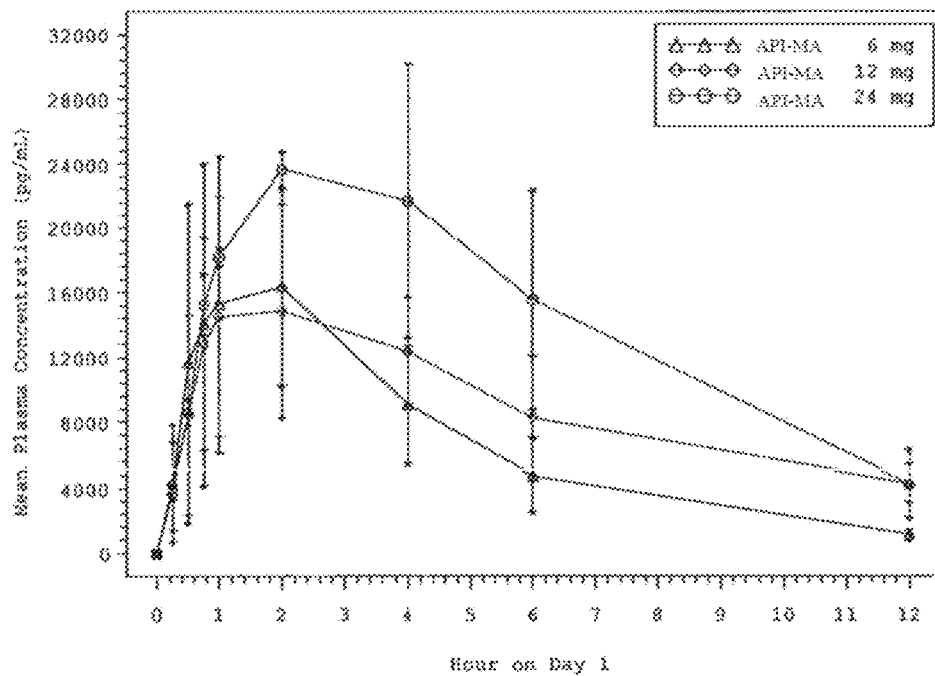
FIG. 4 is a plot depicting mean plasma concentration-time curves by dose group: Day 1 up to 12 hours in European men with prostate cancer as described in Example 7 using a SC depot injection.
Figure 5:
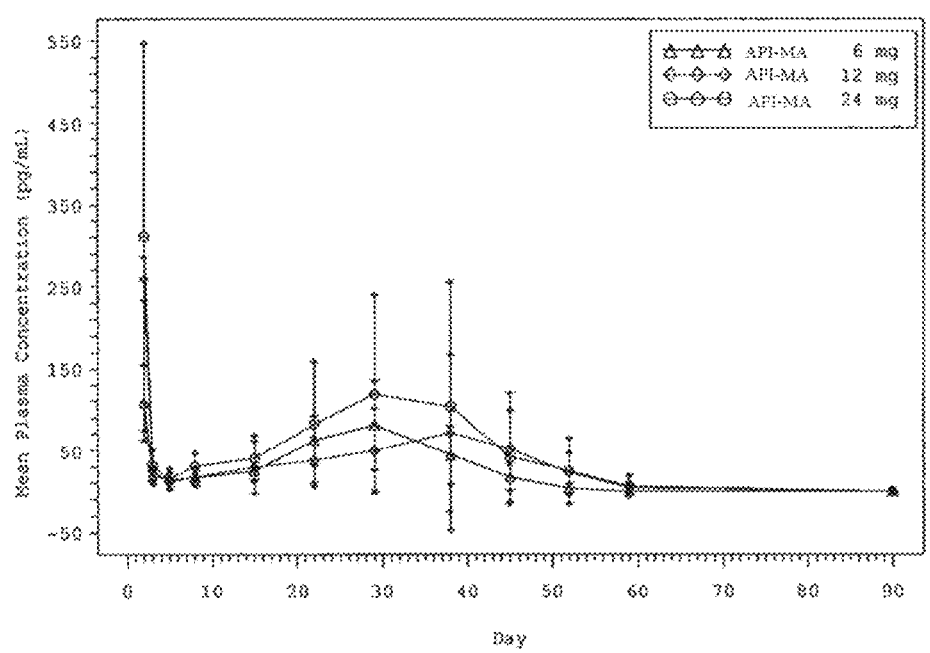
FIG. 5 is a plot depicting mean plasma concentration-time curves by dose group: Month 1, Day 2 through month 3 in European men with prostate cancer as described in Example 7 using a SC depot injection.

FIGS. 4 and 5 show mean plasma concentration-time curves by dose group for the day 1 (up to 12 hours) and the full profile (up to month 3). A high-burst release of API-MA drug concentrations was observed within hours after administration of the depot injection. The $AUC_{(0-24)}$ comprised over 60% of the $AUC_{(0-tlqc)}$ observed, showing a significant release of drug from formulation during the burst phase. Drug concentrations were very low over the next several days followed by a slow rise, suggesting delayed and slow release from the formulation, as well as onset of desensitization following continuous API-MA input. In all cases, API-MA was not detectable by 8 weeks postdose.

Table 12 presents descriptive statistics by dose group, including the PK parameters of $C_{max}$, $T_{max}$, $AUC_{(0-24)}$, area under the plasma concentration-time curve from Day 0 to Day 29 of Month 1 ($AUC_{(0-29d)}$), $AUC_{(0-tlqc)}$, and time to last quantifiable concentration (Tlqc). The mean values representing the drug exposure generally increased slightly less than proportional to dose.

TABLE 12

Summary of PK Parameters Post Depot Injection

| Parameter | Geometric Mean (% CV) | | |
|---|---|---|---|
| | 6 mg/month (N = 3) | 12 mg/month (N = 3) | 24 mg/month (N = 3) |
| Cmax (pg/mL) | 16541.7 (45.3) | 14408.6 (41.7) | 25518.0 (17.5) |
| Tmax (hr) (a) | 2.000 (1.03, 2.12) | 2.050 (1.02, 4.07) | 2.050 (2.00, 4.00) |
| AUC(0-24) (day · pg/mL) | 3316.6 (28.7) | 4979.1 (23.4) | 7466.3 (31.9) |
| AUC(0-29 d) (day · pg/mL) | 4328.8 (33.1) | 5753.2 (30.9) | 8701.2 (42.1) |
| AUC(0-tlqc) (day · pg/mL) | 4947.6 (39.0) | 6582.9 (43.7) | 9948.6 (54.4) |
| Tlqc (hr) | 42.9 (16.2) | 41.5 (44.6) | 47.2 (21.1) |

(a) Median (range)

Overall, the low plasma concentrations of API-MA, the delayed release profile over the 1 month following administration, and the high inter-patient variability of the 1-month depot formulation were considered not acceptable for further clinical development in prostate cancer patients. Furthermore, these results are not applicable to the dosing strategy that will be utilized for patients with hypothalamic hypogonadism, since it is desired to stimulate the hypothalamic-pituitary-gonadal-axis without causing suppression of testosterone.

Pharmacodynamics Single Dose Pharmacodynamics Summary: Following single dose administration of API-MA to 37 Japanese men, there was an increase in serum LH and FSH concentrations. LH and FSH concentrations peaked between 12 and 24 hours and returned to baseline by 72 hours. The magnitudes of the hormone concentration increases were similar across the dose range, 0.001 to 0.5 mg. In a single dose phase 1 study of API-MA conducted in 82 European men, administration of API-MA resulted in increased serum LH and FSH concentrations, which peaked between 6 and 12 hours and returned to baseline by 72 hours. The magnitudes and durations of the hormone concentration increases were similar across the dose range, 0.001 to 6 mg.

Multiple-Dose Pharmacodynamics Summary: In the two multi-dose studies, all doses used resulted in eventual suppression of LH levels, as expected. In study C18001, 30 healthy European men received single SC injection of 0.1 mg followed by a prolonged (continuous over 13 days) SC infusion of API-MA at doses of 0.01, 0.1, 0.3, and 1.0 mg/day. Concentrations of gonadotropins peaked at 24 hours after the 0.1 mg bolus on day 1, consistent with the other single dose, phase 1 studies. During the prolonged infusion of API-MA, serum LH and FSH concentrations declined to values below baseline and returned to baseline values within 7 days postdose. For most subjects, serum LH concentrations declined to low values. All of the subjects in the 0.1 and 0.3 mg/day cohorts had LH concentrations below the lower limit of normal for a substantial portion of time during the SC infusion. API-MA decreased serum LH and FSH levels after transient elevation, and this inhibition was maintained during the administration. Serum PSA levels decreased after API-MA administration, more profoundly in patients receiving API-MA 1.0 mg/day.

Figure 6:
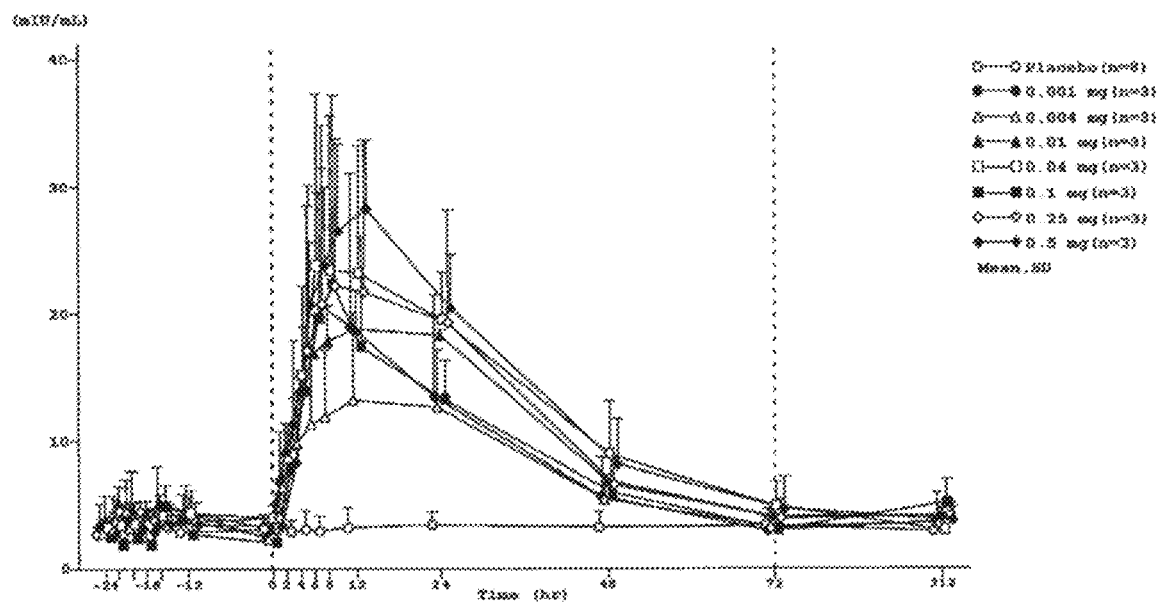
FIG. 6 is a plot depicting mean (SD) serum LH concentrations following a single SC bolus of API-MA in European men with prostate cancer as described in Example 7.

Single Dose Pharmacodynamic Effects of API-MA: In the phase 1 clinical study of API-MA, subjects enrolled in the first seven cohorts received single SC bolus doses of 0.001, 0.004, 0.01, 0.04, 0.1, 0.25 or 0.5 mg of API-MA or placebo. Subjects enrolled in the eighth and ninth cohorts received single SC infusion doses of 0.25 or 0.5 mg of API-MA or placebo. The pharmacodynamics of the following hormones were assessed: LH, FSH, dihydroepiandrosterone sulfate (DHEA-S), growth hormone (GH), prolactin (PRL), thyroid-stimulating hormone (TSH), and adrenocorticotropic hormone (ACTH). The pharmacodynamic analysis set consisted of 37 subjects (bolus cohorts: 29; infusion cohorts: 8). To measure serum concentrations of the hormones in subjects in both the bolus and infusion cohorts, blood specimens were collected at the following nominal times: predose and 2, 4, 6, 8, 12, 24, 48, 72 and 312 hours postdose. In addition, blood specimens were collected for the measurement of LH and FSH on the day prior to dosing with API-MA. The time courses of mean serum LH concentrations following a single SC bolus of API-MA at doses ranging from 0.001 mg to 0.5 mg are shown in FIG. 6. The LH concentrations peaked between 12 and 24 hours and generally returned to baseline by 72 hours postdose. The magnitudes and durations of the LH concentration increases were similar across the dose range, 0.001 to 0.5 mg. The LH time courses were similar following a single 2-hour SC infusion of API-MA (data not shown).

Figure 7:
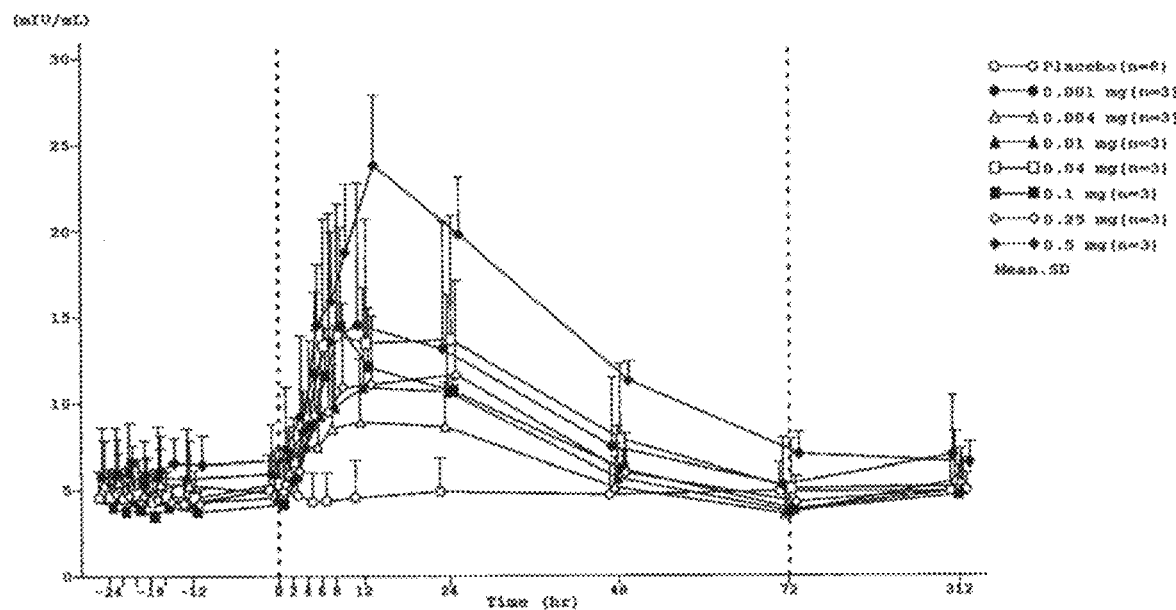
FIG. 7 is a plot depicting mean (SD) serum FSH concentrations following a single SC bolus of API-MA as described in Example 7.

As shown in FIG. 7, the serum FSH concentrations increased after a single SC bolus dose of API-MA compared with placebo. The elevation of FSH peaked within 24 hours and generally returned to the predose level by 72 hours after the injection. The magnitudes and durations of the LH and FSH concentration increases were similar across the dose range, 0.001 to 0.5 mg. The LH and FSH time courses were similar following a single 2-hour SC infusion of API-MA (data not shown).

Figure 8:
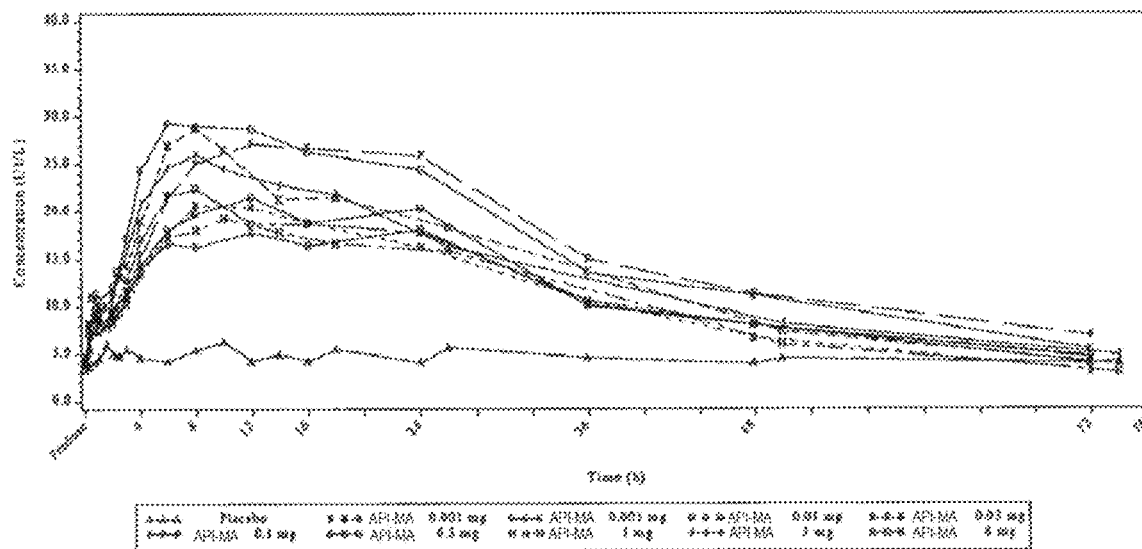
FIG. 8 is a plot depicting mean serum concentration-time profiles of LH as described in Example 7.

Another study was a single dose, phase 1 clinical study of API-MA in healthy men age 50 to 76 years. Subjects enrolled in the first seven cohorts received 0.001, 0.003, 0.01, 0.03, 0.1 or 0.3 mg of API-MA or placebo by single SC bolus. Subjects enrolled in the seventh, eighth, and ninth cohorts received 1, 3, or 6 mg of API-MA or placebo by single 2-hour SC infusion. The pharmacodynamics of each of the following hormones was assessed: LH and FSH. PRL, TSH, cortisol, sex hormone binding globulin (SHBG), and plasma ACTH (also known as corticotropin) concentrations were measured on the day prior to dosing and on day 4, the Final Visit. To measure serum concentrations of LH and FSH in the bolus cohorts, blood specimens were collected at the following nominal times: the day prior to dosing, predose, and 0.083, 0.25, 0.75, 1, 2, 3, 4, 6, 8, 12, 16, 24, 36, 48 and 72 hours postdose. In the infusion cohorts, blood specimens were collected at the following nominal times: the day prior to dosing, predose or start of the infusion, and 0.5, 1, 1.5, 2 (end of infusion), 2.25, 2.5, 3, 4, 6, 8, 10, 14, 18, 26, 50 and 74 hours after the start of infusion. Serum LH concentrations over time are shown in FIG. 8. Serum LH concentrations increased after a single SC bolus of API-MA, as well as after a single 2-hour SC infusion of API-MA. The concentrations peaked between 6 and 12 hours and returned to baseline by 72 hours. The magnitudes and durations of the LH concentration increases were similar across the dose range, 0.001 to 6 mg.

Figure 9:
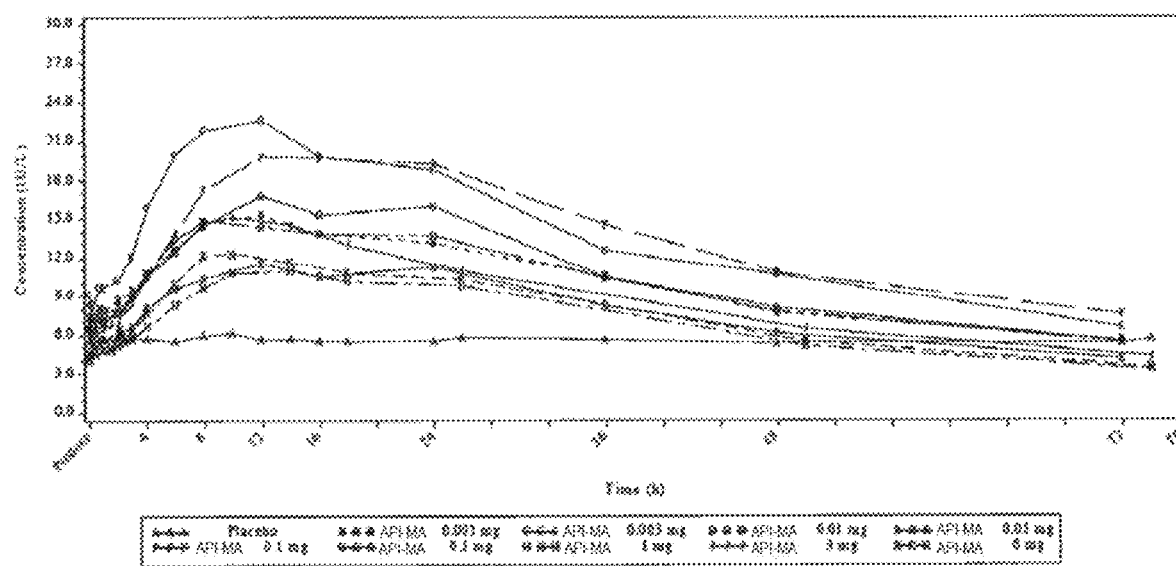
FIG. 9 is a plot depicting mean serum concentration-time profiles of FSH as described in Example 7.

API-MA administration generally resulted in an initial, moderate increase in mean FSH concentrations at all dose levels, followed by a decline towards baseline levels by 72 hours as shown in FIG. 9. These increases were not dose dependent. Peak values were generally reached at approximately 12 hours with all dose levels. There were no relevant changes in the serum concentrations of SHBG, prolactin, TSH, corticotropin, or cortisol following administration of API-MA at any dose level.

Example 8

Multiple-Dose Pharmacodynamic Effects of API-MA

This study was a phase 1 study of multiple-day, continuous SC infusions of API-MA to 30 healthy European men over age 50. Subjects enrolled into the four cohorts received a single SC bolus of API-MA 0.1 mg or placebo (day 1) followed by 0.01, 0.1, 0.3, or 1.0 mg/day of API-MA or placebo by continuous SC infusion over 13 days (days 2 to 14). Five to six men received active API-MA, and 1 to 2 men received placebo per dose level cohort. The pharmacodynamics of the following hormones were assessed: LH and FSH.

To measure serum concentrations of LH and FSH, blood specimens were collected on the day prior to dosing with API-MA at the following nominal times: −24, −16, and −12 hours (prior) to SC bolus dosing, immediately prior to the SC bolus dose, and 6, 12, 24, 30, 36, 48, 78, 84, 96, 174, 180, 192, 246, 252, 264, 318, 324 and 336 hours post-bolus dose. The SC infusion was started 24 hours after the bolus injection; all specimens collected after the 24-hour time point were collected during the SC infusion. Blood specimens were also collected on days 16, 17, 21, 28 and 44 to monitor the return of the hormone concentrations to baseline values.

Figure 10:
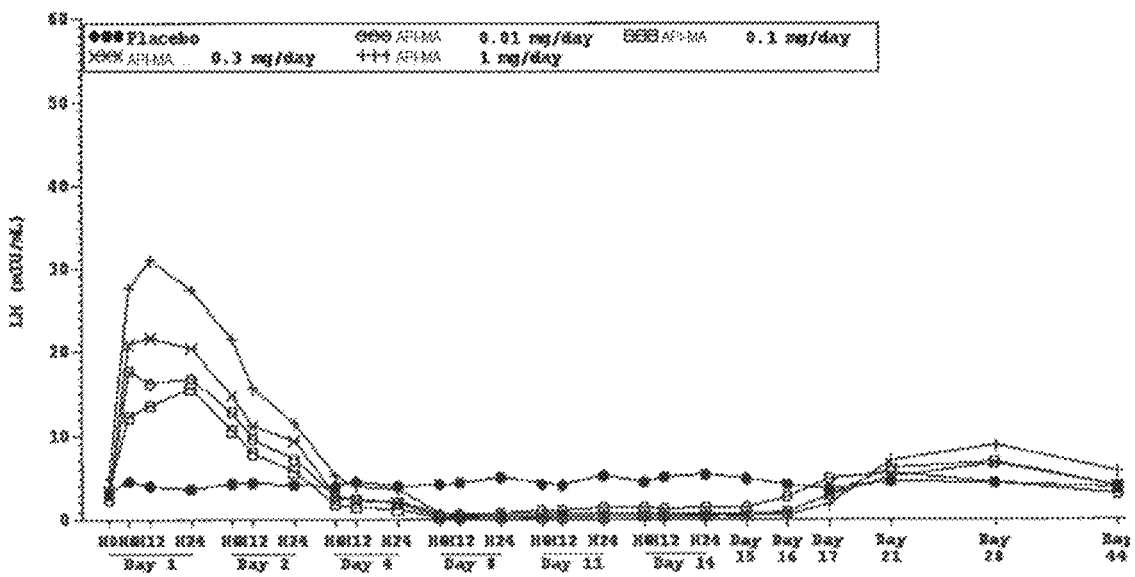
FIG. 10 is a plot depicting mean serum concentration of LH following API-MA administered by SC bolus (day 1) and continuous SC infusion (Days 2-14) as described in Example 8.
Figure 11:
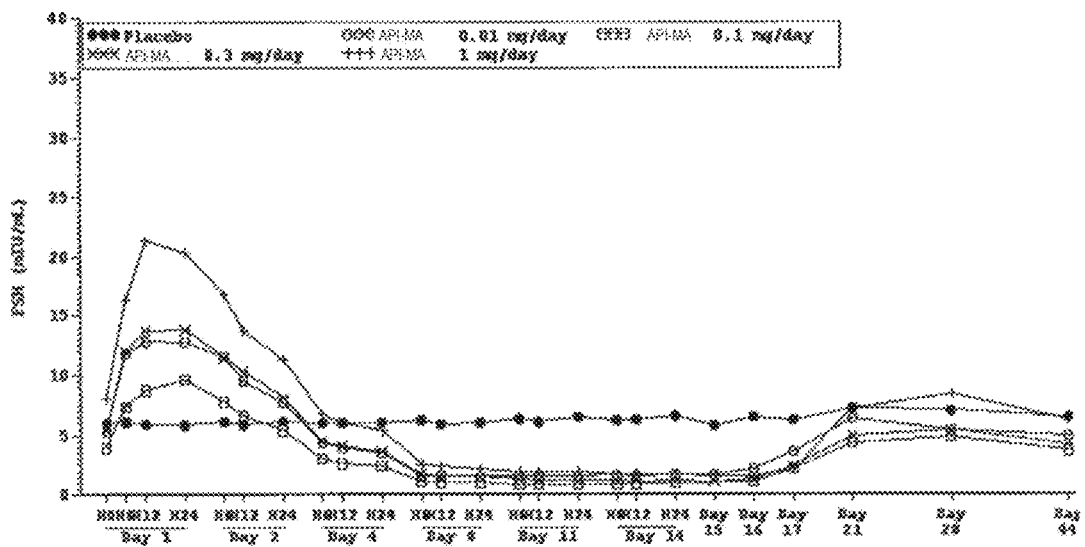
FIG. 11 is a plot depicting mean serum concentration of FSH following API-MA administered by SC bolus (Day 1) and continuous SC INF (Days 2-14) as described in Example 8.

As shown in FIGS. 10 and 11, in all active treatment groups, mean serum concentrations of LH and FSH increased following the 0.1 mg SC bolus of API-MA on day 1. During the 13-day SC infusion of API-MA, mean serum LH and FSH concentrations declined to values below baseline and returned to near baseline values within 7 days postdose. For most subjects, serum LH concentrations declined to low values. All of the subjects in the 0.1 and 0.3 mg/day cohorts had LH concentrations below the lower limit of normal for most of the SC infusion treatment period. Conversely, in subjects in the placebo treatment group, mean serum concentrations of LH and FSH remained within normal range throughout the study.

Figure 12:
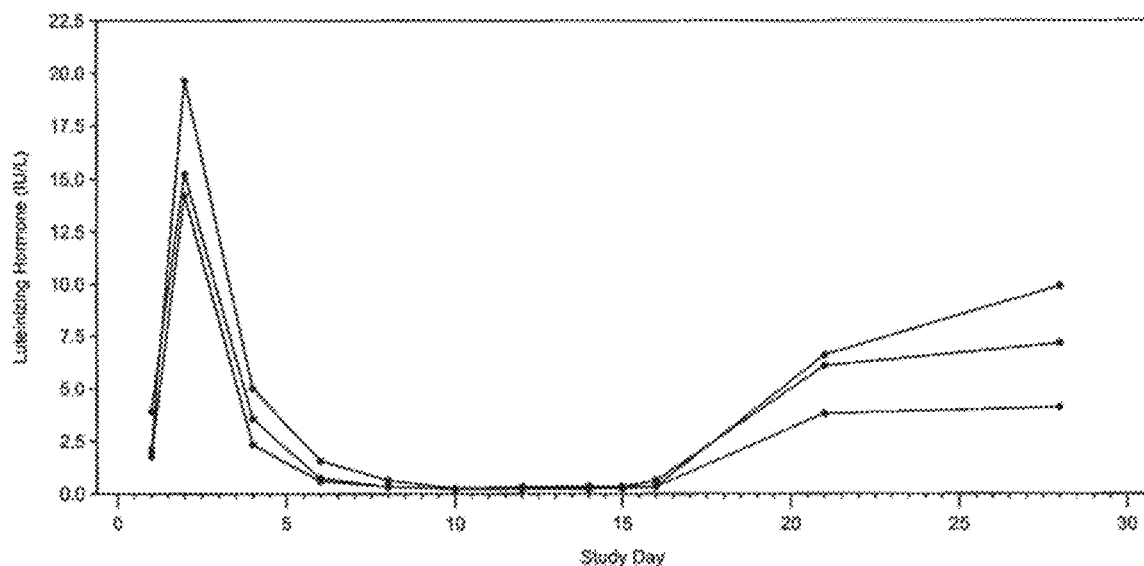
FIG. 12 is a plot depicting LH by subject (N=3) in the API-MA 0.5 mg/day group as described in Example 8.

The study was a phase 1 study in hormone naïve Japanese prostate cancer patients. Six patients received API-MA doses of 0.5 mg (3 patients) and 1.0 mg (3 patients) administered via 2-hour SC infusion once daily for 14 days. Summary statistics of serum concentrations of LH, FSH, GH, PRL, and TSH, as well as plasma concentration of ACTH and serum concentration of prostate-specific antigen (PSA), at baseline and at each evaluation point, changes from baseline were calculated for each dose, and the data (individual values and mean±standard deviation) were plotted against time for each dose. Serum LH profiles are displayed in FIG. 12 for the API-MA 0.5 mg/day dose group. Serum LH levels sharply increased at day 2, and returned to the baseline level by day 4. These levels were completely suppressed from Day 6 to Day 16, and returned to the baseline level by a week after the last dose. Changes in serum LH were similar between 0.5 and 1.0 mg of API-MA (data for API-MA 1.0 mg/day dose group not shown).

Figure 13:
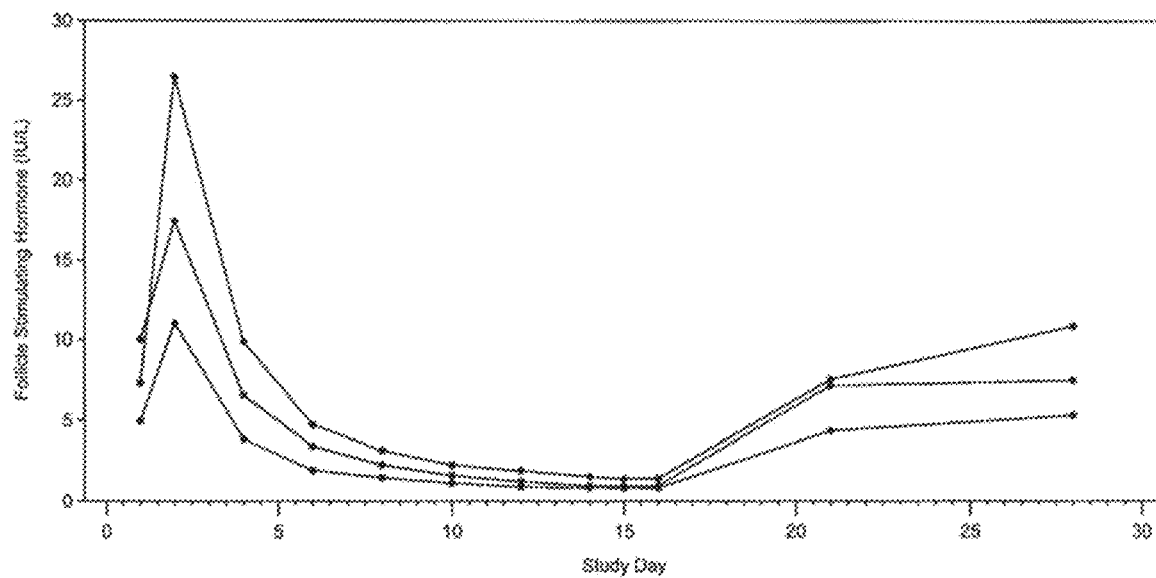
FIG. 13 is a plot depicting FSH by subject (N=3) in the API-MA 0.5 mg/day group as described in Example 8.

Serum FSH profiles are displayed in FIG. 13 for the API-MA 0.5 mg/day dose group. Serum FSH levels also sharply increased at day 2, and returned to the baseline level by day 4. These levels were completely suppressed from Day 6 to Day 16, and returned to the baseline level by a week after the last dose. Changes in serum FSH were similar between 0.5 and 1.0 mg of API-MA (data for API-MA 1.0 mg/day dose group not shown).

Serum PSA levels decreased after administration of API-MA and the low PSA levels were maintained until a week after the last dose in all subjects. Serum PSA levels decreased approximately 40% compared to the baseline level in patients receiving 0.5 mg of API-MA, and a more profound approximately 50% to 60% decline occurred in patients receiving 1.0 mg of API-MA.

Example 9

1-Month Depot Effects of API-MA

Nine patients with prostate cancer were enrolled in another study, three in each dose group (6, 12, and 24 mg). Patients received API-MA as a single 1-month depot injection that was intended to initiate both a high-burst release of API-MA and rapid stimulation of hypothalamic-pituitary-gonadal axis. Overall, 4 of 9 patients received concomitant GnRH therapy. Assessments of pharmacodynamics included LH concentrations and serum PSA concentrations. Results were grouped based on patients who were or were not receiving concomitant GnRH therapy.

LH reductions corresponding to changes in testosterone were observed in GnRH-naïve patients. Post screening serum LH concentrations ranged from 0.1 to 0.5 mIU/mL in the 6 mg dose group, from <0.1 to 7.9 mIU/mL in the 12 mg dose group, and from 0.3 to 9.8 mIU/mL in the 24 mg dose group, with individual variation between patients throughout the follow-up period. Two out of nine patients receiving concomitant GnRH analog therapy (one in the 6 mg and one in the 12 mg dose group) had PSA concentrations <0.01 ng/mL with no detectable percent changes from baseline for all but one measurement throughout the study. In the remaining seven patients, the greatest percent decrease from baseline in PSA was seen at month 1, day 29 (8% and 19% for patients in the 6 mg dose group, 25% and 62% for patients in the 12 mg dose group, and 74%, 79%, and 88% for patients in the 24 mg dose group). A further decrease in percent change from baseline was seen for three patients (one in the 6 mg, one in the 12 mg, and one in the 24 mg dose group) at month 2 day 29, with the greatest reduction in PSA of 91% observed in a patient in the 24 mg dose group.

Example 10

Use of Compound 1 and Relugolix in ART

In an effort to improve both the safety and efficacy outcomes in ART, such as IVF, and/or in an ET process, key modifications to some of the key steps of that process are herein noted and involve the use of Compound 1 and relugolix.

Traditional IVF protocols begin with an initial phase known as COS. In this phase, on day 2 or 3 of a patient's menses, FSH is administered to promote the growth and development of follicles, and is continued until ovulation occurs (~Day 14). Approximately 3-5 days after FSH is initiated, either a GnRH agonist or more commonly now, a GnRH antagonist is added to the regimen to prevent premature ovulation (the release of premature follicles due to a LH surge), and like FSH is continued until ovulation occurs. A common GnRH antagonist used in these protocols today is injectable cetrorelix, but in this particular prophetic example, an oral GnRH antagonist, relugolix, is used, as it reduces the number of multiple injections in ART, such as IVF and/or in an ET process, and may allow a more tailored titration of GnRH antagonist activity compared to an injectable. Improving the residual GnRH antagonist activity may improve the LH response to the trigger (Compound 1 described below), which ultimately improves the implantation rate. Relugolix can suppress and prevent premature ovulation, allowing eggs to mature and later be retrieved from the ovaries (instead of the fallopian tubes). Relugolix may also prevent high-order multiple gestation that can result from exposure of eggs to sperm in the fallopian tube if intercourse has occurred. Together, this stimulation process with FSH and a GnRH antagonist, Relugolix is called COS.

Once the follicles have progressed to a pre-defined state, in which the lead follicle is measured as >14 mm, a so-called "trigger" agent is used to promote the final maturation, release and retrieval of eggs from the ovary in preparation for IVF and ET to the uterus. Compound 1 (2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, and a pharmaceutically acceptable excipient) is used as the trigger agent. Compound 1 is used as a trigger to promote oocyte maturation and induce ovulation for subsequent retrieval, fertilization (in vitro) and ET. Other agents (e.g., estradiol and progestins) are also used to support the uterus (endometrium), so-called luteal phase support in preparation for implantation.

One of the main risk associated with ART, including IVF and/or in an ET process, is the development of OHSS. While some patients are at higher risk of development OHSS, the use of hCG-based trigger agents (i.e., hCG alone or hCG with a GnRH agonist) is known to increase the risk of OHSS. Compound 1, is expected to significantly decrease the risk of OHSS.

When Compound 1 is used as a trigger agent, it is expected to provide similar or improved pregnancy rates compared to hCG-based or GnRH agonist trigger agents. Compound 1 facilitates the maturation, release (ovulation) and retrieval of fresh mature oocytes (eggs) from the ovaries, leading to higher pregnancy rates, while significantly mitigating the risk of key side effects, like OHSS.

The use of hCG-based trigger agents is known to increase the need for segmentation freeze protocols that delay embryo transfer. Due to the MOA of Compound 1, there is less negative impact on the endometrium compared to current treatments. Thus, the endometrium is ready for implantation (higher endometrial receptivity) immediately after egg retrieval, thus reducing the need for segmentation (freezing the egg or embryo between retrieval and implantation). After retrieval, the egg is fertilized with sperm, and the fresh embryo is implanted into the endometrium and pregnancy ensues. Compound 1 results in less need for a segmentation freezing protocol, thereby reducing the number of IVF cycles and shortening the time to pregnancy, while maintaining acceptable pregnancy rates, with significantly lower OHSS rates.

Example 11: Investigation of the Physiological Effects of Compound 1 in Women

Part 1: Identify the Dosing Range of Compound 1

Kisspeptin-54 has previously been shown to be clinically effective as a trigger for oocyte maturation in IVF studies. This study analyzed doses of Compound 1, administered during the early follicular phase of the menstrual cycle to enable identification of doses that can stimulate a LH-response, and compare similarities and differences to the LH-response of kisspeptin-54.

The study population included healthy women, aged 18-35 years, with BMI 18-30 $kg/m^2$, no medical problems and not taking any medications or hormonal contraception. Three healthy, female subjects were selected and randomized and received a single dose of each of the three study regimens noted below (one regimen per study period). All women were scheduled for three Study D1 Visits (each during the follicular phase of the menstrual cycle). Each subject received a single dose of one of the following three study regimens on the Study D1 Visit during each study period (three study periods in total), such that at the end of this part of the study, each subject received all three of the following study regimens (one per study period):

Kisspeptin-54 (KP54), 9.6 nmol/kg
Compound 1, 0.003 nmol/kg* or 0.00368 mcg/kg
Compound 1, 0.03 nmol/kg* or 0.0368 mcg/kg

*For example, a 60 kg woman who is administered the 0.003 nmol/kg dose of Compound 1, would receive 0.18 nmols or 0.221 mcg. The order in which a subject receives one of the three study regimens was determined by a randomization matrix.

Compound 1 vials were stored at 4° C. and consisted of 200 mcg (0.2 mg) in 2000 mcl (2 mL), i.e., 0.1 mcg/mcl (0.1 mg/mL). Freeze-dried kisspeptin-54 (600 nmol per vial) was reconstituted in 0.5-1 mL of normal saline in preparation for subcutaneous injection (Table 13).

| Component | Function | Quantity per Vial (2 mL) |
|---|---|---|
| Compound 1 drug substance | API | 0.21 mg |
| Compound 1 Freebase | | (0.2 mg) |
| D-Mannitol, JP/USP/Ph. Eur. | Tonicity agent | 100 mg |
| Glacial acetic acid, JP/USP/Ph. Eur. | pH adjusting agent | Appropriate amount |
| Water for injection, JP/USP/Ph. Eur. | Solvent | q.s. to 2 mL |

Figure 14:
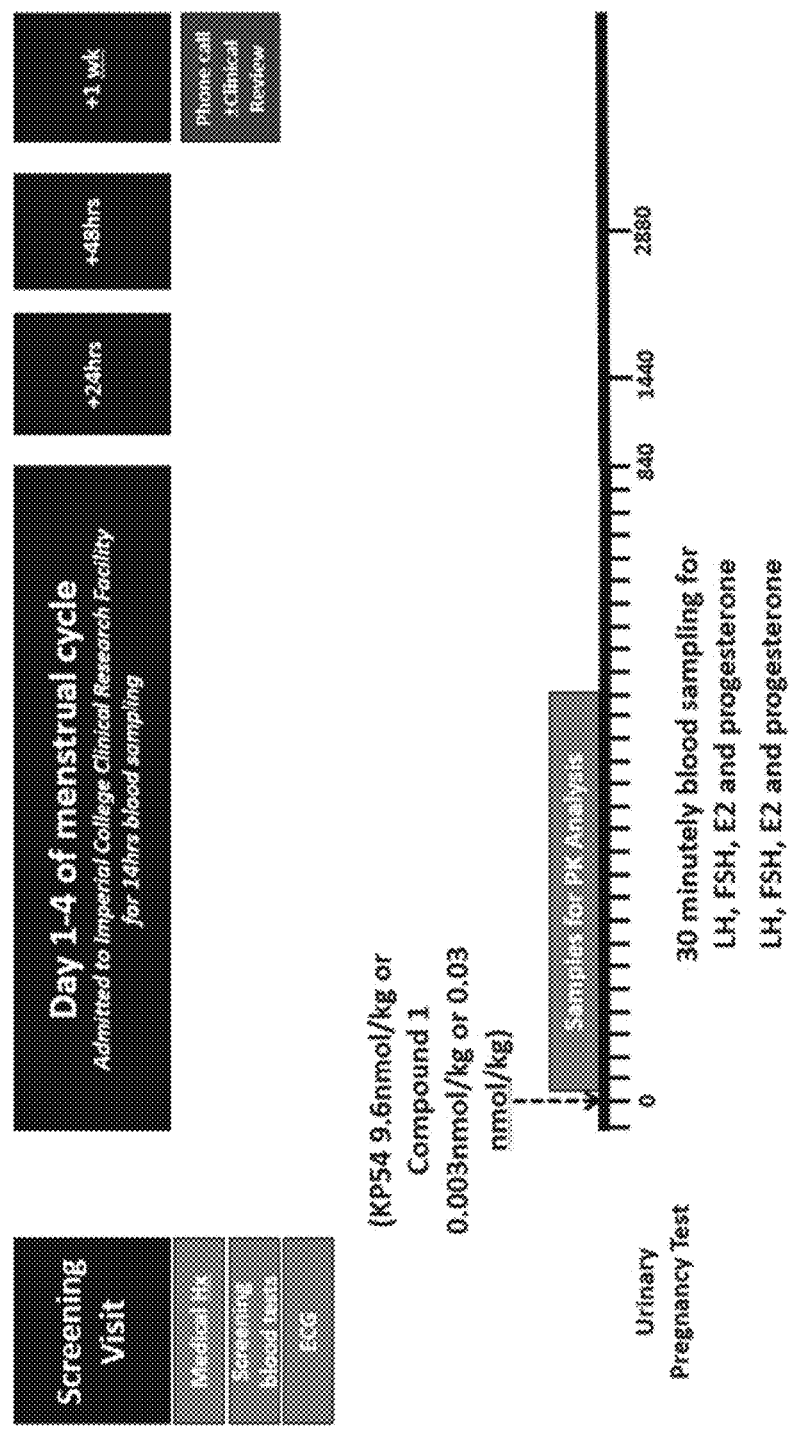
FIG. 14 illustrates the study design detailed in Example 11, Part 1.

The study included a screening visit to collect participants' full medical history and to conduct a general medical examination and blood testing. The three study periods each consisted of three planned study visits per study period (excluding screening and follow-up). Study Day 1 (SD1) Visit of each study period occurred during the follicular phase of the menstrual cycle (days 1-4), and the SD2 and SD3 Visits occurred at 24- and 48-hrs post-dose, respectively (FIG. 14). A follow-up phone call happened 7-10 days post-dose in each study period.

On Study Day 1, following confirmation of a negative urine pregnancy test, a single dose (via subcutaneous injection on the abdomen) of either Compound 1 (0.003 nmol/kg, or 0.03 nmol/kg) or Kisspeptin-54 (9.6 nmol/kg) was administered at time zero.

Immediately following dosing, serum LH, FSH, E2 (oestradiol), P (progesterone) and SHBG levels were assessed at 30 minute intervals for up to 14 hours (FIGS. 15A-15C, 16A-16C, 17, 18, 19, 20A, and 20B). These PD variables were also assessed at 24 (Study Day 2) and 48 hours (Study Day 3) post-dose. SHBG changes less rapidly and was measured every 3 hours to reduce blood volume.

Up to 3 mL of blood volume were required for measurement of serum reproductive hormone levels (LH, FSH, E2 and P). Blood samples for serum analysis were collected in plain Vacutainer tubes (Beckton Dickson, Franklin Lakes, N.J., USA), and spun after clotting (~1 hour at room temperature) for 10 minutes at 3000 rpm. Serum was then stored in a locked freezer at −20° C. until assay of serum reproductive hormone levels.

Plasma levels of Compound 1 and kisspeptin-54 were assessed for the first 6 hours to minimize withdrawal of excess blood volumes.

Figure 15A:
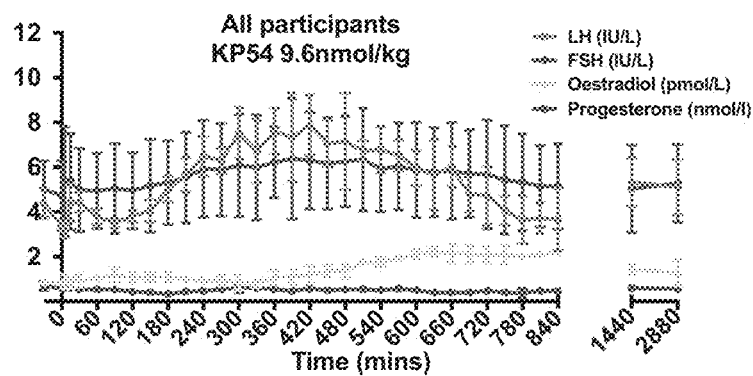
FIGS. 15A, 15B, and 15C illustrate the changes in LH, FSH, oestradiol, and progesterone over 48 hours after administration of 9.6 nmol/kg kisspeptin-54 (KP54), 0.003 nmol/kg Compound 1, and 0.03 nmol/kg Compound 1 to healthy women ages 18-35 as described in Example 11.
Figure 15B:
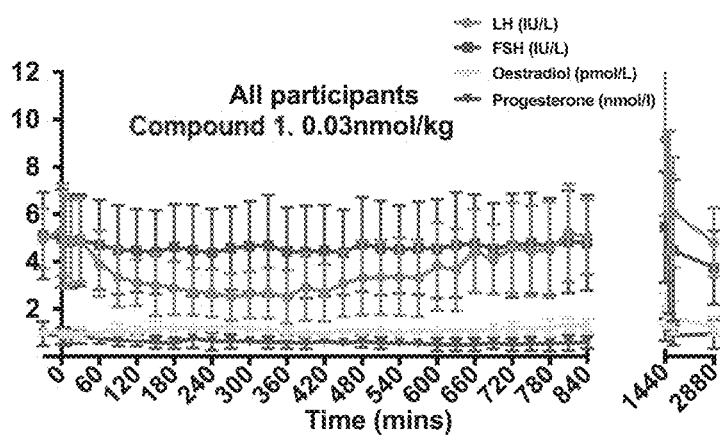
Figure 15C:
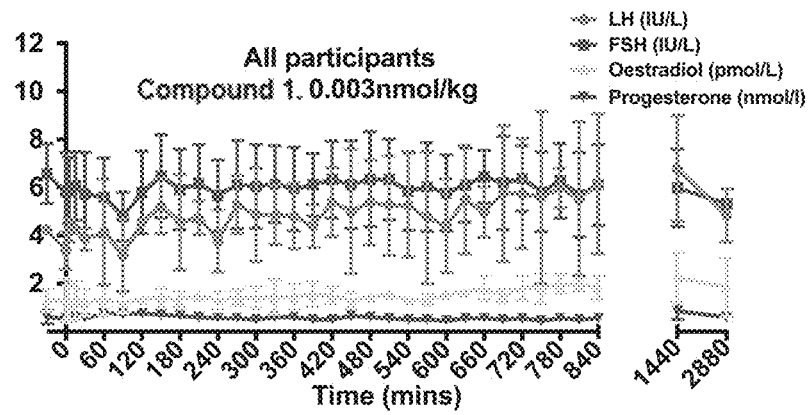
Figure 16A:
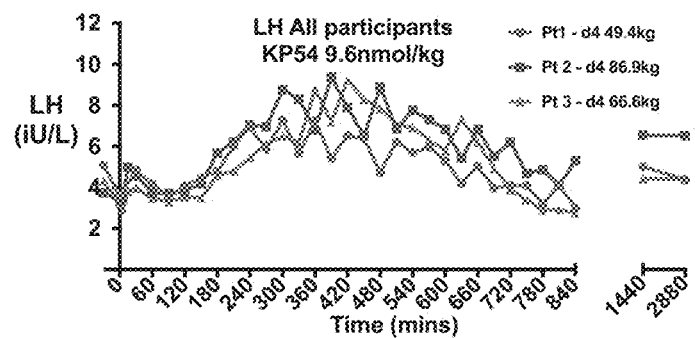
FIGS. 16A, 16B, and 16C illustrate the changes in LH over 48 hours after administration of 9.6 nmol/kg kisspeptin-54 (KP54), 0.003 nmol/kg Compound 1, and 0.03 nmol/kg Compound 1 to healthy women ages 18-35 as described in Example 11.
Figure 17:
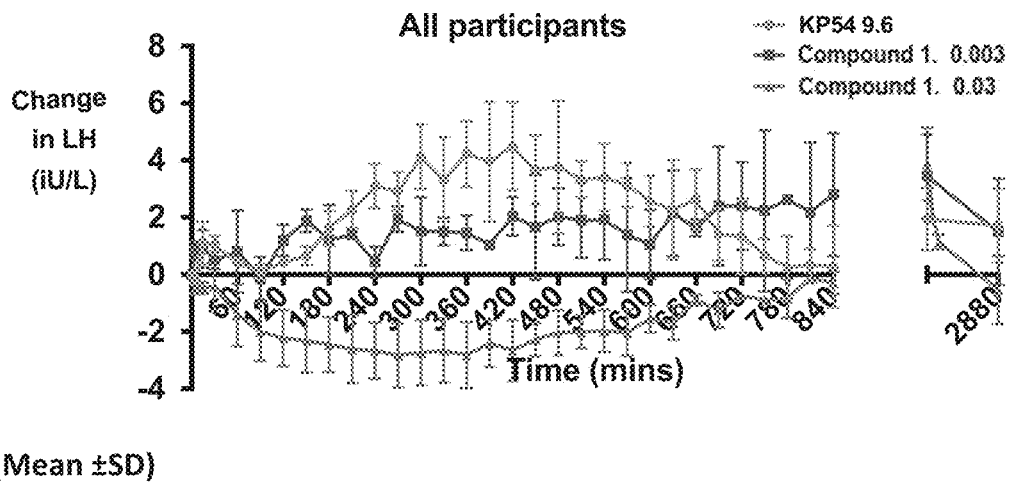
FIG. 17 illustrates the average changes in LH for all subjects over 48 hours after administration of 9.6 nmol/kg kisspeptin-54 (KP54), 0.003 nmol/kg Compound 1, and 0.03 nmol/kg Compound 1 to healthy women ages 18-35 as described in Example 11.
Figure 18:
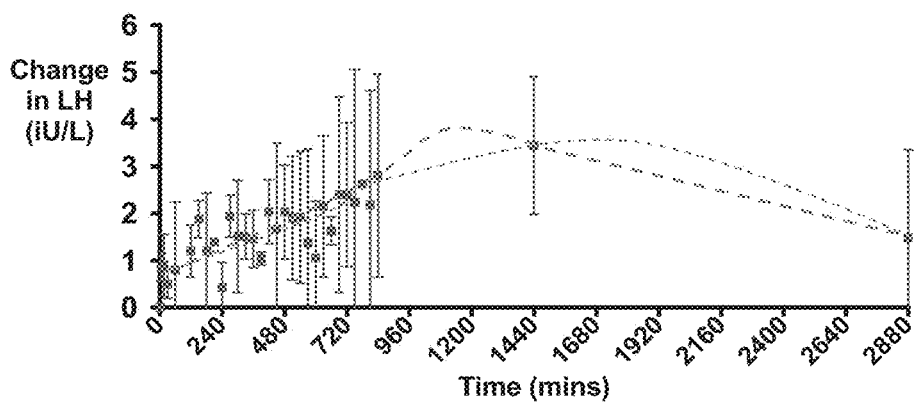
FIG. 18 illustrates the average changes in LH for all subjects over 48 hours after administration of 0.003 nmol/kg Compound 1 to healthy women ages 18-35 as described in Example 11.
Figure 19:
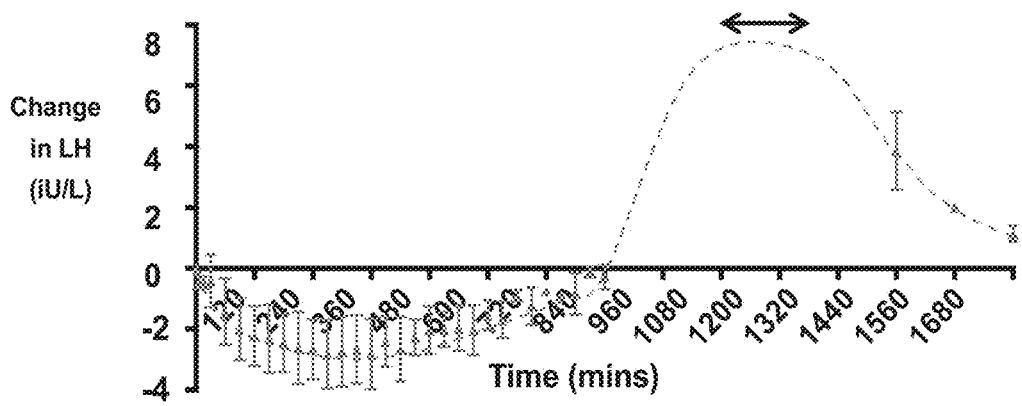
FIG. 19 illustrates the average changes in LH for all subjects over 48 hours after administration of 0.03 nmol/kg Compound 1 to healthy women ages 18-35 as described in Example 11.

As shown in FIGS. 15A and 16A, subjects receiving kisspeptin-54 showed an increase in LH peaking around 4-6 hours after kisspeptin-54 administration, with the LH surge lasting approximately 14 hours. Subjects receiving 0.003 nmol/kg Compound 1 (FIGS. 15C and 16B) and 0.03 nmol/kg Compound 1 (FIGS. 15B and 16C) also showed an increase in LH after Compound 1 administration, however, peak LH levels were achieved much later than observed with kisspeptin-54 administration and the LH surge lasted much longer (FIGS. 17-19). After administration of the 0.003 nmol/kg Compound 1 dose, peak serum LH levels were observed between 14-36 hours post-dosing and the LH surge lasted approximately 48 hours. With the 0.03 nmol/kg Compound 1 dose, following an initial LH decrease, peak serum LH levels were observed between 18-20 hours after administration and the LH surge lasted approximately 14 hours, ending 28 hours after administration. A longer LH surge is preferable in IVF to promote oocyte maturation. Further, observation of a long LH surge during the early follicular phase was unexpected, particularly as the kisspeptin-54 LH surge lasted only 14 hours compared to the approximately 48 hour surge observed with the 0.003 nmol/kg Compound 1 dose.

Figure 20A:
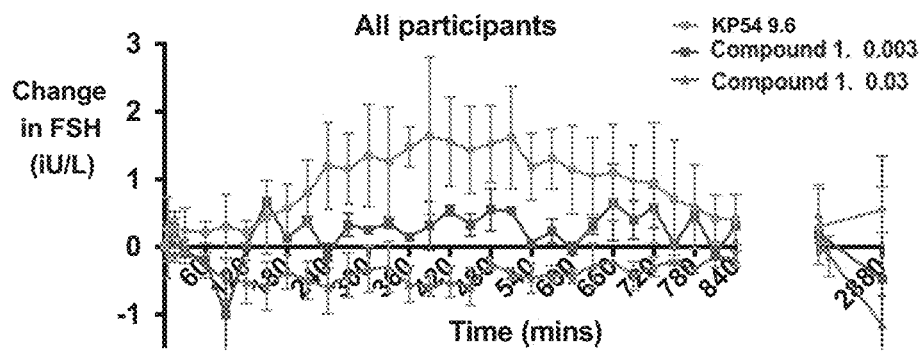
FIGS. 20A and 20B illustrate the changes in FSH and oestradiol over 48 hours after administration of 9.6 nmol/kg kisspeptin-54 (KP54), 0.003 nmol/kg Compound 1, and 0.03 nmol/kg Compound 1 to healthy women ages 18-35 as described in Example 11.
Figure 20B:
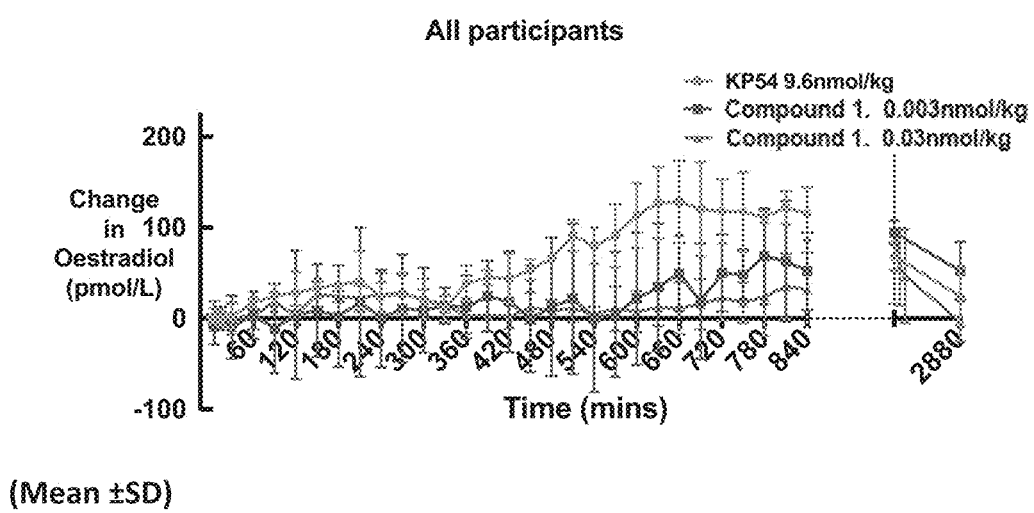

The small increases in E2 after Compound 1 administration were similar to those observed with kisspeptin-54 and are supportive of a similar mechanism of action in stimulating release of gonadotropins and sex hormones (FIG. 20B). Surprisingly, the FSH response was very low compared to the LH response, which is very different to the results observed in men where robust responses in both LH and FSH were evident (FIG. 20A and Example 7, FIGS. 8 and 9). Additionally, there was some potential desensitization of FSH response at the 24 and 48 hour time points, also not evident in men (FIGS. 9 and 20A).

Figure 16B:
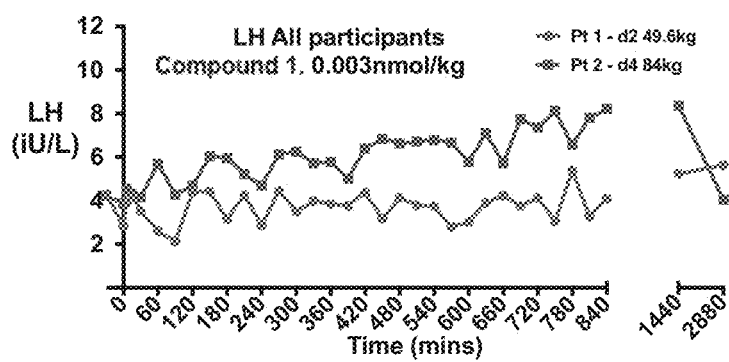
Figure 16C:
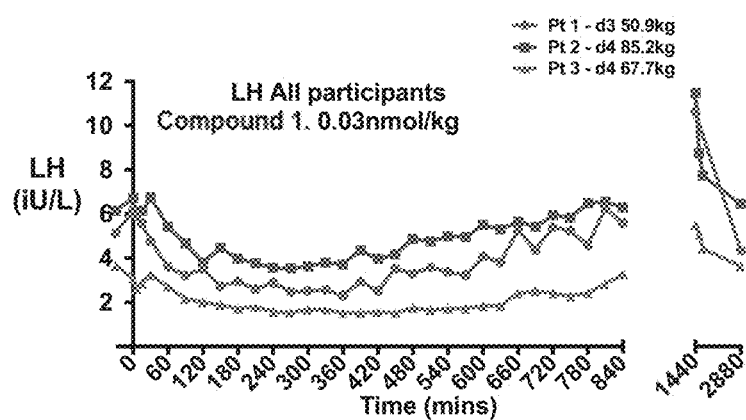

The 0.003 nmol/kg dose of Compound 1 only had two subjects' results as the third subject attended on what was believed to be day 4 of cycle following light menstrual bleeding (FIG. 16B). Her actual period arrived a few days later, and a serum progesterone level confirmed that she had actually been in the Luteal Phase of the previous cycle (day 36) during the study visit.

Part 2: Randomized, Open-Label, Cross-Over Study to Investigate the Effects of Compound 1 in Healthy Women In this part of the study, the objective is to identify doses of Compound 1 (administered during the follicular phase of the menstrual cycle) that provide the most optimal safety, tolerability and PD profile (namely LH response) in healthy women. Low, intermediate and high dose of Compound 1 that spans the dose range of Compound 1 identified in Part 1 will be compared with a dose of kisspeptin-54 (9.6 nmol/kg) known to be effective in triggering oocyte maturation during IVF treatment in previous studies, again aiming for an approximate 10-20% increase in peak LH response when compared to the kisspeptin-54 dose. This will allow the rapid identification of a dose of Compound 1 that might subsequently be used as a trigger agent in IVF therapy. A subcutaneous dose of a GnRH agonist (triptorelin 0.2 mg), currently used to trigger oocyte maturation during IVF therapy, will also be used to provide a comparison for Compound 1.

As noted previously, in Part 1 of this study, Compound 1 was administered during the follicular phase of the menstrual cycle, while the present phase occurs in a COS setting as part of ART prior to IVF. Thus, the amplitude of the LH surge is expected to differ from the amplitude of the LH surge observed when Compound 1 was administered during the follicular phase.

The study population will include 8 healthy women, aged 18-35 years, with BMI 18-30 kg/m$^2$, no medical problems and not taking any medications or hormonal contraception. The screening visit for this study will collect the same information detailed in Part 1.

This part of the study will consist of six study periods. A Follow-up Visit will occur within 7-10 days post-dose in each study period. Eight subjects will be randomized to receive a single dose of each of the 6 study regimens (one regimen per study period). All women will be scheduled for 6 Study Day 1 Visits (each during the follicular phase of the menstrual cycle). Each subject will receive a single dose of one of the following 6 study regimens on the Study Day 1 Visit during each study period, such that at the end of this part of the study, each subject will have received all 6 study regimens (one per study period):

Normal Saline (0.9%) 100 μL

Compound 1 LOW dose, e.g., 0.003 nmol/kg* or 0.00368 mcg/kg (or alternate LOW dose confirmed following part 1)

Compound 1 INTERMEDIATE dose, e.g., 0.01 nmol/kg* or 0.0123 mcg/kg (or alternate INTERMEDIATE dose confirmed following part 1)

Compound 1 HIGH dose, e.g., 0.03 nmol/kg* or 0.0368 mcg/kg (or alternate HIGH dose confirmed following part 1)

Kisspeptin-54 9.6 nmol/kg

GnRH agonist (triptorelin 0.2 mg SC)

*For example, a 60 kg woman who is administered the 0.003 nmol/kg dose of Compound 1, would receive 0.18 nmols or 0.221 mcg. The order in which individual women receive one of the six study regimens will be determined by a randomization matrix.

On Study Day 1, following confirmation of a negative urine pregnancy test, a single dose (via subcutaneous injection on the abdomen) of either Compound 1 (LOW, e.g., 0.003 nmol/kg; INTERMEDIATE, e.g., 0.01 nmol/kg; or HIGH, e.g., 0.03 nmol/kg), Kisspeptin-54 (9.6 nmol/kg), GnRH agonist (triptorelin 0.2 mg) or normal saline (0.9%, 100 µl), will be administered at time zero.

Blood sampling, testing, drug storage, and dose preparation will occur as in Part 1.

Part 3: Randomized, Open-Label, Cross-Over Study to Evaluate the Effects of Compound 1 in Women with Anovulatory PCOS In this part of the study, the objective is to compare the PK/PD profile (in particular, LH and FSH response) of the optimal dose of Compound 1 (identified in Part 2 in healthy women) with the PK/PD profile seen in women with anovulatory PCOS. Women will be diagnosed as anovulatory PCOS if oligomenorrheic (menstrual cycle length>35 days), increased serum AMH (>35 pmol/L) or antral follicle count on ultrasound>23, ±clinical or hormonal evidence of hyperandrogenism. Based on previous studies using kisspeptin-54, a similar, but slightly higher LH response is expected in women with PCOS compared to healthy women. The response to a single dose of Compound 1 will also be compared to that of a GnRH agonist (triptorelin 0.2 mg), a therapy commonly used in women with PCOS to trigger oocyte maturation. This will allow comparison of the optimal dose of Compound 1 (previously identified in Part 2) with current standard therapy.

The study population will be women, aged 18-35 years, with anovulatory PCOS.

The screening visit for this study will collect the same information detailed in Part 1, but will also have the following two additions: 1) Prior to SD1, women will be induced with Provera (administered as a 10 mg BID for one week just prior to SD1). 2) Following the Provera-induced run-in, women will begin each study period, as was done in Part 1 and 2, beginning on day 1-4 of their Provera-induced menstrual cycle (follicular phase).

Eight subjects will be randomized to receive a single dose of each of the 4 study drug regimens (one regimen per study period) per the randomization matrix. All women will be scheduled for 4 Study Day 1 Visits (each during the follicular phase of the menstrual cycle in consecutive months). Each subject will receive a single dose of one of the following four (4) study regimens on the Study Day 1 Visit during each study period, such that at the end of this part of the study, each subject will have received all 4 of the following study regimens (one per study period):

Normal Saline (0.9%) 100 µL

Compound 1*

KP54 9.6 nmol/kg SC

GnRH agonist (triptorelin 0.2 mg SC)

*The Compound 1 dose will be confirmed in Part 2 (healthy volunteer) of the study and the duration of blood sampling for PD analysis following each study regimen will be confirmed following part 1 of the study, e.g., the duration of blood sampling following Compound 1 may be reduced from 14 hours to 8-12 hours, following kisspeptin-54 to 8-10 hours and following normal saline to 6-8 hours.

On Study Day 1, following confirmation of a negative urine pregnancy test, a single dose (via subcutaneous injection on the abdomen) of the optimal Compound 1 dose (as determined in Part 2 of the study), Kisspeptin-54 (9.6 nmol/kg), GnRH agonist (0.2 mg triptorelin) or normal saline (0.9%, 100 µl) will be administered at time zero.

Blood sampling, testing, drug storage, and dose preparation will occur as in Parts 1 and 2.

ENUMERATED EMBODIMENTS

Some embodiments of the disclosure relate to Embodiment I:

Embodiment I-1. A method for promoting egg maturation and inducing ovulation in assisted reproductive technologies (ART), such as IVF or in an embryo transfer (ET) process, the method comprising: administering to a female human subject a therapeutically effective amount of about 0.001 mg to about 600 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a corresponding amount of a pharmaceutically acceptable salt thereof.

Embodiment I-2. The method of Embodiment I-1, wherein the pharmaceutically acceptable salt is 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide monoacetate.

Embodiment I-3. The method of Embodiment I-1, wherein the therapeutically effective amount of about 0.001 mg to about 600 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a corresponding amount of a pharmaceutically acceptable salt thereof is administered via injection.

Embodiment I-4. The method of Embodiment I-1, wherein the therapeutically effective amount of about 0.001 mg to about 600 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a corresponding amount of a pharmaceutically acceptable salt thereof is administered in the form of a delayed release, single dose.

Embodiment I-5. The method of Embodiment I-1, wherein 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide is represented by the formula:

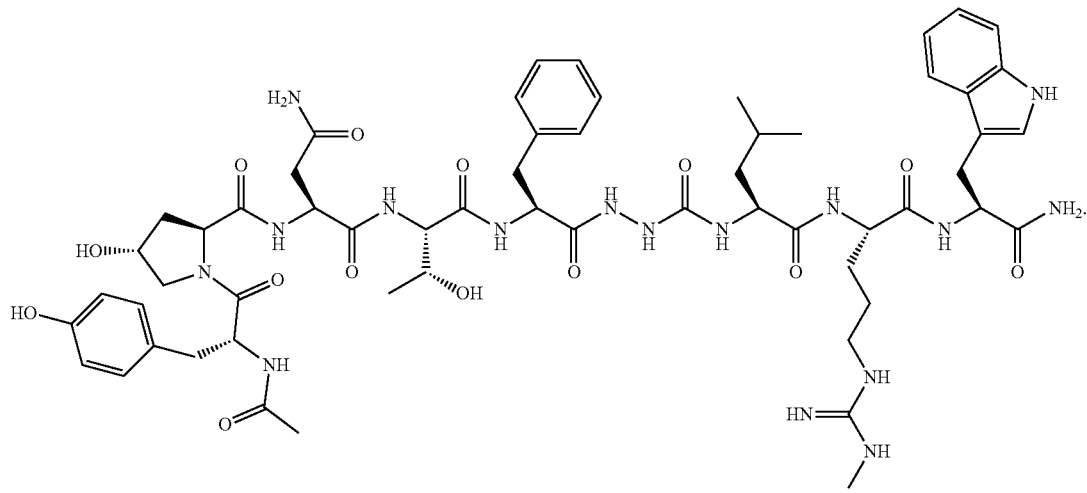 [SMILES: CNC(=N)NCCC[C@H](NC(=O)[C@H](CC(C)C)NC(=O)NNC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O]

Embodiment I-6. The method of Embodiment I-2, wherein the 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide monoacetate is represented by the formula:

hydrazinocarbonyl-L-leucyl-Nω-methyl-L-arginyl-L-tryptophanamide or a corresponding amount of a pharmaceutically acceptable salt thereof.

Embodiment I-9. The method of Embodiment I-8, wherein the pharmaceutically acceptable salt thereof is

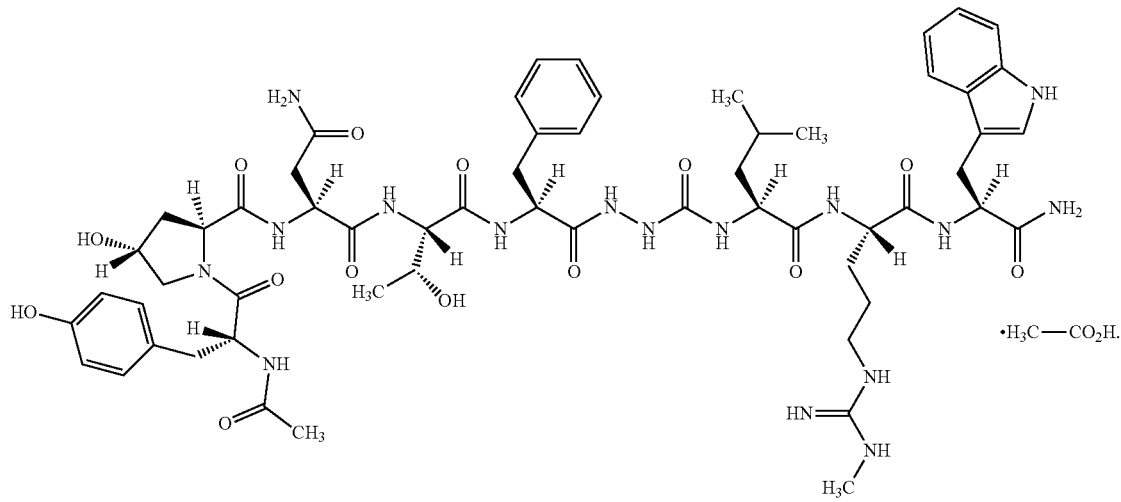

Embodiment I-7. The method of Embodiment I-1, wherein the administration of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, triggers ovulation in the human female subject (i) without increasing levels of VEGF or (ii) increasing levels of VEGF for less than 24 hours.

Embodiment I-8. A method for promoting egg maturation in ART, such as IVF or in an ET process, the method comprising: administering to a female human subject, via injection, a therapeutically effective amount of about 0.001 mg to about 5 mg of 2-(N-acetyl-D-tyrosyl-trans-4-hydroxy-L-prolyl-L-asparaginyl-L-threonyl-L-phenylalanyl)

2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide monoacetate.

Embodiment I-10. The method of Embodiment I-8, wherein the administration is subcutaneous.

Embodiment I-11. The method of Embodiment I-8, wherein the administration is intramuscular.

Embodiment I-12. The method of Embodiment I-8, wherein the administration is intravenous.

Embodiment I-13. The method of Embodiment I-8, wherein 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide is represented by the formula:

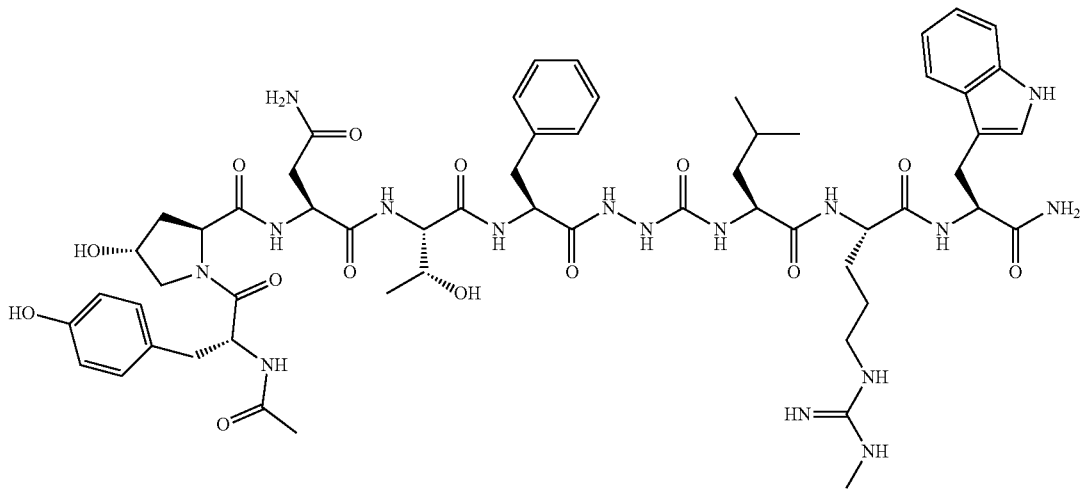 [SMILES: CNC(=N)NCCC[C@H](NC(=O)[C@H](CC(C)C)NC(=O)NNC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O]

Embodiment I-14. The method of Embodiment I-8, wherein 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide monoacetate is represented by the formula:

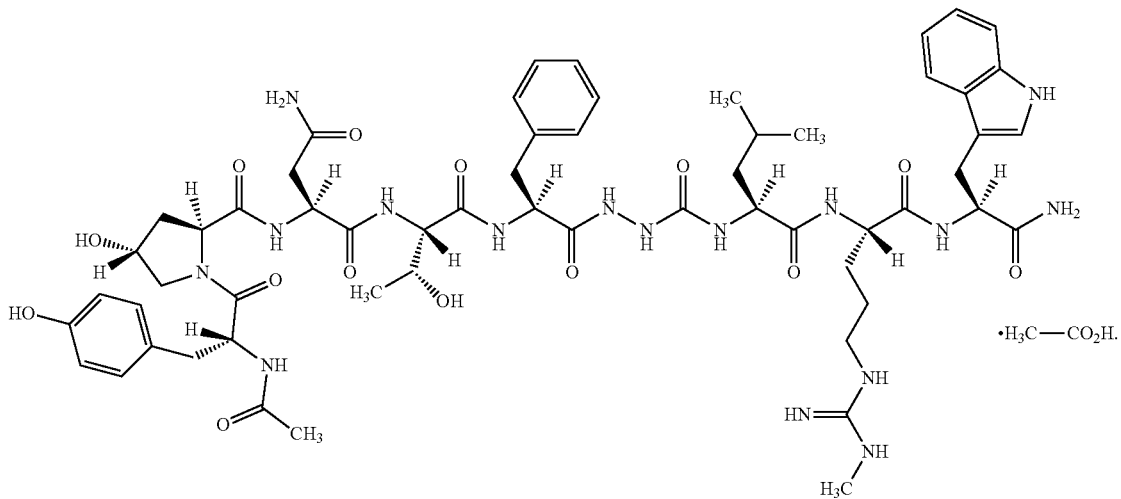

Embodiment I-15. A method for promoting egg maturation in ART, such as IVF or in an ET process, the method comprising: administering to a female human subject, by intranasal route, a therapeutically effective amount of about 0.001 mg to about 5 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a corresponding amount of a pharmaceutically acceptable salt thereof.

Embodiment I-16. The method of Embodiment I-15, wherein the pharmaceutically acceptable salt is 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide monoacetate.

Embodiment I-17. The method of Embodiment I-15, wherein 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide is represented by the formula:

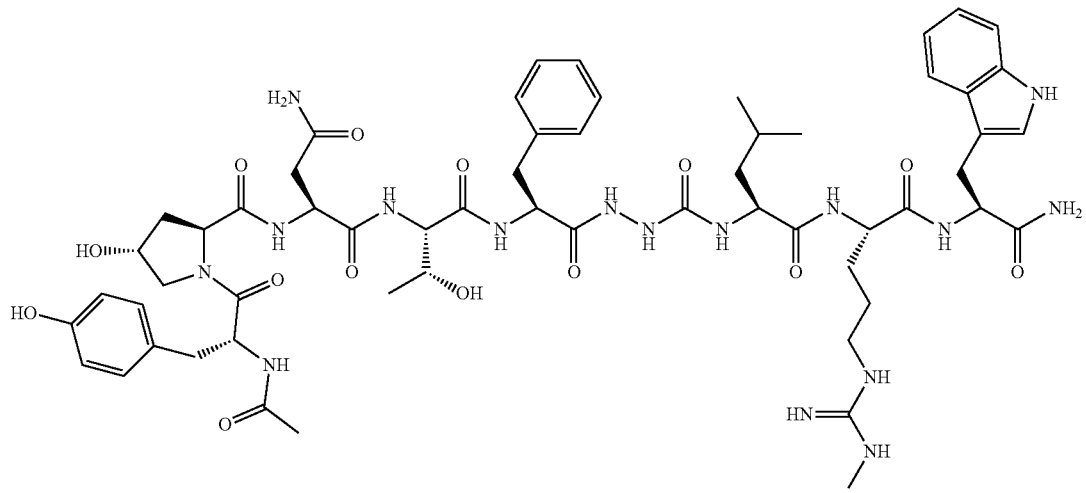 [SMILES: CNC(=N)NCCC[C@H](NC(=O)[C@H](CC(C)C)NC(=O)NNC(=O)[C@H](Cc1ccccc1)NC(=O)[C@@H](NC(=O)[C@H](CC(N)=O)NC(=O)[C@@H]1C[C@@H](O)CN1C(=O)[C@@H](Cc1ccc(O)cc1)NC(C)=O)[C@@H](C)O)C(=O)N[C@@H](Cc1c[nH]c2ccccc12)C(N)=O]

Embodiment I-18. The method of Embodiment I-15, wherein 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide monoacetate is represented by the formula:

2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide monoacetate.

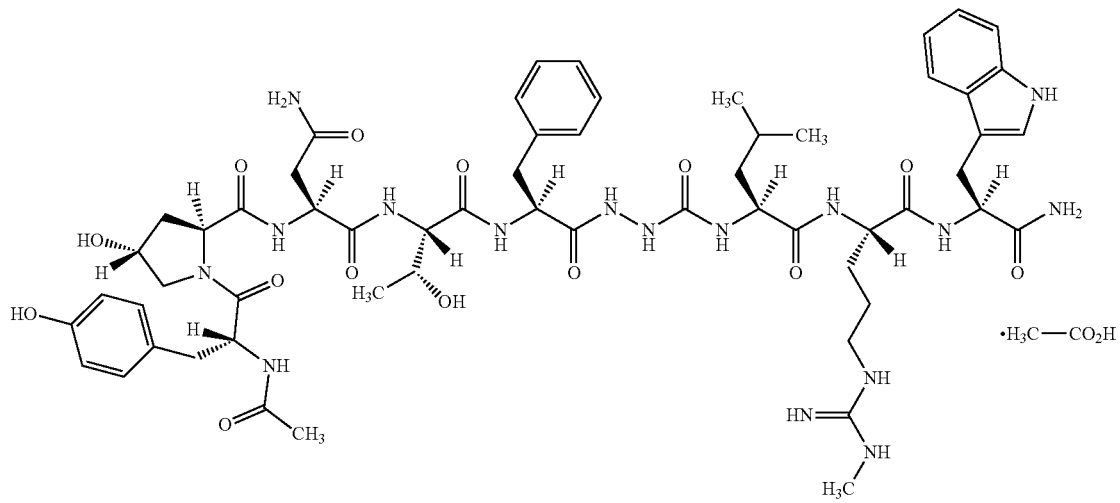

Embodiment I-19. A method for inducing ovulation in ART, such as IVF or in an ET process, the method comprising the following: administering to a human female subject one or more human gonadotropins, coupled with a GnRH agonist or antagonist (~2-3 days later) to facilitate an initial COS phase and prevent premature ovulation in ART, such as IVF and/or an ET process, wherein the initial COS phase is followed by the administration of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, to effectively promote maturation of oocytes and induce ovulation (i) without increasing the total blood concentration level of VEGF or (ii) by increasing the total level of VEGF for less than 24 hours.

Embodiment I-20. The method of Embodiment I-19, wherein the pharmaceutically acceptable salt thereof is Embodiment I-21. The method of Embodiment I-19, wherein 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, is administered in an amount from about 0.001 mg to about 600 mg.

Embodiment I-22. The method of Embodiment I-19, wherein 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, is administered via injection in an amount from about 0.001 mg to about 5 mg.

Embodiment I-23. The method of Embodiment I-19, wherein 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, is administered intranasally in an amount from about 0.001 mg to about 5 mg.

Embodiment I-24. The method of Embodiment I-19, wherein the one or more human gonadotropins are administered orally or via injection and consist of a follicle stimulating hormone, a luteinizing hormone, or a combination thereof.

Embodiment I-25. The method of Embodiment I-19, wherein if a GnRH agonist is used in the COS phase in the same protocol as 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, (as the trigger agent), the GnRH agonist is a combination of leuprorelin acetate, and if a GnRH antagonist is used in the COS phase in the same protocol as 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, (as the trigger agent), the GnRH antagonist is selected from the group consisting of ganirelix, cetrorelix, relugolix, and pharmaceutically acceptable salts of any of the foregoing.

Embodiment I-26. The method of Embodiment I-19, wherein the GnRH agonist is selected from the group consisting of leuprorelin acetate, gonadorelin, buserelin, triptorelin, goserelin, nafarelin, histrelin, deslorelin, meterelin, lecirelin, and pharmaceutically acceptable salts of any of the foregoing.

Embodiment I-27. The method of Embodiment I-19, wherein the GnRH antagonist is relugolix, or a pharmaceutically acceptable salt thereof.

Embodiment I-28. The method of Embodiment I-19, wherein the GnRH antagonist is selected from the group consisting of cetrorelix, ganirelix, abarelix, nal-blu, antide, azaline B, degarelix, D63153, relugolix, teverelix, and pharmaceutically acceptable salts of any of the foregoing.

Embodiment I-29. A method of reducing the rate of OHSS in ART, such as IVF or in an ET process, wherein 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, is used as the trigger agent as compared to hCG-based trigger agents.

Embodiment I-30. A method of comparable or improved pregnancy rates in ART, such as IVF or in an ET process, wherein 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, is used as the trigger agent as compared to GnRH agonist or hCG-based trigger agents.

Embodiment I-31. A method of shorter time to pregnancy in ART, such as IVF or in an ET process, wherein 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, is used as the trigger agent as compared to hCG-based trigger agents.

Embodiment I-32. A method for inducing ovulation in an anovulatory, human female subject suffering from secondary ovarian failure, comprising the steps of (1) pretreating the subject with one or more human gonadotropins and (2) administering to the subject a therapeutically effective amount of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof.

Embodiment I-33. A method of preventing premature ovulation during the COS phase of ART, such as IVF and/or in an ET process, wherein relugolix, or a pharmaceutically acceptable salt thereof, is used as compared to the use of a GnRH agonist in the COS phase.

Some embodiments of the disclosure relate to Embodiment II:

Embodiment II-1. A method of elevating endogenous LH level in a woman in need thereof, the method comprising: administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, wherein the woman is undergoing ART and is at risk for OHSS, and wherein after the initial dose is administered, the woman's endogenous LH level in blood is elevated compared to the woman's endogenous LH level in blood prior to administration of the initial dose.

Embodiment II-2. A method of increasing endogenous LH level in a woman in need thereof undergoing ART, the method comprising: administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, wherein the woman is undergoing ART, and wherein at least 36 hours after the initial dose is administered, the woman's endogenous LH level in blood is elevated compared to the woman's endogenous LH level in blood prior to administration of the initial dose.

Embodiment II-3. A method of increasing endogenous LH level in a woman in need thereof undergoing ART, the method comprising: administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, wherein the woman is undergoing ART, and wherein the maximum endogenous LH level in blood occurs at least about 12 hours after administration of the initial dose.

Embodiment II-4. The method of Embodiment II-3, wherein the maximum endogenous LH level in blood occurs between about 12 hours and about 48 hours after administration of the initial dose.

Embodiment II-5. A method of increasing endogenous LH level in a woman undergoing ART and in need of luteal phase support, the method comprising: administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, after said woman has received a trigger dose of an oocyte maturation agent as part of an ART regimen.

Embodiment II-6. The method of any one of the preceding Embodiments, wherein the woman's endogenous LH level in blood is elevated between about 12 hours to about 96 hours after administration of the initial dose compared to the woman's endogenous LH level in blood prior to administration of the initial dose.

Embodiment II-7. The method of any one of the preceding Embodiments, wherein the woman's endogenous LH level in blood is elevated for at least 36 hours after administration of the initial dose compared to the woman's endogenous LH level in blood prior to administration of the initial dose.

Embodiment II-8. The method of Embodiment II-7, wherein the endogenous LH level in blood is elevated for about 36 hours to about 16 days.

Embodiment II-9. The method of Embodiment II-7, wherein the endogenous LH level in blood is elevated for about 36 hours to about 12 days.

Embodiment II-10. The method of any one of the preceding Embodiments, wherein the administration of the initial dose promotes oocyte maturation.

Embodiment II-11. The method of Embodiment II-10, wherein oocyte maturation occurs without the administration of exogenous hCG or exogenous LH.

Embodiment II-12. The method of Embodiment II-10 or II-11, wherein oocyte maturation occurs after administration of a GnRH agonist.

Embodiment II-13. The method of Embodiment II-10, wherein oocyte maturation occurs after administration of exogenous hCG.

Embodiment II-14. The method of any one of Embodiments II-10 to II-13, wherein the yield of mature oocytes is at least 50%.

Embodiment II-15. The method of any one of the preceding Embodiments, wherein after administration of the initial dose, the woman does not experience one or more symptoms selected from the group consisting of ascites, pleural effusion and reduced renal perfusion.

Embodiment II-16. The method of any one of the preceding Embodiments, wherein after administration of the initial dose, ovary size may not increase to greater than 5 cm in diameter.

Embodiment II-17. The method of any one of the preceding Embodiments, wherein the woman does not experience one or more symptoms of OHSS after administration of the initial dose.

Embodiment II-18. The method of any one of Embodiments II-1 to II-16, wherein after administration of the initial dose, the woman does not experience a worsening of one or more symptoms of OHSS.

Embodiment II-19. The method of any one of the preceding Embodiments, wherein the initial dose is administered when at least three ovarian follicles of at least 14 mm are visible via ultrasound.

Embodiment II-20. The method of any one of the preceding Embodiments, wherein the initial dose is administered when at least three ovarian follicles of at least 18 mm are visible via ultrasound.

Embodiment II-21. The method of any one of the preceding Embodiments, wherein the initial dose is administered when serum estradiol concentration is at least 0.49 nmol/L.

Embodiment II-22. The method of any one of the preceding Embodiments, wherein the method further comprises administration of FSH about 5 days to about 12 days prior to administration of the initial dose.

Embodiment II-23. The method of any one of the preceding Embodiments, wherein the method further comprises administration of a GnRH antagonist about 2 days to about 10 days prior to administration of the initial dose.

Embodiment II-24. The method of Embodiment II-23, wherein the GnRH antagonist is selected from the group consisting of relugolix, elagolix, cetrorelix, ganirelix, abarelix, nal-blu, antide, azaline B, degarelix, D63153 (ozarelix), OBE2109, and teverelix.

Embodiment II-25. The method of any one of Embodiment II-1 to II-24, wherein the method further comprises administration of a GnRH agonist from about 14 to about 28 days prior to administration of the initial dose.

Embodiment II-26. The method of Embodiment II-25, wherein the GnRH agonist is selected from the group consisting of leuprorelin acetate, gonadorelin, buserelin, triptorelin, goserelin, nafarelin, histrelin, deslorelin, meterelin, and lecirelin.

Embodiment II-27. The method of any one of the preceding Embodiments, wherein the initial dose is administered prior to oocyte retrieval.

Embodiment II-28. The method of any one of Embodiments II-1 to II-27, wherein the initial dose is administered after oocyte retrieval.

Embodiment II-29. The method of any one of Embodiments II-1 to II-27, wherein the initial dose is administered prior to ovulation.

Embodiment II-30. The method of any one of Embodiments II-1 to II-27, wherein the initial dose is administered after ovulation.

Embodiment II-31. The method of any one of the preceding Embodiments, wherein the initial dose is administered after administration of a GnRH agonist as an oocyte maturation agent.

Embodiment II-32. The method of Embodiment II-31, wherein the GnRH agonist is selected from the group consisting of leuprorelin acetate, gonadorelin, buserelin, triptorelin, goserelin, nafarelin, histrelin, deslorelin, meterelin, and lecirelin.

Embodiment II-33. The method of any one of the preceding Embodiments, wherein the method further comprises administering a second dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

Embodiment II-34. The method of Embodiment II-33, wherein the second dose is administered within about 8 to about 60 hours after administration of the initial dose.

Embodiment II-35. The method of Embodiment II-33 or II-34, wherein the method further comprises administering a third dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

Embodiment II-36. The method of Embodiment II-35, wherein the third dose is administered within about 8 to about 60 hours after administration of the second dose.

Embodiment II-37. The method of Embodiment II-35 or II-36, further comprising administration of one to five additional doses of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

Embodiment II-38. The method of Embodiment II-37, wherein the administration of the one to five additional doses is within about 8 to about 60 hours after the prior additional dose is administered.

Embodiment II-39. The method of any one of the preceding Embodiments, wherein the method further comprises administering one or more doses of a progestogen.

Embodiment II-40. The method of any one of Embodiments II-1 to II-38, wherein the method does not comprise administering one or more doses of a progestogen.

Embodiment II-41. The method of any one of the preceding Embodiments, wherein the method further comprises oocyte retrieval.

Embodiment II-42. The method of Embodiment II-41, wherein the woman's pituitary is desensitized to GnRH prior to administration of the initial dose.

Embodiment II-43. The method of any one of the preceding Embodiments, wherein the method further comprises implantation of an embryo.

Embodiment II-44. The method of Embodiment II-43, wherein the implantation occurs within about 2 to about 10 days after administration of the initial dose.

Embodiment II-45. The method of Embodiment II-43 or II-44, wherein the implantation occurs within about 1 to about 7 days after oocyte retrieval.

Embodiment II-46. The method of any one of Embodiments II-43 to II-45, wherein the embryo has not been frozen.

Embodiment II-47. The method of Embodiment II-46, wherein the embryo is implanted within the same menstrual cycle as oocyte retrieval.

Embodiment II-48. The method of any one of Embodiments II-1 to II-23, II-25 to II-26, or II-28 to II-30, wherein the method induces ovulation.

Embodiment II-49. The method of Embodiment II-48, wherein the woman conceives via intercourse or intrauterine insemination after administration of at least the initial dose.

Embodiment II-50. The method of any one of the preceding Embodiments, wherein after administration of at least the initial dose, the woman conceives and/or gives birth.

Embodiment II-51. The method of any one Embodiments II-1 to II-4 or II-6 to II-50, wherein one or more of the initial dose, second dose, third dose, or one to five additional doses promotes luteal phase support.

Embodiment II-52. The method of any one of the preceding Embodiments, wherein one or more of the initial dose, second dose, third dose, or one to five additional doses are administered via injection.

Embodiment II-53. The method of Embodiment II-52, wherein the injection is an intramuscular or subcutaneous injection.

Embodiment II-54. The method of any one of the preceding Embodiments, wherein any one or more of the initial dose, second dose, third dose, or one to five additional doses is from about 0.0003 mg to about 0.03 mg.

Embodiment II-55. The method of any one of the preceding Embodiments, wherein the woman is undergoing COS.

Embodiment II-56. The method of any one of the preceding Embodiments, wherein the ART therapy is selected from the group consisting of oocyte donation, oocyte banking, intracytoplasmic sperm injection (ICSI), IVF, embryo transfer (ET) process, ovulation induction, and intrauterine insemination.

Embodiment II-57. The method of any one of the preceding Embodiments, wherein the woman has one or more of PCOS, serum AMH greater than 15 pmol/L, total AFC greater than 23 via ultrasound, serum estradiol E2 greater than 3000 pg/mL, or has experienced one or more previous episodes of OHSS.

Embodiment II-58. The method of any one of the preceding Embodiments, wherein the woman is any one or more of anovulatory, or of advanced maternal age, or is experiencing secondary ovarian failure, oligomenorrhea, amenorrhea, endometriosis, or polyscystic ovarian syndrome (PCOS).

Embodiment II-59. A method of inducing final follicular maturation and early luteinization in a woman in need thereof, wherein said woman is undergoing ART, has undergone pituitary desensitization and has been pretreated with follicle stimulating hormones as part of ART, said method comprising administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, and wherein after the initial dose is administered, the woman's endogenous LH level in blood is elevated compared to the woman's endogenous LH level in blood prior to administration of the initial dose.

Embodiment II-60. A method of inducing ovulation in a woman in need thereof, wherein said woman is anovulatory infertile and wherein said infertility is not due to primary ovarian failure, said method comprising administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, and wherein after the initial dose is administered, the woman's endogenous LH level in blood is elevated compared to the woman's endogenous LH level in blood prior to administration of the initial dose.

Embodiment II-61. The method of Embodiment II-59 or II-60, wherein the woman is at risk for OHSS.

Embodiment II-62. The method of any one of Embodiments II-59 to II-61, wherein at least 36 hours after the initial dose is administered, the woman's endogenous LH level in blood is elevated compared to the woman's endogenous LH level in blood prior to administration of the initial dose.

Embodiment II-63. The method of any one of Embodiments II-59 to II-62, wherein the maximum endogenous LH level in blood occurs at least about 12 hours after administration of the initial dose.

Embodiment II-64. The method of Embodiment II-63, wherein the maximum endogenous LH level in blood occurs between about 12 hours and about 48 hours after administration of the initial dose.

Embodiment II-65. The method of any one of Embodiments II-59 to II-64, wherein the woman's endogenous LH level in blood is elevated between about 12 hours to about 96 hours after administration of the initial dose compared to the woman's endogenous LH level in blood prior to administration of the initial dose.

Embodiment II-66. The method of any one of Embodiments II-59 to II-65, wherein the woman's endogenous LH level in blood is elevated for at least 36 hours after administration of the initial dose compared to the woman's endogenous LH level in blood prior to administration of the initial dose.

Embodiment II-67. The method of Embodiment II-66, wherein the endogenous LH level in blood is elevated for about 36 hours to about 16 days.

Embodiment II-68. The method of Embodiment II-66, wherein the endogenous LH level in blood is elevated for about 36 hours to about 12 days.

Embodiment II-69. The method of any one of the preceding Embodiments, wherein the woman experiences anovulatory infertility not due to primary ovarian failure.

Embodiment II-70. The method of any one of the preceding Embodiments, said method comprising administering to the woman an initial dose of about 0.001 mg to about 0.003 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

Embodiment II-71. The method of any one of Embodiments II-1 to II-69, said method comprising administering to the woman an initial dose of about 0.001 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

Embodiment II-72. The method of any one of Embodiments II-1 to II-69, said method comprising administering to the woman an initial dose of about 0.0003 mg to about 0.003 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

Embodiment II-73. 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for use in a method of elevating endogenous LH level in a woman who is undergoing ART and who is at risk for OHSS, the method comprising: administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of the pharmaceutically acceptable salt thereof.

Embodiment II-74. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-73, wherein after the initial dose is administered, the woman's endogenous LH level in blood is elevated compared to the woman's endogenous LH level in blood prior to administration of the initial dose.

Embodiment II-75. 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for use in a method of increasing endogenous LH level in a woman undergoing ART, the method comprising: administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of the pharmaceutically acceptable salt thereof.

Embodiment II-76. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-75, wherein at least 36 hours after the initial dose is administered, the woman's endogenous LH level in blood is elevated compared to the woman's endogenous LH level in blood prior to administration of the initial dose.

Embodiment II-77. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-75, wherein the maximum endogenous LH level in blood occurs at least about 12 hours after administration of the initial dose.

Embodiment II-78. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-75, wherein the woman has received a trigger dose of an oocyte maturation agent as part of an ART regimen prior to administration of the initial dose of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or the pharmaceutically acceptable salt thereof.

Embodiment II-79. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the initial dose is administered when at least three ovarian follicles of at least 14 mm are visible via ultrasound.

Embodiment II-80. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the initial dose is administered when at least three ovarian follicles of at least 18 mm are visible via ultrasound.

Embodiment II-81. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the initial dose is administered when serum estradiol concentration is at least 0.49 nmol/L.

Embodiment II-82. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the method further comprises administration of FSH about 5 days to about 12 days prior to administration of the initial dose.

Embodiment II-83. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the method further comprises administration of a GnRH antagonist about 2 days to about 10 days prior to administration of the initial dose.

Embodiment II-84. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-83, wherein the GnRH antagonist is selected from the group consisting of relugolix, elagolix, cetrorelix, ganirelix, abarelix, nal-blu, antide, azaline B, degarelix, D63153 (ozarelix), OBE2109, and teverelix.

Embodiment II-85. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of Embodiments II-73 to II-84, wherein the method further comprises administration of a GnRH agonist from about 14 to about 28 days prior to administration of the initial dose.

Embodiment II-86. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-85, wherein the GnRH agonist is selected from the group consisting of leuprorelin acetate, gonadorelin, buserelin, triptorelin, goserelin, nafarelin, histrelin, deslorelin, meterelin, and lecirelin.

Embodiment II-87. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the initial dose is administered prior to oocyte retrieval.

Embodiment II-88. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of Embodiments II-73 to II-87, wherein the initial dose is administered after oocyte retrieval.

Embodiment II-89. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of Embodiments II-73 to II-87, wherein the initial dose is administered prior to ovulation.

Embodiment II-90. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of Embodiments II-73 to II-87, wherein the initial dose is administered after ovulation.

Embodiment II-91. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the initial dose is administered after administration of a GnRH agonist as an oocyte maturation agent.

Embodiment II-92. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-91, wherein the GnRH agonist is selected from the group consisting of leuprorelin acetate, gonadorelin, buserelin, triptorelin, goserelin, nafarelin, histrelin, deslorelin, meterelin, and lecirelin.

Embodiment II-93. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the method further comprises administering a second dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

Embodiment II-94. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-93, wherein the second dose is administered within about 8 to about 60 hours after administration of the initial dose.

Embodiment II-95. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-93 or II-94, wherein the method further comprises administering a third dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

Embodiment II-96. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-95, wherein the third dose is administered within about 8 to about 60 hours after administration of the second dose.

Embodiment II-97. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-95 or II-96, wherein the method further comprises administration of one to five additional doses of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

Embodiment II-98. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-97, wherein the administration of the one to five additional doses is within about 8 to about 60 hours after the prior additional dose is administered.

Embodiment II-99. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the method further comprises administering one or more doses of a progestogen.

Embodiment II-100. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of Embodiments II-73 to II-98, wherein the method does not comprise administering one or more doses of a progestogen.

Embodiment II-101. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein one or more of the initial dose, second dose, third dose, or one to five additional doses are administered via injection.

Embodiment II-102. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-101, wherein the injection is an intramuscular or subcutaneous injection.

Embodiment II-103. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein any one or more of the initial dose, second dose, third dose, or one to five additional doses is from about 0.0003 mg to about 0.03 mg.

Embodiment II-104. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the woman is undergoing COS.

Embodiment II-105. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the ART therapy is selected from the group consisting of oocyte donation, oocyte banking, ICSI, IVF, an ET process, ovulation induction, and intrauterine insemination.

Embodiment II-106. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the woman has one or more of PCOS, serum AMH greater than 15 pmol/L, total AFC greater than 23 via ultrasound, serum estradiol E2 greater than 3000 pg/mL, or has experienced one or more previous episodes of OHSS.

Embodiment II-107. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the woman is any one or more of anovulatory, or of advanced maternal age, or is experiencing secondary ovarian failure, oligomenorrhea, amenorrhea, endometriosis, or polycystic ovarian syndrome (PCOS).

Embodiment II-108. 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use in a method of inducing final follicular maturation and early luteinization in a woman who is undergoing ART, has undergone pituitary desensitization and has been pre-treated with follicle stimulating hormones as part of ART, said method comprising administering to the woman an initial dose of about 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of the pharmaceutically acceptable salt thereof.

Embodiment II-109. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-108, wherein after the initial dose is administered, the woman's endogenous LH level in blood is elevated compared to the woman's endogenous LH level in blood prior to administration of the initial dose.

Embodiment II-110. 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use in a method of inducing ovulation in a woman who is anovulatory infertile, wherein said infertility is not due to primary ovarian failure, said method comprising administering to the woman an initial dose of 0.00003 mg to about 0.030 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of the pharmaceutically acceptable salt thereof.

Embodiment II-111. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to Embodiment II-110, wherein after the initial dose is administered, the woman's endogenous LH level in blood is elevated compared to the woman's endogenous LH level in blood prior to administration of the initial dose.

Embodiment II-112. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of Embodiments II-108 to II-111, wherein the woman is at risk for OHSS.

Embodiment II-113. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of the preceding Embodiments, wherein the initial dose is 0.001 mg to about 0.003 mg 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

Embodiment II-114. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of Embodiments II-73 to II-112, wherein the initial dose is 0.001 mg to about 0.030 mg of 2-(N-acetyl-D-tyrosyl-trans-4-hydroxy-L-prolyl-L-asparaginyl-L-threonyl-L-phenyl alanyl) hydrazinocarbonyl-L-leucyl-Nω-methyl-L-arginyl-L-tryptophanamide, or a corresponding amount of a pharmaceutically acceptable salt thereof.

Embodiment II-115. The 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide or a pharmaceutically acceptable salt thereof for use according to any one of Embodiments II-73 to II-112, wherein the initial dose is 0.0003 mg to about 0.003 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

Embodiment II-116. Use of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for the manufacture of a medicament for elevating endogenous LH level in a woman who is undergoing ART and who is at risk for OHSS.

Embodiment II-117. Use of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for the manufacture of a medicament for increasing endogenous LH level in a woman undergoing ART.

Embodiment II-118. Use of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for the manufacture of a medicament for inducing final follicular maturation and early luteinization in a woman who is undergoing ART, has undergone pituitary desensitization and has been pretreated with follicle stimulating hormones as part of ART.

Embodiment II-119. Use of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a pharmaceutically acceptable salt thereof, for the manufacture of a medicament for inducing ovulation in a woman who is anovulatory infertile, wherein said infertility is not due to primary ovarian failure.

What is claimed is:

1. A method of increasing endogenous luteinizing hormone (LH) level in a woman in need thereof, the method comprising: administering to the woman an initial dose of about 0.0003 mg to 0.015 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, and one or more doses of a progestogen, wherein the maximum endogenous LH level in blood occurs between about 12 hours and about 48 hours after administration of the initial dose.

2. The method of claim 1, wherein the maximum endogenous LH level in blood occurs between about 18 hours and about 48 hours after administration of the initial dose.

3. The method of claim 1, wherein oocyte maturation occurs without the administration of exogenous human chorionic gonadotropin or exogenous LH.

4. The method of claim 1, wherein the initial dose is administered when at least three ovarian follicles of at least 14 mm are visible via ultrasound.

5. The method of claim 1, wherein the initial dose is administered when at least three ovarian follicles of at least 18 mm are visible via ultrasound.

6. The method of claim 1, wherein the initial dose is administered when serum estradiol concentration is at least 0.49 nmol/L.

7. The method of claim 1, wherein the method comprises administration of a GnRH antagonist about 2 days to about 10 days prior to administration of the initial dose.

8. The method of claim 7, wherein the GnRH antagonist is selected from the group consisting of relugolix, elagolix, cetrorelix, ganirelix, abarelix, nal-blu, antide, azaline B, degarelix, D63153 (ozarelix), OBE2109, and teverelix.

9. The method of claim 1, wherein the method comprises administering a second dose of about 0.0003 mg to 0.015 mg of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof.

10. The method of claim 1, wherein the woman has one or more of polycystic ovarian syndrome, serum anti-Müllerian hormone greater than 15 pmol/L, total antral follicle count greater than 23 via ultrasound, serum estradiol E2 greater than 3000 pg/mL, or has experienced one or more previous episodes of ovarian hyperstimulation syndrome.

11. The method of claim 1, wherein the woman is any one or more of anovulatory, or of advanced maternal age, or is experiencing secondary ovarian failure, oligomenorrhea, amenorrhea, endometriosis, or polycystic ovarian syndrome.

12. The method of claim 1, wherein the woman is at risk for ovarian hyperstimulation syndrome.

13. The method of claim 1, wherein the woman does not experience one or more symptoms of ovarian hyperstimulation syndrome after administration of the initial dose.

14. The method of claim 1, wherein the woman has ovarian hyperstimulation syndrome and wherein after administration of the initial dose, the woman does not experience a worsening of one or more symptoms of ovarian hyperstimulation syndrome.

15. The method of claim 1, wherein the woman's endogenous LH level in blood is elevated for at least 48 hours after administration of the initial dose of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, compared to the woman's endogenous LH level in blood prior to administration of the initial dose.

16. The method of claim 1, wherein the woman's endogenous LH level in blood is elevated between about 14 hours to about 84 hours after administration of the initial dose of 2-(N-acetyl-D-tyrosyl-trans-4-hydroxy-L-prolyl-L-asparaginyl-L-threonyl-L-phenylalanyl) hydrazinocarbonyl-L-leucyl-Nω-methyl-L-arginyl-L-tryptophanamide, or a corresponding amount of a pharmaceutically acceptable salt thereof, compared to the woman's endogenous LH level in blood prior to administration of the initial dose.

17. The method of claim 1, wherein the progestogen is progesterone, dydrogesterone, or medrogesterone.

18. The method of claim 1, wherein the progestogen is medroxyprogesterone acetate.

19. The method of claim 1, wherein one or more doses of the one or more doses of the progestogen are administered from oocyte retrieval until up to 12 weeks after retrieval.

20. The method of claim 1, wherein one or more doses of the one or more doses of the progestogen are administered after the initial dose.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is Acetyl-D-Tyrosine
<220> FEATURE:
<221> NAME/KEY: MISC_FEATURE
<222> LOCATION: (2)..(2)
<223> OTHER INFORMATION: Xaa is trans-4-hydroxyproline
<220> FEATURE:
<221> NAME/KEY: MISC_FEATURE
<222> LOCATION: (6)..(6)
<223> OTHER INFORMATION: Xaa is Azaglycine
<220> FEATURE:
<221> NAME/KEY: MISC_FEATURE
<222> LOCATION: (8)..(8)
<223> OTHER INFORMATION: Xaa is N-omega-methylarginine
<220> FEATURE:
<221> NAME/KEY: MOD_RES
<222> LOCATION: (9)..(9)
<223> OTHER INFORMATION: AMIDATION

<400> SEQUENCE: 1

Xaa Xaa Asn Thr Phe Xaa Leu Xaa Trp
1               5
```